(«12») United States Patent
Burgess et al.

(10) Patent No.: US 9,956,210 B2
(45) Date of Patent: May 1, 2018

(54) ENHANCER OF ZESTE HOMOLOG 2 INHIBITORS

(71) Applicant: GlaxoSmithKline LLC, Wilmington, DE (US)

(72) Inventors: Joelle Lorraine Burgess, Collegeville, PA (US); Steven David Knight, Collegeville, PA (US)

(73) Assignee: GLAXOSMITHKLINE LLC, Wilmington, New Castle, DE (US)

( * ) Notice: Subject to any disclaimer, the term of this patent is extended or adjusted under 35 U.S.C. 154(b) by 0 days. days.

(21) Appl. No.: 15/379,649

(22) Filed: Dec. 15, 2016

(65) Prior Publication Data

US 2017/0095461 A1    Apr. 6, 2017

Related U.S. Application Data

(62) Division of application No. 14/400,896, filed as application No. PCT/US2013/041115 on May 15, 2013, now Pat. No. 9,562,041.

(60) Provisional application No. 61/647,713, filed on May 16, 2012.

(51) Int. Cl.
| | |
|---|---|
| A61K 31/4412 | (2006.01) |
| A61K 31/496 | (2006.01) |
| A61K 31/444 | (2006.01) |
| A61K 31/4439 | (2006.01) |
| A61K 31/4545 | (2006.01) |
| A61K 31/443 | (2006.01) |
| A61K 31/4433 | (2006.01) |

(52) U.S. Cl.
CPC ........ *A61K 31/4412* (2013.01); *A61K 31/443* (2013.01); *A61K 31/444* (2013.01); *A61K 31/4433* (2013.01); *A61K 31/4439* (2013.01); *A61K 31/4545* (2013.01); *A61K 31/496* (2013.01)

(58) Field of Classification Search
CPC .................................................. A61K 31/4412
USPC ....................................................... 514/351
See application file for complete search history.

(56) References Cited

U.S. PATENT DOCUMENTS

| 8,410,088 B2 | 4/2013 | Kuntz et al. |
|---|---|---|
| 8,536,179 B2 | 9/2013 | Miller et al. |
| 8,598,167 B1 | 12/2013 | Kuntz et al. |
| 8,637,509 B2 | 1/2014 | Burgess et al. |
| 8,765,732 B2 | 7/2014 | Kuntz et al. |
| 8,765,792 B2 | 7/2014 | Knight et al. |
| 8,846,935 B2 | 9/2014 | Duquenne et al. |
| 2009/0181983 A1 | 7/2009 | Corte, Jr. |
| 2012/0264734 A1 | 10/2012 | Kuntz et al. |
| 2013/0040906 A1 | 2/2013 | Kuntz et al. |
| 2013/0053383 A1 | 2/2013 | Duquenne et al. |
| 2013/0245016 A1 | 9/2013 | Knight et al. |
| 2013/0345200 A1 | 12/2013 | Brackley et al. |
| 2014/0142083 A1 | 5/2014 | Kuntz et al. |

FOREIGN PATENT DOCUMENTS

| WO | WO 2011/140324 A1 | 11/2011 |
|---|---|---|
| WO | WO 2012/005805 A1 | 1/2012 |
| WO | WO 2012/118812 A2 | 9/2012 |
| WO | WO 2013/155317 A1 | 10/2013 |

OTHER PUBLICATIONS

Yamagishi et al., "Targeting EZH2, etc.," www.oncology.com 29(00), 2017, 1-7.*
Kondo, "Targeting histone, etc.," J. Biochem., 2014;156(5): 249-257.*
Karsii-Ceppioglu et al., "Epigenetic mechanisms, etc.," Epigeomics (2014) 6(6), 651-664.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Golub et al, Science, vol. 286, Oct. 15, 1999, pp. 531-537.*
Chopra et al., "Dusturbing the histone, etc.," Cancer Genetics 208 (2015) 192-205.*
Martinez-Fernandez et al., "EZH2 in Bladder, etc.," Int. J. Mol. Sci. 2015, 16, 27107-27132.*
Stephenson et al., "Drug Discovery, etc.," Advanced Drug Delivery Reviews, (2017), http://dx.doi.org/10.1016/j.addr.2017.06.010, pp. 1-16.*
Catherine Baugé, et al.: Histone Methylases as Novel Drug Targets: Developing Inhibitors of EZH2; Future Med. Chem. (2014) 6(17), 1943-1965.

(Continued)

*Primary Examiner* — Patricia L Morris
(74) *Attorney, Agent, or Firm* — Duke M. Fitch; Kathryn A. Lutomski; Edward R. Gimmi

(57) ABSTRACT

This invention relates to novel substituted benzamide according to Formula (I) which are inhibitors of Enhancer of Zeste Homolog 2 (EZH2), to pharmaceutical compositions containing them, to processes for their preparation, and to their use in therapy for the treatment of cancers.

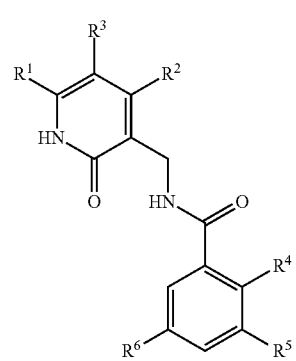

1 Claim, No Drawings

(56) References Cited

OTHER PUBLICATIONS

Dorothy Brach, et al.; EZH2 Inhibition by Tazemetostat Results in Altered Dependency on B-cell Activation Signaling in DLBCL; Mol Cancer Ther; 16(11) Nov. 2017, 2586-2597.
Uttara Soumyanarayanan, et al.: Recently Discovered EZH2 and EHMT2 (G9a) Inhibitors; Future Med. Chem. (2016) 8(13), 1635-1654.

\* cited by examiner

ENHANCER OF ZESTE HOMOLOG 2 INHIBITORS

FIELD OF THE INVENTION

This invention relates to substituted benzamide compounds which inhibit Enhancer of Zeste Homolog 2 (EZH2) and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al., 2002; Kleer et al., 2003; Breuer et al., 2004; Bachmann et al., 2005; Weikert et al., 2005; Sudo et al., 2005; Bachmann et al., 2006). For instance, there is a greater risk of recurrence after prostatectomy in tumors expressing high levels of EZH2, increased metastasis, shorter disease-free survival and increased death in breast cancer patients with high EZH2 levels (Varambally et al., 2002; Kleer et al., 2003). More recently, inactivating mutations in UTX (ubiquitously transcribed tetratricopeptixe repeats X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al., 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism. In addition, EZH2 overexpression in immortalized or primary epithelial cells promotes anchorage independent growth and invasion and requires EZH2 catalytic activity. (Kleer et al., 2003; Cao et al., 2008).

Thus, there is strong evidence to suggest that inhibition of EZH2 activity decreases cellular proliferation and invasion. Accordingly, compounds that inhibit EZH2 activity would be useful for the treatment of cancer.

SUMMARY OF THE INVENTION

The present invention relates to compounds according to Formula (I), and pharmaceutically acceptable salts thereof.

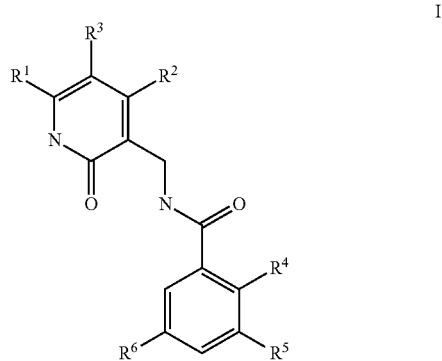

Wherein $R^1$ and $R^2$ are selected independently from the group consisting of hydrogen, $(C_1-C_8)$alkyl, $(C_2-C_8)$alkenyl, $(C_2-C_8)$alkynyl, $(C_3-C_8)$cycloalkyl, $(C_3-C_8)$cycloalkyl-$(C_1-C_8)$alkyl, $(C_3-C_8)$cycloalkyl-$(C_2-C_8)$alkenyl, $(C_5-C_8)$cycloalkenyl, $(C_5-C_8)$cycloalkenyl-$(C_1-C_8)$alkyl, $(C_5-C_8)$cycloalkenyl-$(C_2-C_8)$alkenyl, $(C_6-C_{10})$bicycloalkyl, heterocycloalkyl, heterocycloalkyl-$(C_1-C_8)$alkyl, heterocycloalkyl-$(C_2-C_8)$alkenyl, aryl, aryl-$(C_1-C_8)$alkyl, aryl-$(C_2-C_8)$alkenyl, heteroaryl, heteroaryl-$(C_1-C_8)$alkyl, heteroaryl-$(C_2-C_8)$alkenyl, halo, cyano, —C(O)$R^a$, —CO$_2R^a$, —C(O)NR$^a$R$^b$, —C(O)NR$^a$NR$^a$R$^b$, —SR$^a$, —S(O)R$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —NR$^a$NR$^a$C(O)OR$^a$, —OR$^a$, —OC(O)R$^a$, and —OC(O)NR$^a$R$^b$, wherein any $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl is optionally substituted 1, 2 or 3 times by groups independently selected from the group consisting of hydroxyl, halo, amino, nitro, $(C_1-C_3)$alkyl, $(C_3-C_8)$cycloalkyl, cyano, $(C_1-C_3)$alkoxy, —NR$^a$R$^b$ and —CO$_2$R$^a$;

$R^3$ is H or halo;

R⁴ is selected from the group consisting of $(C_1-C_3)$alkoxy, $(C_1-C_3)$alkyl, hydroxyl, halo, cyano, $(C_3-C_6)$cycloalkyl, $(C_3-C_6)$heterocycloalkyl, $NR^aR^b$, $(C_1-C_3)$haloalkyl, and $(C_1-C_3)$ hydroxylalkyl;

R⁵ is selected from the group consisting of $(C_4-C_8)$alkyl, $(C_3-C_8)$alkoxy, $(C_3-C_8)$cycloalkyoxy-, $(C_3-C_8)$heterocycloalkyloxy-, $(C_4-C_8)$cycloalkyl, aryl, heteroaryl and $NR^aR^b$, wherein said $(C_4-C_8)$alkyl, $(C_3-C_8)$alkoxy, $(C_3-C_8)$cycloalkyoxy-, $(C_3-C_8)$heterocycloalkyloxy-, $(C_4-C_8)$cycloalkyl, aryl or heteroaryl is optionally substituted by 1, 2 or 3 groups independently selected from the group consisting of hydroxyl, halo, amino, nitro, $(C_1-C_3)$alkyl, $(C_3-C_8)$cycloalkyl, cyano, $(C_1-C_3)$alkoxy and $-CO_2R^a$;

R⁶ is selected from the group consisting of hydrogen, halo, $(C_1-C_8)$alkyl, $(C_2-C_8)$alkenyl, $-B(OH)_2$, $(C_2-C_8)$alkynyl, $(C_3-C_8)$cycloalkyl, $(C_3-C_8)$cycloalkyl-$(C_1-C_8)$alkyl, $(C_5-C_8)$cycloalkenyl, $(C_5-C_8)$cycloalkenyl-$(C_1-C_8)$alkyl, $(C_6-C_{10})$bicycloalkyl, heterocycloalkyl, heterocycloalkyl-$(C_1-C_8)$alkyl, aryl, aryl-$(C_1-C_8)$alkyl, heteroaryl, heteroaryl-$(C_1-C_8)$alkyl, cyano, $-C(O)R^a$, $-CO_2R^a$, $-C(O)NR^aR^b$, $-C(O)NR^aNR^aR^b$, $-SR^a$, $-S(O)R^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-NR^aNR^aR^b$, $-NR^aNR^aC(O)R^b$, $-NR^aNR^aC(O)NR^aR^b$, $-NR^aNR^aC(O)OR^a$, $-OR^a$, $-OC(O)R^a$, and $-OC(O)NR^aR^b$, wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of $-O(C_1-C_6)$alkyl$(R^c)_{1-2}$, $-S(C_1-C_6)$alkyl$(R^c)_{1-2}$, $-(C_1-C_6)$alkyl$(R^c)_{1-2}$, $(C_1-C_8)$alkyl-heterocycloalkyl-, $(C_3-C_8)$cycloalkyl-heterocycloalkyl-, halo, $(C_1-C_6)$alkyl, $(C_3-C_8)$cycloalkyl, $(C_5-C_8)$cycloalkenyl, $(C_1-C_6)$haloalkyl, cyano, $-C(O)R^a$, $-CO_2R^a$, $-C(O)NR^aR^b$, $-SR^a$, $-S(O)R^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-OR^a$, $-OC(O)R^a$, $-OC(O)NR^aR^b$, heterocycloalkyl, aryl, heteroaryl, aryl$(C_1-C_4)$alkyl-, and heteroaryl$(C_1-C_4)$alkyl-, wherein any aryl or heteroaryl moiety of said aryl, heteroaryl, aryl$(C_1-C_4)$alkyl, or heteroaryl $(C_1-C_4)$alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, hydroxyl, $(C_1-C_6)$haloalkyl, cyano, $-C(O)R^a$, $-CO_2R^a$, $-C(O)NR^aR^b$, $-SR^a$, $-S(O)R^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-OR^a$, $-OC(O)R^a$, and $-OC(O)NR^aR^b$;

each $R^c$ is independently $(C_1-C_4)$alkylamino, $-NR^aSO_2R^b$, $-S(O)R^a$, $-SO_2R^a$, $-NR^aC(O)OR^a$, $-NR^aR^b$, or $-CO_2R^a$;

$R^a$ and $R^b$ are each independently hydrogen, $(C_1-C_8)$alkyl, $(C_2-C_8)$alkenyl, $(C_2-C_8)$alkynyl, $(C_3-C_{10})$cycloalkyl, $(C_5-C_8)$cycloalkenyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $-N((C_1-C_4)$alkyl$)_2$, $-CO_2H$, $-CO_2(C_1-C_4)$alkyl, $-CONH_2$, $-CONH(C_1-C_4)$alkyl, $-CON((C_1-C_4)$alkyl$)_2$, $-SO_2(C_1-C_4)$alkyl, $-SO_2NH_2$, $-SO_2NH(C_1-C_4)$alkyl, or $-SO_2N((C_1-C_4)$alkyl$)_2$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring.

Second aspect of this invention relates to a method of inducing apoptosis in cancer cells of solid tumors; treating solid tumor cancers.

Third aspect of the invention relates to pharmaceutical preparations comprising compounds of formula (I) and pharmaceutically acceptable excipients.

In a fourth aspect, there is provided the use of a compound of formula (I) and/or a pharmaceutically acceptable salt or solvate thereof, in the preparation of a medicament for use in the treatment of a disorder mediated by inhibiting EZH2, such as inducing apoptosis in cancer cells.

In a fifth aspect there is provided methods of co-administering the presently invented compounds of formula (I) with other active ingredients.

DETAILED DESCRIPTION OF THE INVENTION

The present invention relates to compounds of Formula (I),

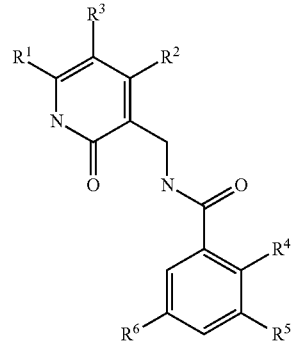

Wherein $R^1$ and $R^2$ are selected independently from the group consisting of hydrogen, $(C_1-C_8)$alkyl, $(C_2-C_8)$alkenyl, $(C_2-C_8)$alkynyl, $(C_3-C_8)$cycloalkyl, $(C_3-C_8)$cycloalkyl-$(C_1-C_8)$alkyl, $(C_3-C_8)$cycloalkyl-$(C_2-C_8)$alkenyl, $(C_5-C_8)$cycloalkenyl, $(C_5-C_8)$cycloalkenyl-$(C_1-C_8)$alkyl, $(C_5-C_8)$cycloalkenyl-$(C_2-C_8)$alkenyl, $(C_6-C_{10})$bicycloalkyl, heterocycloalkyl, heterocycloalkyl-$(C_1-C_8)$alkyl, heterocycloalkyl-$(C_2-C_8)$alkenyl, aryl, aryl-$(C_1-C_8)$alkyl, aryl-$(C_2-C_8)$alkenyl, heteroaryl, heteroaryl-$(C_1-C_8)$alkyl, heteroaryl-$(C_2-C_8)$alkenyl, halo, cyano, $-C(O)R^a$, $-CO_2R^a$, $-C(O)NR^aR^b$, $-C(O)NR^aNR^aR^b$, $-SR^a$, $-S(O)R^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-NR^aNR^aR^b$, $-NR^aNR^aC(O)R^b$, $-NR^aNR^aC(O)NR^aR^b$, $-NR^aNR^aC(O)OR^a$, $-OR^a$, $-OC(O)R^a$, and $-OC(O)NR^aR^b$, wherein any $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl is optionally substituted 1, 2 or 3 times by groups independently selected from the group consisting of hydroxyl, halo, amino, nitro, $(C_1-C_3)$alkyl, $(C_3-C_8)$cycloalkyl, cyano, $(C_1-C_3)$alkoxy, —$NR^aR^b$ and —$CO_2R^a$;

$R^3$ is H or halo;

$R^4$ is selected from the group consisting of $(C_1-C_3)$alkoxy, $(C_1-C_3)$alkyl, hydroxyl, halo, cyano, $(C_3-C_6)$cycloalkyl, $(C_3-C_6)$heterocycloalkyl, $NR^aR^b$, $(C_1-C_3)$haloalkyl, and $(C_1-C_3)$ hydroxylalkyl;

$R^5$ is selected from the group consisting of $(C_4-C_8)$alkyl, $(C_3-C_8)$alkoxy, $(C_3-C_8)$cycloalkyoxy-, $(C_3-C_8)$heterocycloalkyloxy-, $(C_4-C_8)$cycloalkyl, aryl, heteroaryl and $NR^aR^b$, wherein said $(C_4-C_8)$alkyl, $(C_3-C_8)$alkoxy, $(C_3-C_8)$cycloalkyoxy-, $(C_3-C_8)$heterocycloalkyloxy-, $(C_4-C_8)$cycloalkyl, aryl or heteroaryl is optionally substituted by 1, 2 or 3 groups independently selected from the group consisting of hydroxyl, halo, amino, nitro, $(C_1-C_3)$alkyl, $(C_3-C_8)$cycloalkyl, cyano, $(C_1-C_3)$alkoxy and —$CO_2R^a$;

$R^6$ is selected from the group consisting of hydrogen, halo, $(C_1-C_8)$alkyl, $(C_2-C_8)$alkenyl, —$B(OH)_2$, $(C_2-C_8)$alkynyl, $(C_3-C_8)$cycloalkyl, $(C_3-C_8)$cycloalkyl-$(C_1-C_8)$alkyl, $(C_5-C_8)$cycloalkenyl, $(C_5-C_8)$cycloalkenyl-$(C_1-C_8)$alkyl, $(C_6-C_{10})$bicycloalkyl, heterocycloalkyl, heterocycloalkyl-$(C_1-C_8)$alkyl, aryl, aryl-$(C_1-C_8)$alkyl, heteroaryl, heteroaryl-$(C_1-C_8)$alkyl, cyano, —$C(O)R^a$, —$CO_2R^a$, —$C(O)NR^aR^b$, —$C(O)NR^aNR^aR^b$, —$SR^a$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$, wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, $(C_1-C_8)$alkyl-heterocycloalkyl-, $(C_3-C_8)$cycloalkyl-heterocycloalkyl-, halo, $(C_1-C_6)$alkyl, $(C_3-C_8)$cycloalkyl, $(C_5-C_8)$cycloalkenyl, $(C_1-C_6)$haloalkyl, cyano, —$C(O)R^a$, —$CO_2R^a$, —$C(O)NR^aR^b$, —$SR^a$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl-, and heteroaryl$(C_1-C_4)$alkyl-, wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, hydroxyl, $(C_1-C_6)$haloalkyl, cyano, —$C(O)R^a$, —$CO_2R^a$, —$C(O)NR^aR^b$, —$SR^a$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

each $R^c$ is independently $(C_1-C_4)$alkylamino, —$NR^aSO_2R^b$, —$S(O)R^a$, —$SO_2R^a$, —$NR^aC(O)OR^a$, —$NR^aR^b$, or —$CO_2R^a$;

$R^a$ and $R^b$ are each independently hydrogen, $(C_1-C_8)$alkyl, $(C_2-C_8)$alkenyl, $(C_2-C_8)$alkynyl, $(C_3-C_{10})$cycloalkyl, $(C_5-C_8)$cycloalkenyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, —$N((C_1-C_4)alkyl)_2$, —$CO_2H$, —$CO_2(C_1-C_4)$alkyl, —$CONH_2$, —$CONH(C_1-C_4)$alkyl, —$CON((C_1-C_4)alkyl)_2$, —$SO_2(C_1-C_4)$alkyl, —$SO_2NH_2$, —$SO_2NH(C_1-C_4)$alkyl, or —$SO_2N((C_1-C_4)alkyl)_2$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)alkyl)((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a pharmaceutically acceptable salt thereof.

In one embodiment, this invention relates to compounds of Formula (I), wherein $R^1$ is $(C_1-C_6)$alkyl, or a pharmaceutically acceptable salts thereof.

In another embodiment, this invention relates to compounds of Formula (I), wherein $R^2$ is $(C_1-C_6)$alkyl or benzyl, or a pharmaceutically acceptable salts thereof.

In another embodiment, this invention relates to compounds of Formula (I), wherein $R^1$ and $R^2$ are methyl, $R^3$ is hydrogen, or a pharmaceutically acceptable salts thereof.

In another embodiment, this invention relates to compounds of Formula (I), wherein $R^1$ is methyl, $R^2$ is methyl, $R^3$ is hydrogen and $R^4$ is chloro, or a pharmaceutically acceptable salts thereof.

In another embodiment, this invention relates to compounds of Formula (I), wherein $R^1$ is methyl, $R^2$ is methyl, $R^3$ is hydrogen and $R^4$ is methyl, or a pharmaceutically acceptable salts thereof.

In another embodiment, this invention relates to compounds of Formula (I), wherein $R^1$ is methyl, $R^2$ is methyl, $R^3$ is hydrogen, $R^4$ is methyl and $R^5$ is selected from the group consisting of $(C_3-C_8)$alkoxy, $(C_3-C_8)$cycloalkyoxy-, $(C_3-C_8)$heterocycloalkyloxy-, heteroaryl and $NR^aR^b$, wherein said $(C_3-C_8)$alkoxy, $(C_3-C_8)$cycloalkyoxy-, $(C_3-C_8)$heterocycloalkyloxy-, or heteroaryl is optionally substituted by 1, 2 or 3 groups independently selected from the group consisting of hydroxyl, halo, amino, nitro, $(C_1-C_3)$alkyl, $(C_3-C_8)$cycloalkyl, cyano, $(C_1-C_3)$alkoxy and —$CO_2R^a$; or a pharmaceutically acceptable salt thereof.

In another embodiment, this invention relates to compounds of Formula (I), wherein $R^1$ is methyl, $R^2$ is methyl, $R^3$ is hydrogen, $R^4$ is methyl and $R^6$ is selected from the group consisting of hydrogen, cyano, halo, —$SO_2(C_1-C_3)$alkyl; pyridinyl, thiazolyl, and phenyl, wherein said pyridinyl, thiazolyl or phenyl is optionally substituted by 1, 2 or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, $(C_1-C_8)$alkyl-heterocycloalkyl-, $(C_3-C_8)$cycloalkyl-heterocycloalkyl-, halo, $(C_1-C_6)$alkyl, $(C_3-C_8)$cycloalkyl, $(C_5-C_8)$cycloalkenyl, $(C_1-C_6)$haloalkyl, cyano, —$C(O)R^a$, —$CO_2R^a$, —$C(O)NR^aR^b$, —$SR^a$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl-, and heteroaryl$(C_1-C_4)$alkyl-; or a pharmaceutically acceptable salt thereof.

In another embodiment, this invention relates to compounds of Formula (I), wherein $R^1$ is methyl, $R^2$ is methyl, $R^3$ is hydrogen, $R^4$ is methyl and $R^5$ is the group consisting of (C$_3$-C$_8$)alkoxy, (C$_3$-C$_8$)cycloalkyloxy-, (C$_3$-C$_8$)heterocycloalkyloxy-, and NR$^6$R$^7$; wherein R$^6$ and R$^7$ are independently selected from groups consisting of hydrogen, (C$_1$-C$_4$)alkyl, hydroxyl(C$_1$-C$_3$)alkyl, (C$_1$-C$_3$)alkoxy(C$_1$-C$_3$)alkyl- and —C(=O)(C$_1$-C$_3$)alkyl; or R$^6$ and R$^7$, taken together with the N to which they are attached, form a three to seven membered ring, wherein said ring is optionally substituted one to three times by R$^8$; wherein said R$^8$ is selected from groups consisting of (C$_1$-C$_3$)alkyl, halo and hydroxyl.

In another embodiment, this invention relates to compounds of Formula (I), wherein R$^1$ is methyl, R$^2$ is methyl, R$^3$ is hydrogen, R$^4$ is methyl and R$^6$ is selected from the group consisting of hydrogen, cyano, halo, —SO$_2$(C$_1$-C$_3$)alkyl, pyridinyl, thiazolyl, and phenyl; wherein said pyridinyl, thiazolyl and phenyl may be optionally substituted by 1, 2 or 3 groups independently selected from the group consisting of (C$_1$-C$_3$)alkyl, (C$_1$-C$_3$)alkoxy, optionally substituted heterocycloalkyl and —CH$_2$N(R$^9$)$_2$, wherein each R$^9$ is independently selected from the group consisting of hydrogen and (C$_1$-C$_3$)alkyl.

Specific compounds of this invention include:

5-Bromo-2-methyl-3-[(1-methylethyl)amino]-N-[(6-methyl-2-oxo-4-propyl-1,2-dihydro-3-pyridinyl)methyl]benzamide;

2-Methyl-3-[(1-methylethyl)amino]-N-[(6-methyl-2-oxo-4-propyl-1,2-dihydro-3-pyridinyl)methyl]-5-[6-(4-methyl-1-piperazinyl)-3-pyridinyl]benzamide;

5-Bromo-N-[(4,6-dimethyl-2-oxo-1,2-dihydro-3-pyridinyl)methyl]-2-methyl-3-[(1-methylethyl)amino]benzamide;

5-Bromo-2-methyl-3-[(1-methylethyl)amino]-N-{[6-methyl-2-oxo-4-(phenylmethyl)-1,2-dihydro-3-pyridinyl]methyl}benzamide;

2-Methyl-3-[(1-methylethyl)amino]-N-[(6-methyl-2-oxo-4-propyl-1,2-dihydro-3-pyridinyl)methyl]-5-[6-(methyloxy)-3-pyridinyl]benzamide;

N-[(4,6-Dimethyl-2-oxo-1,2-dihydro-3-pyridinyl)methyl]-2-methyl-3-[(1-methylethyl)amino]-5-[6-(methyloxy)-3-pyridinyl]benzamide;

4'-[(Dimethylamino)methyl]-N-[(4,6-dimethyl-2-oxo-1,2-dihydro-3-pyridinyl)methyl]-4-methyl-5-[(1-methylethyl)amino]-3-biphenylcarboxamide;

5-(6-Amino-3-pyridinyl)-N-[(4,6-dimethyl-2-oxo-1,2-dihydro-3-pyridinyl)methyl]-2-methyl-3-[(1-methylethyl)amino]benzamide;

N-[(4,6-Dimethyl-2-oxo-1,2-dihydro-3-pyridinyl)methyl]-2-methyl-3-[(1-methylethyl)amino]-5-[6-(1-piperazinyl)-3-pyridinyl]benzamide;

N-((4,6-dimethyl-2-oxo-1,2-dihydropyridin-3-yl)methyl)-3-(isopropylamino)-5-(2-methoxythiazol-5-yl)-2-methylbenzamide;

5-Bromo-3-(sec-butylamino)-N-((4,6-dimethyl-2-oxo-1,2-dihydropyridin-3-yl)methyl)-2-methylbenzamide;

3-(sec-Butylamino)-N-((4,6-dimethyl-2-oxo-1,2-dihydropyridin-3-yl)methyl)-5-(2-methoxythiazol-5-yl)-2-methylbenzamide;

5-Bromo-2-methyl-3-[methyl(1-methylethyl)amino]-N-[(6-methyl-2-oxo-4-propyl-1,2-dihydro-3-pyridinyl)methyl]benzamide;

5-Bromo-N-((4,6-dimethyl-2-oxo-1,2-dihydropyridin-3-yl)methyl)-3-(isopropyl(methyl)amino)-2-methylbenzamide;

N-((4,6-dimethyl-2-oxo-1,2-dihydropyridin-3-yl)methyl)-3-(isopropyl(methyl)amino)-5-(2-methoxythiazol-5-yl)-2-methylbenzamide;

5-Bromo-3-(sec-butyl(methyl)amino)-N-((4,6-dimethyl-2-oxo-1,2-dihydropyridin-3-yl)methyl)-2-methylbenzamide;

3-(sec-Butyl(methyl)amino)-N-((4,6-dimethyl-2-oxo-1,2-dihydropyridin-3-yl)methyl)-5-(2-methoxythiazol-5-yl)-2-methylbenzamide;

5-Bromo-N-((4,6-dimethyl-2-oxo-1,2-dihydropyridin-3-yl)methyl)-2-methyl-3-(2-methylpyrrolidin-1-yl)benzamide;

5-Bromo-N-((4,6-dimethyl-2-oxo-1,2-dihydropyridin-3-yl)methyl)-2-methyl-3-(2-methylpiperidin-1-yl)benzamide;

5-Bromo-3-(sec-butoxy)-N-((4,6-dimethyl-2-oxo-1,2-dihydropyridin-3-yl)methyl)-2-methylbenzamide;

5-Bromo-N-((4,6-dimethyl-2-oxo-1,2-dihydropyridin-3-yl)methyl)-3-isopropoxy-2-methylbenzamide;

3-[acetyl(1-methylpropyl)amino]-5-bromo-N-[(4,6-dimethyl-2-oxo-1,2-dihydro-3-pyridinyl)methyl]-2-methylbenzamide;

2,5-dichloro-N-[(4,6-dimethyl-2-oxo-1,2-dihydro-3-pyridinyl)methyl]-3-[(1-methylpropyl)amino]benzamide;

2,5-dichloro-N-[(4,6-dimethyl-2-oxo-1,2-dihydro-3-pyridinyl)methyl]-3-[(1-methylethyl)oxy]benzamide;

5-chloro-N-[(4,6-dimethyl-2-oxo-1,2-dihydro-3-pyridinyl)methyl]-2-methyl-3-{[1-methyl-2-(methyloxy)ethyl]amino}benzamide;

5-chloro-N-[(4,6-dimethyl-2-oxo-1,2-dihydro-3-pyridinyl)methyl]-3-[(2-hydroxy-1-methylethyl)amino]-2-methylbenzamide;

5-chloro-N-[(4,6-dimethyl-2-oxo-1,2-dihydro-3-pyridinyl)methyl]-2-methyl-3-[(1-methylethyl)oxy]benzamide;

5-chloro-3-(cyclopentyloxy)-N-[(4,6-dimethyl-2-oxo-1,2-dihydro-3-pyridinyl)methyl]-2-methylbenzamide;

2,5-dichloro-N-[(4,6-dimethyl-2-oxo-1,2-dihydro-3-pyridinyl)methyl]-3-(1-methyl-1H-pyrazol-5-yl)benzamide;

3-(sec-butoxy)-N-((4,6-dimethyl-2-oxo-1,2-dihydropyridin-3-yl)methyl)-2-methyl-5-(6-(4-methylpiperazin-1-yl)pyridin-3-yl)benzamide;

5-(sec-butoxy)-N-((4,6-dimethyl-2-oxo-1,2-dihydropyridin-3-yl)methyl)-3'-((dimethylamino)methyl)-4-methyl-[1,1'-biphenyl]-3-carboxamide;

N-((4,6-dimethyl-2-oxo-1,2-dihydropyridin-3-yl)methyl)-3-isopropoxy-2-methyl-5-(6-(piperazin-1-yl)pyridin-3-yl)benzamide;

N-((4,6-dimethyl-2-oxo-1,2-dihydropyridin-3-yl)methyl)-3-isopropoxy-2-methyl-5-(6-(4-methylpiperazin-1-yl)pyridin-3-yl)benzamide;

N-((4,6-dimethyl-2-oxo-1,2-dihydropyridin-3-yl)methyl)-3'-((dimethylamino)methyl)-5-isopropoxy-4-methyl-[1,1'-biphenyl]-3-carboxamide;

3-(sec-butoxy)-N-((4,6-dimethyl-2-oxo-1,2-dihydropyridin-3-yl)methyl)-2-methyl-5-(6-(piperazin-1-yl)pyridin-3-yl)benzamide;

N-((4,6-dimethyl-2-oxo-1,2-dihydropyridin-3-yl)methyl)-3-methoxy-2-methylbenzamide;

3-(sec-butoxy)-N-((4,6-dimethyl-2-oxo-1,2-dihydropyridin-3-yl)methyl)-2-methylbenzamide;

N-((4,6-dimethyl-2-oxo-1,2-dihydropyridin-3-yl)methyl)-3-isopropoxy-2-methylbenzamide;

N-((4,6-dimethyl-2-oxo-1,2-dihydropyridin-3-yl)methyl)-2-methyl-3-((tetrahydrofuran-3-yl)oxy)benzamide;

N-((4,6-dimethyl-2-oxo-1,2-dihydropyridin-3-yl)methyl)-2-methyl-3-((1-methylpyrrolidin-3-yl)oxy)benzamide;

N-((4,6-dimethyl-2-oxo-1,2-dihydropyridin-3-yl)methyl)-2-methyl-3-((tetrahydro-2H-pyran-4-yl)oxy)benzamide;

3-(sec-butoxy)-N-((4,6-dimethyl-2-oxo-1,2-dihydropyridin-3-yl)methyl)-2-methyl-5-(methylsulfonyl)benzamide;

N-((4,6-dimethyl-2-oxo-1,2-dihydropyridin-3-yl)methyl)-3-(isopropylamino)-2-methyl-5-(methylsulfonyl)benzamide;
3-(sec-butoxy)-5-cyano-N-((4,6-dimethyl-2-oxo-1,2-dihydropyridin-3-yl)methyl)-2-methylbenzamide;
5-cyano-N-((4,6-dimethyl-2-oxo-1,2-dihydropyridin-3-yl)methyl)-3-isopropoxy-2-methylbenzamide;
3-(sec-butoxy)-N-((4,6-dimethyl-2-oxo-1,2-dihydropyridin-3-yl)methyl)-5-methoxy-2-methylbenzamide;
N-((4,6-dimethyl-2-oxo-1,2-dihydropyridin-3-yl)methyl)-3-isopropoxy-5-methoxy-2-methylbenzamide;
N-((4,6-dimethyl-2-oxo-1,2-dihydropyridin-3-yl)methyl)-3-(isopropylamino)-2-methylbenzamide.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and 125I isotopes are particularly useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

The invention further provides a pharmaceutical composition (also referred to as pharmaceutical formulation) comprising a compound of Formula (I) or pharmaceutically acceptable salt thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

In accordance with another aspect of the invention there is provided a process for the preparation of a pharmaceutical composition comprising mixing (or admixing) a compound of Formula (I) or salt thereof with at least one excipient.

The present invention also provides a method of treatment in a mammal, especially a human. The compounds and compositions of the invention are used to treat cellular proliferation diseases. Disease states which can be treated by the methods and compositions provided herein include, but are not limited to, cancer (further discussed below), auto-immune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein is meant either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical antineoplastic agents useful in the present invention include, but are not limited to: alkylating agents, anti-metabolites, anti-tumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deactylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib mesylate (GLEEVEC®) is one example of a PDGFR inhibitor. Examples of VEGFR inhibitors include pazopanib, ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate β-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H, 12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b] quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I).

Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Definitions

Terms are used within their accepted meanings. The following definitions are meant to clarify, but not limit, the terms defined.

As used herein, the term "alkyl" represents a saturated, straight, or branched hydrocarbon moiety, preferably having from one to twelve carbon atoms. The term "$(C_1-C_6)$alkyl" refers to an alkyl moiety containing from 1 to 6 carbon atoms. Exemplary alkyls include, but are not limited to methyl, ethyl, n-propyl, isopropyl, n-butyl, isobutyl, s-butyl, t-butyl, pentyl, and hexyl.

As used herein, the term "haloalkyl" refers to an alkyl group, defined hereinabove, substituted with one or more halo substituents.

The term "alkylthio" as used herein is meant —S($C_1$-$C_8$alkyl) including —$SCH_3$, —$SCH_2CH_3$ and the like per the definition of alkyl above.

The term "acyloxy" means —OC(O)$C_1$-$C_8$alkyl and the like per the definition of alkyl above.

"Acylamino" means-N(H)C(O)$C_1$-$C_8$alkyl and the like per the definition of alkyl above.

"Aryloxy" means —O(aryl), —O(substituted aryl), —O(heteroaryl) or —O(substituted heteroaryl).

"Arylamino" means —NH(aryl), —NH(substituted aryl), —NH(heteroaryl) or —NH(substituted heteroaryl), and the like.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

The term "$C_5$-$C_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

As used herein, the term "hydroxylalkyl" refers to an alkyl group, defined hereinabove, substituted preferably with 1, 2 or 3 hydroxyl substituents.

As used herein, the term "cycloalkyl" refers to an unsubstituted or substituted mono- or polycyclic non-aromatic saturated ring, which optionally includes an alkylene linker through which the cycloalkyl may be attached. Exemplary "cycloalkyl" groups include, but are not limited to, cyclopropyl, cyclobutyl, cyclopentyl, cyclohexyl, cycloheptyl, and the like, as well as unsubstituted and substituted versions thereof.

As used herein, the term "bicycloalkyl" refers to two cycloalkyl groups, defined hereinabove, connecting with each other to form a bridged, fused or spiro bicycle compound. Representative bicycloalkyl groups include, not limited to, spiro[4.4]nonance, bicyclo[3.1.1]heptanes and bicyclo[3.2.0]heptanes.

As used herein, the term "alkoxy" refers to the group —$OR^a$, where $R^a$ is alkyl or cycloalkyl as defined above.

The terms "halogen" and "halo" represent chloro, fluoro, bromo, or iodo substituents. "Hydroxy" or "hydroxyl" is intended to mean the radical —OH.

"Heterocycloalkyl" represents a group or moiety comprising a non-aromatic, monovalent monocyclic or bicyclic radical, which is saturated or partially unsaturated, containing 3 to 10 ring atoms, which includes 1 to 3 heteroatoms independently selected from nitrogen, oxygen and sulfur, including N-oxides, sulfur oxides, and dioxides.

Illustrative examples of heterocycloalkyls useful in the present invention include, but are not limited to, azetidinyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl, 1,1-dioxidotetrahydro-2H-thiopyranyl and 1,5,9-triazacyclododecyl.

The term "aryl" refers to a carbocyclic aromatic moiety (such as phenyl or naphthyl) containing the specified number of carbon atoms, particularly from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl.

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 8 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary 5- to 6-membered heteroaryls include, but are not limited to, furanyl, thiophenyl, thienyl, pyrrolyl, imidazolyl, pyrazolyl, triazolyl, tetrazolyl, thiazolyl, isothiazolyl, 1, 2, 3-triazolyl, 1, 2, 4-triazolyl, oxazolyl, isoxazolyl, 1, 2, 3-oxadiazolyl, 1, 2, 5-oxadiazolyl, thiadiazolyl, isothiazolyl, tetrazolyl, pyridinyl, pyridazinyl, pyrazinyl, pyrimidinyl, and triazinyl. Other exemplary heteroaryl groups include, but are not limited to benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Suitable substituents for heteroaryl are described in the definition of "optionally substituted."

As used herein, the term "cyano" refers to the group —CN.

As used herein, the term "acetyl" refers to the group —C(=O)$R^b$, where $R^b$ is alkyl, cycloalkyl, or heterocyclyl, as each is defined herein.

As used herein, the term "optionally" means that the subsequently described event(s) may or may not occur, and includes both event(s) that occur and event(s) that do not occur.

As used herein, unless otherwise defined, the phrase "optionally substituted" or variations thereof denote an optional substitution, including multiple degrees of substitution, with one or more substitutent group. The phrase should not be interpreted as duplicative of the substitutions herein described and depicted. Exemplary optional substituent groups include acyl, alkyl, alkylsulfonyl, alkoxy, alkoxycarbonyl, cyano, halogen, haloalkyl, hydroxyl, oxo, and nitro.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition.

Compound Preparation

Abbreviations
AcOH acetic acid
AIBN azobisisobutyronitrile
$AlCl_3$ aluminum trichloride
aq. aqueous
Ar argon gas
$Br_2$ bromine
$CBr_4$ carbon tetrabromide
$CCl_4$ carbon tetrachloride
$CH_2Cl_2$ dichloromethane
$CH_3CN$ acetonitrile
$CH_3I$ methyl iodide
$(CH_2O)_n$ paraformaldehyde
$CH_3SO_3H$ methanesulfonic acid
conc. Concentrated
$Cs_2CO_3$ cesium carbonate
CuBr copper(I) bromide
CuCN copper(I) cyanide
CuI copper(I) iodide
$(COCl)_2$ oxalyl chloride
DCM dichloromethane
DCE 1,2-dichloroethane
DEAD Diethyl Azodicarboxylate
DIPEA N,N-diisopropylethylamine
DMAP 4-(dimethylamino)pyridine
DME 1,2-dimethoxyethane
DMF N,N-dimethylformamide
DMSO dimethylsulfoxide
EA ethyl acetate
EtOAc ethyl acetate
EDC N-(3-dimethylaminopropyl)-N'-ethylcarbodiimide hydrochloride
$Et_3N$ triethylamine
$Et_2O$ diethyl ether
EtOH ethanol
$FeSO_4$ iron(II) sulfate
h hour(s)
$H_2$ hydrogen gas
HATU O-(7-azabenzotriazol-1-yl)-N,N,N',N'-tetramethyluronium hexafluorophosphate
HBr hydrobromic acid
HCl hydrochloric acid
$H_2O$ water
$HNO_3$ nitric acid
HOBt hydroxybenzotriazole
HPLC high-performance liquid chromatography
$H_2SO_4$ sulfuric acid
$I_2$ iodine
i-PrMgCl isopropylmagnesium chloride
$K_2CO_3$ potassium carbonate
$K_3Fe(CN)_6$ potassium ferricyanide
KOt-Bu potassium tert-butoxide
$K_3PO_4$ potassium phosphate tribasic
LCMS liquid chromatography mass spectrometry
$LiAlH_4$ lithium aluminum hydride
LiOH lithium hydroxide
m-CPBA meta-chloroperbenzoic acid
MeMgBr methyl magnesium bromide
MeOH methanol
Mg magnesium
$MgCl_2$ magnesium chloride
min minute(s)
$MnO_2$ manganese dioxide
$N_2$ nitrogen gas
$NaBH_4$ sodium borohydride
NaCN sodium cyanide
$Na_2CO_3$ sodium carbonate
NaH sodium hydride
$NaHCO_3$ sodium bicarbonate
$NaHSO_3$ sodium bisulfite
$NaN_3$ sodium azide
NaOH sodium hydroxide
$Na_2SO_4$ sodium sulfate NBS N-Bromosuccinimide
n-BuLi n-butyllithium
$NH_4Cl$ ammonium chloride
NMM N-methylmorpholine
PCC pyridinium chlorochromate
PE petroleum ether
Pd/C palladium on carbon
$Pd(dppf)Cl_2$ [1,1'-bis(diphenylphosphino)ferrocene]dichloropalladium(II)
$Pd(PPh_3)_4$ tetrakis(triphenylphosphine)palladium(0)
$PhNO_2$ nitrobenzene
$POCl_3$ phosphoryl chloride
$PPh_3$ triphenylphosphine
p-TsOH para-toluene sulfonic acid
Rf retention factor
rt room temperature
Rt retention time
$SOCl_2$ thionyl chloride
TFA trifluoroacetic acid
TFAA trifluoroacetic anhydride
THF tetrahydrofuran
TLC thin layer chromatography
®T3P 2,4,6-tripropyl-1,3,5,2,4,6-trioxatriphosphorinane 2,4,6-trioxide
Zn zinc powder Generic Synthesis Schemes The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention. Starting materials are commercially available or are made from commercially available starting materials using methods known to those skilled in the art.

The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep or ISCO Gold silica gel cartridges (4 g-330 g), or an Analogix IF280 instrument with SF25 silica gel cartridges (4 g-3-00 g), or a Biotage SP1 instrument with HP silica gel cartridges (10 g-100 g). Purification by reverse phase HPLC was conducted using a YMC-pack column (ODS-A 75×30 mm) as solid phase, unless otherwise noted. A mobile phase of 25 mL/min A (acetonitrile-0.1% TFA):B (water-0.1% TFA), 10-80% gradient A (10 min) was utilized with UV detection at 214 nM, unless otherwise noted.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax ($C_8$) with a 3.5 um particle size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50× 4.6 mm, 1.8 μm) eluting with $CH_3CN$: ammonium acetate buffer. The reactions were performed in the microwave (CEM, Discover).

$^1$H-NMR spectra were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal. All NMRs in DMSO unless otherwise noted.

Analytical HPLC: Products were analyzed by Agilent 1100 Analytical Chromatography system, with 4.5×75 mm Zorbax XDB-C18 column (3.5 um) at 2 mL/min with a 4 min gradient from 5% CH$_3$CN (0.1% formic acid) to 95% CH$_3$CN (0.1% formic acid) in H$_2$O (0.1% formic acid) and a 1 min hold.

The compounds of formula (I) can be made according to Scheme 1 or analogous methods. Reductive amination of compound (1) afforded the various amine analogs (2), which was hydrolyzed under NaOH to make carboxylic acid compound (3). Amide formation between compound (3) and intermediate (4) under EDC and HOAT afforded compound (5), which underwent Suzuki coupling to afford the example compounds (6).

Scheme 1: Generic Synthesis of Examples of Formula (I)

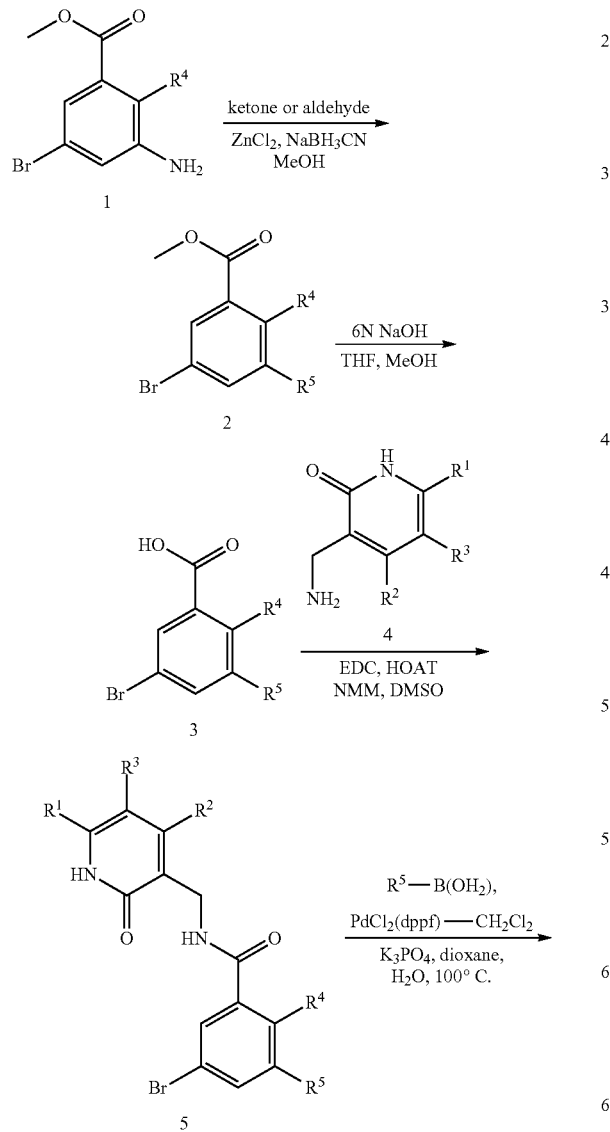

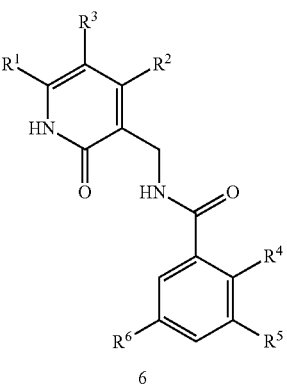

Alternatively, Examples can be made following Scheme 2. Compound (7) can be made from compound (1) under Sandmeyer reaction condition. Compound (7) underwent substitution and hydrolysis to afford compound (8), which was coupled with compound (4) under EDC and HOAT to form compound (9). Example compound (10) can be obtained by Suzuki reaction of compound (9) with corresponding boric acid.

Scheme 2: Alternative Synthesis of Examples of Formula (I)

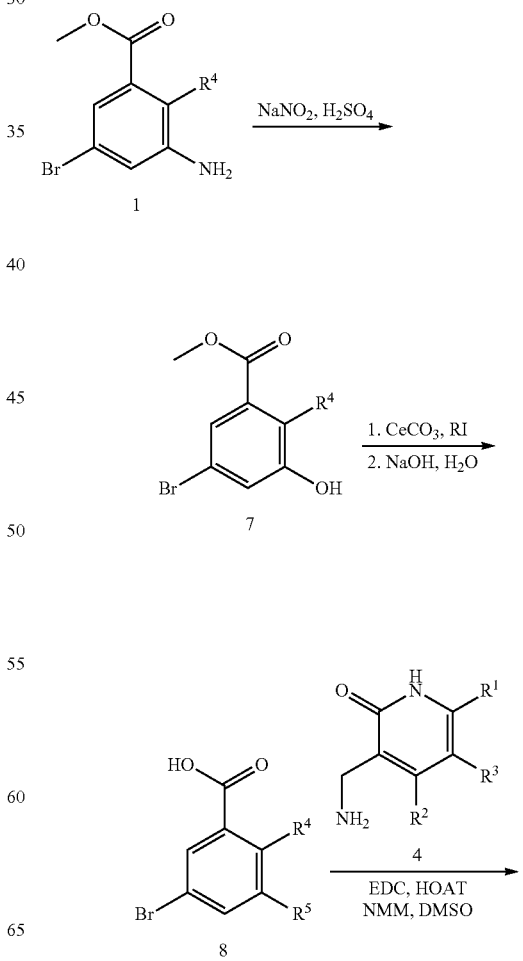

-continued

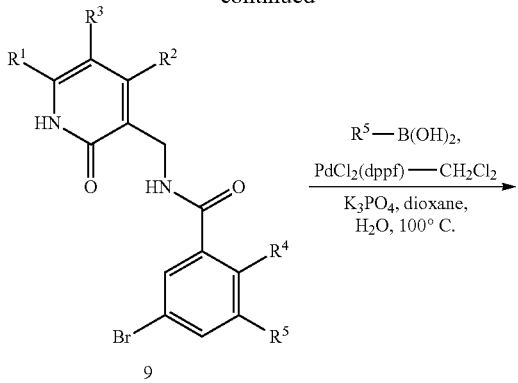

Preparation of Intermediates

Intermediate 1

3-(Aminomethyl)-4,6-dimethyl-2(1H)-pyridinone hydrochloride

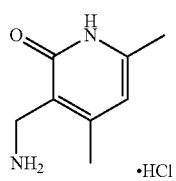

Palladium on carbon (10%) (3.24 g) was charged into a 2 L dry Parr bottle and a small amount of acetic acid was added. Next added 4,6-dimethyl-2-oxo-1,2-dihydro-pyridine-3-carbonitrile (30 g, 202.7 mmol), sodium acetate (30.75 g, 375.0 mmol), platinum oxide (0.218 g), and acetic acid (1 L). The bottle was capped, placed on Parr apparatus, and shaken under an atmosphere of H2 (100 psi) for 2 days. The reaction mixture was filtered. The solvent was removed to give a residue, which was treated with 150 mL of conc. HCl, and the formed solids were filtered. The yellow filtrate was concentrated. To the crude compound was added 30 mL of conc. HCl and 150 mL EtOH, the contents cooled to 0° C., and stirred at 0° C. for 2 h. The formed solids were filtered, washed with cold EtOH, ether, and dried. The product was collected as 36 g. This batch was combined with other batches prepared on smaller scales and triturated with ether to give 51 g of pure compound. 1H NMR (400 MHz, DMSO-d6) δ ppm 11.85 (br s, 1H) 8.13 (br s, 3H) 5.93-6.01 (m, 1H) 3.72-3.80 (m, 2H) 2.22 (s, 3H) 2.16 (s, 3H).

Intermediate 2

3-(Aminomethyl)-6-methyl-4-(trifluoromethyl)-2 (1H)-pyridinone

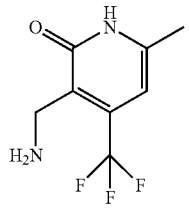

To a dried 500 mL Parr bottle equipped with nitrogen inlet were added sodium acetate (1.502 g, 18.30 mmol), 10% palladium on carbon (1.579 g, 0.742 mmol), platinum(IV) oxide (0.011 g, 0.049 mmol) and a small amount of acetic acid to wet the catalysts, under nitrogen stream. Next was added 2-hydroxy-6-methyl-4-(trifluoromethyl)-3-pyridinecarbonitrile (2.0 g, 9.89 mmol) followed by acetic acid (175 mL) while under nitrogen atmosphere. The contents were sealed, placed on a Parr shaker, and reacted at 40 psi of H2 for ca. 6 hr, keeping the H2 psi between 20 and 40 psi (vessel was refilled twice). The vessel was purged with nitrogen and the reaction mixture filtered through Celite, and the filter pad was further washed with a small amount of acetic acid. The volatiles were removed in vacuo to afford a residue, which was dried under high vacuum for 45 min The solid was suspended in conc. HCl (12 mL), stirred, and filtered. The clear filtrate was concentrated in vacuo and the residue dried under high vacuum. The collected solid was suspended in conc. HCl (2 mL) and diluted with EtOH (13 mL). The contents were agitated and stored at ca. 0° C. (freezer) for 30 min to give a white solid. The solid was filtered and washed with cold ethanol (5 mL). The solid was filtered and dried in vacuum oven for 1 h to give 3-(aminomethyl)-6-methyl-4-(trifluoromethyl)-2(1H)-pyridinone (0.95 g, 40%). LCMS E-S(M+H)=206.9. $^1$H NMR (400 MHz, DMSO-d$_6$) δ ppm 2.31 (s, 3H), 3.40-3.62 (m, 2H), 3.87 (d, J=5.05 Hz, 2H), 8.12-8.37 (m, 3H).

Intermediate 3

3-(Aminomethyl)-4-cyclohexyl-6-methyl-2(1H)-pyridinone

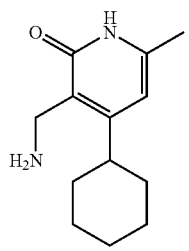 [SMILES: Cc1cc(C2CCCCC2)c(CN)c(=O)[nH]1]

3a) 4-Cyclohexyl-6-methyl-2-oxo-1,2-dihydro-3-pyridinecarbonitrile

To a stirred suspension of CrCl₂ (58 g, 472.8 mmol) in THF (1500 mL) was added a THF solution (500 mL) of 1,1-dichloro-2-propanone (10 g, 78.8 mmol) and cyclohexanecarbaldehyde (8.84 g, 78.8 mmol). The reaction mixture was heated at reflux for 2 h, and then quenched by the addition of 1.0 M HCl. The reaction mixture was filtered through a pad of Celite and concentrated in vacuo. The crude residue (10 g) was added to a solution of DMSO (150 mL) containing t-BuOK (7.5 g, 65.7 mmol) and cyanoacetamide (6.1 g, 72.3 mmol) and stirred at room temperature for 30 min Additional t-BuOK (22.5 g, 197.1 mmol) was added and the reaction mixture was stirred under an atmosphere of oxygen for an additional 1 h. The contents were purged with argon, diluted with 4 volumes of H₂O, and then 5 volumes of 4 N HCl, which were added slowly. The reaction mixture was filtered, washed with water and dried to give 4-cyclohexyl-6-methyl-2-oxo-1,2-dihydro-3-pyridinecarbonitrile (4.5 g, 32%). ¹H NMR (400 MHz, DMSO-d₆) δ ppm 6.25 (s, 1H), 2.61-2.65 (m, 1H), 2.22 (s, 3H), 1.66-1.79 (m, 4H), 1.24-1.46 (m, 6H).

3b) 3-(Aminomethyl)-4-cyclohexyl-6-methyl-2(1H)-pyridinone

To an ice-bath cooled THF (100 mL) solution of the product from step 1 (2 g, 9.26 mmol) was added NaBH₄ (0.81 g, 21.3 mmol) and I₂ (2.3 g, 9.26 mmol), and the mixture stirred for 30 min The reaction mixture was then heated at reflux for 3 h, and then allowed to cool to room temperature. After cooling to 0° C., the reaction mixture was acidified by slow addition of 3 N HCl (1 mL). The reaction mixture was concentrated in vacuo and the crude product purified by reverse phase HPLC to give 3-(aminomethyl)-4-cyclohexyl-6-methyl-2(1H)-pyridinone as a solid (0.5 g, 25%). LCMS E-S(M+H)=221.1. ¹H NMR (400 MHz, DMSO-d₆) δ ppm 11.8-11.9 (br s, 1H), 7.80-7.93 (br s, 3H), 6.07 (s, 1H), 3.69 (s, 2H), 2.67-2.75 (m, 1H), 2.17 (s, 3H), 1.58-1.72 (m, 5H), 1.19-1.41 (m, 5H).

Intermediate 4

3-(Aminomethyl)-4-cyclopropyl-6-methyl-2(1H)-pyridinone

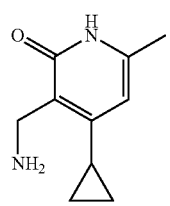

The title compound was prepared in the same manner as described for 3-(aminomethyl)-4-cyclohexyl-6-methyl-2(1H)-pyridinone (Intermediate 3) using 4-cyclopropyl-6-methyl-2-oxo-1,2-dihydro-3-pyridinecarbonitrile (5 g, 28.7 mmol). Obtained: 0.50 g (10%). LCMS E-S(M+H)=179.1. ¹H NMR (400 MHz, DMSO-d₆) δ ppm 11.76-11.78 (br s, 1H), 7.82-7.92 (br s, 3H), 5.61 (s, 1H), 3.94-3.99 (m, 2H), 2.11 (s, 3H), 1.98-2.05 (m, 1H), 0.95-1.01 (m, 2H), 0.74-0.79 (m, 2H).

Intermediate 5

3-(Aminomethyl)-6-methyl-4-propyl-2(1H)-pyridinone

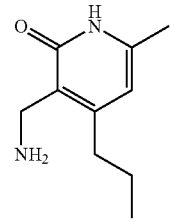

5a) 6-Methyl-2-oxo-4-propyl-1,2-dihydro-3-pyridinecarbonitrile

To a solution of DMSO (300 mL) containing t-BuOK (20 g, 178 mmol) and cyanoacetamide (16.5 g, 196 mmol) was added (3E)-3-hepten-2-one (20 g, 178 mmol), and the contents were stirred at room temperature for 30 min Additional t-BuOK (60 g, 534 mmol) was added and the reaction mixture was placed under an atmosphere of oxygen for an additional 1 h. The reaction mixture was purged with argon, diluted with 4 volumes of H₂O, and then 5 volumes of 4 N HCl, which were added slowly. The reaction mixture was filtered, washed with water, and dried to give 6-methyl-2-oxo-4-propyl-1,2-dihydro-3-pyridinecarbonitrile (10 g, 32%). ¹H NMR (400 MHz, DMSO-d₆) δ ppm 12.25-12.40 (br s, 1H), 6.18 (s, 1H), 2.53 (t, 2H), 2.22 (s, 3H), 1.57-1.64 (m, 2H), 0.84 (t, 3H).

5b) 3-(Aminomethyl)-6-methyl-4-propyl-2(1H)-pyridinone

The title compound was prepared in the same manner as described for 3-(aminomethyl)-4-cyclohexyl-6-methyl-2(1H)-pyridinone (Intermediate 3) using 6-methyl-2-oxo-4-propyl-1,2-dihydro-3-pyridinecarbonitrile (2 g, 11.2 mmol). Obtained: 1.2 g (60%). LCMS E-S(M+H)=181.1. ¹H NMR (400 MHz, DMSO-d₆) δ ppm 7.85-7.95 (br s, 3H), 5.99 (s, 1H), 3.80-3.85 (m, 2H), 2.42 (t, 2H), 2.14 (s, 3H), 1.43-1.49 (m, 2H), 0.86 (t, 3H).

Intermediate 6

3-(Aminomethyl)-6-methyl-4-phenyl-2(1H)-pyridinone

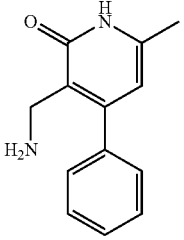 [SMILES: Cc1cc(-c2ccccc2)c(CN)c(=O)[nH]1]

The title compound was prepared in the same manner as described for 3-(aminomethyl)-6-methyl-4-propyl-2(1H)- pyridinone (Intermediate 5) using (3E)-4-phenyl-3-buten-2-one (20 g, 137 mmol). LCMS E-S(M+H)=215.0. $^1$H NMR (400 MHz, DMSO-$d_6$) δ ppm 12.2-12.3 (br s, 1H), 7.88-8.00 (br s, 3H), 7.43-7.51 (m, 3H), 7.29-7.38 (m, 2H), 6.08 (s, 1H), 3.67-3.70 (m, 2H), 2.23 (s, 3H).

Intermediate 7

3-(Aminomethyl)-6-methyl-4-(1-methylethyl)-2(1H)-pyridinone

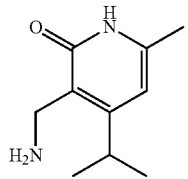

The title compound was prepared in the same manner as described for 3-(aminomethyl)-6-methyl-4-propyl-2(1H)-pyridinone (Intermediate 5) using (3E)-5-methyl-3-hexen-2-one (20 g, 137 mmol). LCMS E-S(M+H)=181.1. $^1$H NMR (400 MHz, DMSO-$d_6$) δ ppm 11.8-11.9 (br s, 1H), 7.86-7.96 (br s, 3H), 6.10 (s, 1H), 3.82-3.86 (m, 2H), 3.02-3.09 (m, 1H), 2.17 (s, 3H), 1.08 (d, 6H).

Intermediate 8

3-(Aminomethyl)-4-methyl-6-propyl-2(1H)-pyridinone

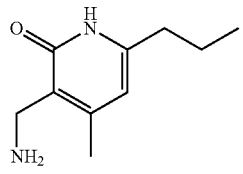

8a) 4-Methyl-2-oxo-6-propyl-1,2-dihydro-3-pyridinecarbonitrile

To a solution of NaNH$_2$ (32.5 g, 862 mmol) in anhydrous ether (500 mL) at 30° C. was added dropwise a mixture of butyric acid ethyl ester (50 g, 431 mmol) and acetone (37.5 g, 646.5 mol). After addition, the reaction mixture was stirred for 4 h. The reaction mixture was poured onto ice water with stirring. Additional ether was added, and the layers were separated. The aqueous layer was acidified to pH 5.0 with 2 N HCl and then to pH 7.5 with Na$_2$CO$_3$. The aqueous layer was then extracted with ether. The combined organic layers were dried over Na$_2$SO$_4$, filtered, and concentrated in vacuo. The crude product, 2,4-heptanedione (20 g, 156 mmol), and 2-cyanoacetamide (13.12 g, 156 mmol) were suspended in EtOH (160 mL) at 75° C., followed by addition of piperidine (13.2 g, 156 mmol). The contents were stirred and heated at reflux for 1 h. The mixture was cooled to room temperature and filtered. The collected solid was suspended in water and stirred for 1 h. The mixture was filtered and dried to give 4-methyl-2-oxo-6-propyl-1,2-dihydro-3-pyridinecarbonitrile (11 g, 40%). LCMS E-S(M+H)=181.1. $^1$H NMR (400 MHz, DMSO-$d_6$) δ ppm 12.3-12.4 (br s, 1H), 6.25 (s, 1H), 3.64 (s, 3H), 2.50 (t, 2H), 1.63 (m, 2H), 0.94 (t, 3H).

8b) 3-(Aminomethyl)-4-methyl-6-propyl-2(1H)-pyridinone

Sodium acetate (3.5 g, 42.6 mmol), palladium on carbon (0.81 g) and platinum oxide (0.1 g) were placed in a dried Parr bottle flushed with nitrogen, followed by addition of a small amount of acetic acid (to wet the catalysts). A solution of 4-methyl-2-oxo-6-propyl-1,2-dihydro-pyridine-3-carbonitrile (5 g, 28 mmol) in acetic acid was added to the Parr bottle followed by additional acetic acid (200 mL). The vessel was capped, placed on Parr apparatus and hydrogenated at 45 psi for 12 h. The reaction mixture was filtered and the filtrate concentrated in vacuo. The crude product was purified by preparative HPLC to afford the title compound (TFA salt) as 4.1 g (87%). LCMS E-S(M+H))=181.1. $^1$H NMR (400 MHz, DMSO-$d_6$) δ ppm 11.8-11.9 (br s, 1H), 7.83-7.88 (br s, 3H), 5.99 (s, 1H), 3.77-3.81 (m, 2H), 2.37 (t, 2H), 1.53 (m, 2H), 0.83 (t, 3H).

Intermediate 9

3-(Aminomethyl)-6-cyclopropyl-4-methyl-2(1H)-pyridinone hydrochloride

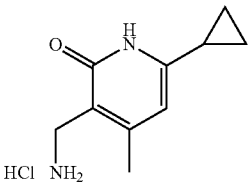

9a) 1-Cyclopropyl-1,3-butanedione

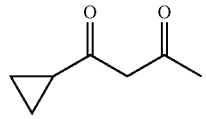

To a stirring solution of THF (100 mL) was added potassium tert-butoxide (5.60 g, 49.5 mmol), followed by a mixture of cyclopropyl methyl ketone (3.27 mL, 33 mmol) and ethyl acetate (9.69 mL, 99 mmol) in 30 mL THF at 35° C., via addition funnel over a 25 min period. The contents were heated and stirred at 60° C. After 3 h, the contents were removed from heating, and allowed to cool to room temperature. The reaction mixture was carefully diluted with 30 mL 2 N HCl and stirred for 10 min The mixture was extracted with diethyl ether (3×50 mL), and the combined organic layers washed with brine (1×50 mL). The organic layer was dried over MgSO$_4$, filtered, and concentrated in vacuo. Purification by chromatography on silica gel (eluent: 0 to 15% EtOAc in hexanes) with good separation afforded 1-cyclopropyl-1,3-butanedione as a light yellow colored oil, 3.9 g in ~75% purity (residual solvent), for an overall yield of 70%. $^1$H NMR (400 MHz, CDCl$_3$) δ ppm 0.89-0.96 (m, 2H), 1.09-1.15 (m, 2H), 1.59-1.69 (m, 1H), 2.04 (s, 3H), 5.63 (s, 1H), 15.5-16.0 (br s, 1H).

9b) 6-Cyclopropyl-4-methyl-2-oxo-1,2-dihydro-3-pyridinecarbonitrile

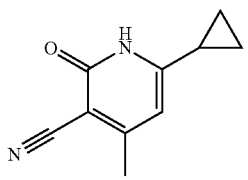

To a stirred solution of ethanol (5 mL) were added 1-cyclopropyl-1,3-butanedione (505 mg, 3.00 mmol) and cyanoacetamide (252 mg, 3.00 mmol), and the heterogenous contents heated until homogenous (ca. 75° C.). Piperidine was added (0.395 mL, 4.00 mmol) and the mixture was heated at reflux for 30 min The reaction mixture was allowed to cool to room temperature, wherein precipitation ensued. The solid precipitate was filtered and set aside. The filtrate was concentrated in vacuo and the oily residue treated with minimal EtOAc and then 10 mL hexanes to afford a second crop of solid. The solid product crops were combined, suspended in water (7 mL), vigorously stirred, and vacuum filtered to afford 6-cyclopropyl-4-methyl-2-oxo-1,2-dihydro-3-pyridinecarbonitrile as a nearly white solid (380 mg, 73%). LCMS E-S(M+H)=175.1. $^1$H NMR (400 MHz, CDCl$_3$) δ ppm 1.01-1.09 (m, 2H), 1.28 (dd, J=8.59, 2.27 Hz, 2H), 1.95-2.01 (m, 1H), 2.43 (s, 3H), 5.82 (s, 1H).

9c) 1,1-Dimethylethyl [(6-cyclopropyl-4-methyl-2-oxo-1,2-dihydro-3-pyridinyl)methyl]carbamate

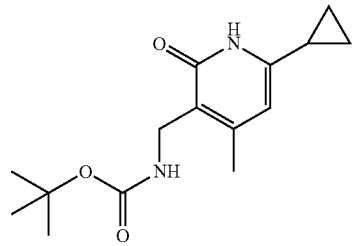 [SMILES: Cc1cc(C2CC2)[nH]c(=O)c1CNC(=O)OC(C)(C)C]

6-Cyclopropyl-4-methyl-2-oxo-1,2-dihydro-3-pyridinecarbonitrile (0.35 g, 2.01 mmol) was added to methanol (20 mL) and the stirred contents cooled to −10° C. Next was added di-tert-butyloxycarbonyl (0.933 mL, 4.02 mmol) and the suspension stirred for 15 min Next was added in NiCl$_2$·6H$_2$O (0.055 g, 0.201 mmol) as a solid and stirred for 5 min Then NaBH$_4$ (0.532 g, 14.06 mmol) was added in 6 portions with 5 min increments between each portion. Then the ice bath was removed and the contents were stirred with warming to room temperature overnight. The reaction mixture was returned to −10° C., followed by addition of 3 more portions of NaBH$_4$ (0.532 g, 14.06 mmol). The ice bath was removed and the mixture stirred at room temperature for 1 h. The contents were quenched by addition of diethylethylene amine (0.218 mL, 2.01 mmol) and stirred for 45 min at room temperature. The volatiles were removed in vacuo and the residue suspended in EtOAc and saturated NaHCO$_3$. The organic layer was washed with additional NaHCO$_3$. The layers were separated, and the organic layer dried over MgSO$_4$, filtered, and concentrated in vacuo. The crude product was purified by silica gel chromatography (eluent: 10% methanol in dichloromethane). The collected product was dried under hi-vacuum for 1 h, and then treated with ether and filtered. After drying in vacuum oven at 45° C. for 2 h, 1,1-dimethylethyl[(6-cyclopropyl-4-methyl-2-oxo-1,2-dihydro-3-pyridinyl)methyl]carbamate was collected (0.28 g, 50%). $^1$H NMR (400 MHz, DMSO-d$_6$) δ ppm 0.73-0.80 (m, 2H), 0.88-0.96 (m, 2H), 1.36 (s, 9H), 1.70-1.82 (m, 1H), 2.11 (s, 3H), 3.95 (d, J=5.31 Hz, 2H), 5.66 (s, 1H), 6.51 (t, J=4.80 Hz, 1H), 11.50 (br. s., 1H).

9d) 3-(Aminomethyl)-6-cyclopropyl-4-methyl-2(1H)-pyridinone hydrochloride 1,1-Dimethylethyl[(6-cyclopropyl-4-methyl-2-oxo-1,2-dihydro-3-pyridinyl)methyl]carbamate (0.28 g, 1.006 mmol) was added to EtOAc (9 mL) and methanol (1.0 mL). The suspension was stirred at room temperature for 5 min, followed by addition of 4 M HCl in dioxane (5.03 mL, 20.12 mmol), and the contents were stirred at room temperature overnight. The volatiles were then removed in vacuo to afford a solid. The solid was triturated with ether, filtered, and dried in a vacuum oven at 45° C. for 4 h. The title compound was collected (0.22 g, 100% yield). $^1$H NMR (400 MHz, DMSO-d$_6$) δ ppm 0.78-0.86 (m, 2H), 0.95-1.03 (m, 2H), 1.83 (tt, J=8.46, 5.05 Hz, 1H), 2.16-2.22 (m, 3H), 3.75 (q, J=5.47 Hz, 2H), 5.79 (s, 1H), 8.02 (br. s., 3H), 11.92 (br. s., 1H).

Intermediate 10

3-(Aminomethyl)-4-ethyl-6-methyl-2(1H)-pyridinone hydrochloride

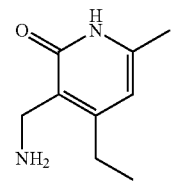

10a) Hex-3-en-2-one

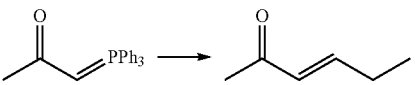

To a stirred solution of 1-(triphenylphosphoranylidene)-2-propanone (100 g, 307 mmol) in DCM (500 mL) was added propionaldehyde (140 mL, 1929 mmol) at room temperature. The reaction mixture was then stirred at room temperature for 18 hours. The reaction was monitored by TLC. The solvent (DCM) was distilled off using ordinary distillation. The residue was then distilled using fractional distillation under vacuum (~450 mbar) and the desired product was isolated. The title compound, hex-3-en-2-one (20 g, 66%), was collected at 110° C. $^1$H NMR (CDCl$_3$, 400

MHz) δ ppm 1.071-1.121 (t, 3H, J=7.4 Hz), 2.250-2.299 (m, 5H), 6.054-6.094 (d, 1H, J=16 Hz), 6.823-6.895 (m, 1H).

10b) 4-Ethyl-1,2-dihydro-6-methyl-2-oxopyridine-3-carbonitrile

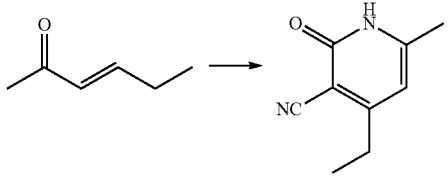

To a stirred solution of t-BuOK (22.85 g, 204.08 mmol) and cyanoacetamide (18.8 g, 224.1 mmol) in DMSO (300 mL) was added hex-3-en-2-one (20 g, 204.08 mmol) under argon atmosphere at room temperature. The reaction mixture was then stirred at room temperature for 30 min and then added additional t-BuOK (68.5 g, 612.05 mmol) was added. Argon gas was displaced by oxygen gas and the mixture stirred for 48 hrs at room temperature in presence of oxygen. Reaction was monitored by TLC. The reaction mixture was cooled to 0° C. and diluted with water (100 mL) followed by 4 N HCl (120 mL). The mixture was stirred for 15 min and the resulting solid was filtered. The solid was washed with water (1 L) and dried to afford the title compound, 4-ethyl-1,2-dihydro-6-methyl-2-oxopyridine-3-carbonitrile (10.5 g, 31%), as an off white solid. $^1$H NMR (CDCl$_3$, 400 MHz): δ ppm 1.148-1.185 (t, 3H, J=7.4 Hz), 2.237 (s, 3H), 2.557-2.614 (m, 2H), 6.211 (s, 1H), 12.330 (broad s, 1H). MS(ES) [M+H]$^+$ 161.06.

10c) 3-(Amino methyl)-4-ethyl-6-methylpyridin-2(1H)-one

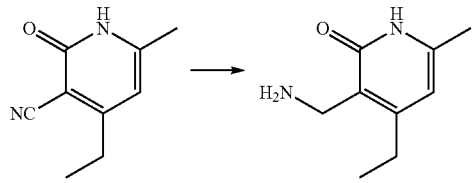

To a suspension of Raney Nickel (6 g) in methanol (200 mL) was added 4-ethyl-1,2-dihydro-6-methyl-2-oxopyridine-3-carbonitrile (10 g, 61.7 mmol) and methanolic ammonia (750 mL). The reaction mixture was stirred at room temperature under hydrogen pressure (80 psi) for 48 hrs. The reaction mixture was filtered through Celite and washed with methanol (250 mL). The filtrate was concentrated under reduced pressure and the residue purified by filter column using silica gel (60-120 mesh), eluted with 10% MeOH in CHCl$_3$, to afford 3-(amino methyl)-4-ethyl-6-methylpyridin-2(1H)-one (5.6 g, 54%) as an off white solid. $^1$H NMR (DMSO-D$_6$, 400 MHz) (free amine): δ ppm 1.063-1.101 (t, 3H, J=7.6 Hz), 2.101 (s, 3H), 2.412-2.449 (m, 2H), 3.448 (s, 2H), 5.835 (s, 1H). MS(ES) [M+H]$^+$ 167.06.

10d) 3-(Aminomethyl)-4-ethyl-6-methylpyridin-2(1H)-one hydrochloride

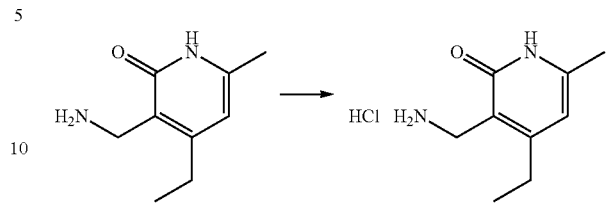

3-(Amino methyl)-4-ethyl-6-methylpyridin-2(1H)-one, (5.6 g, 33 mmol) was suspended in DCM (560 mL) and the insoluble contents/particles were filtered. The filtrate was concentrated and dried. The residue was dissolved in DCM (10 mL) and 4 M HCl in 1,4-dioxane (16 mL, 66 mmol) was added at 0° C. and stirred for 10 min, at which time the reaction mixture was concentrated under high-vacuum and dried. The resulting crude solid was triturated with hexane (150 mL) and filtered. The solid was dried under vacuum. Collected 3-(amino methyl)-4-ethyl-6-methylpyridin-2(1H)-one hydrochloride (5.9 g, 86%). $^1$H NMR (400 MHz, DMSO-d$_6$) δ ppm 1.082-1.120 (t, 3H, J=7.6 Hz), 2.179 (s, 3H), 2.503-2.544 (m, 2H), 3.785-3.798 (d, 2H, J=5.2 Hz), 6.024 (s, 1H), 7.985 (broad s, 2H), 11.858 (broad s, 1H). MS(ES) [M+H]$^+$ 167.2.

Intermediate 11

3-(aminomethyl)-6-ethyl-4-methyl-2(1)-pyridinone

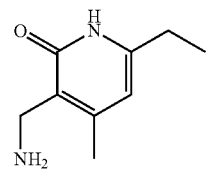

11a) 4-ethyl-6-methyl-2-oxo-1,2-dihydro-3-pyridinecarbonitrile

To a solution of t-BuOK (17.2 g, 153 mmol) and cyanoacetamide (13 g, 153 mmol) in CH$_3$CN (225 mL) was added (3E)-3-hexen-2-one (15 g, 153 mmol) at room temperature under N$_2$ atmosphere. The reaction mixture was stirred for 30 min To the reaction mixture was added additional t-BuOK (51.4 g), and the N$_2$ was displaced by oxygen. After stirring for 1 h without external cooling, the mixture was diluted with 4 N HCl, which was added slowly and with good stirring. The mixture was filtered, washed with EtOH, dried to give 6-ethyl-4-methyl-2-oxo-1,2-dihydro-3-pyridinecarbonitrile (5 g, 21%). $^1$H NMR (400 MHz, DMSO-d$_6$) δ 12.33 (br. s., 1H), 6.18 (s, 1H), 2.45 (q, 2H), 2.30 (s, 3H), 1.11 (t, 3H).

11b) 3-(aminomethyl)-6-ethyl-4-methyl-2(1H)-pyridinone

To an ice bath cooled THF solution (200 mL) of 6-ethyl-4-methyl-2-oxo-1,2-dihydro-3-pyridinecarbonitrile (7 g, 43.2 mmol) was added NaBH$_4$ (4.2 g, 108 mmol), and 12

(11.2 g, 43.2 mmol), and the contents were stirred for 30 min The reaction mixture was then heated at reflux overnight. The reaction mixture was cooled, and carefully neutralized by slow addition of 4 N HCl at 0° C. The mixture was dried over MgSO$_4$, filtered, and concentrated in vacuo. The product was purified by HPLC to give 3-(aminomethyl)-6-ethyl-4-methyl-2(1H)-pyridinone as a TFA salt (1.9 g, 26.4%). LCMS MH+=167.1 $^1$H NMR (400 MHz, DMSO-d$_6$) δ 11.82 (br. s., 1H), 7.82 (br s, 3H), 5.97 (s, 1H), 3.75-3.77 (m, 2H), 2.39 (q, 2H), 2.17 (s, 3H), 1.09 (t, 3H).

Intermediate 12

3-(aminomethyl)-6-methyl-4,4'-bipyridin-2(1H)-one

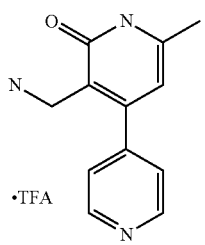 [SMILES: Cc1cc(-c2ccncc2)c(CN)c(=O)[nH]1]

12a) (2Z)-3-hydroxy-1-(4-pyridinyl)-2-buten-1-one

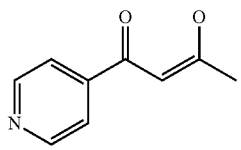

To a solution of ethyl 4-pyridinecarboxylate (30 g, 198 mmol) and acetone (34.58 g, 595 mmol) in THF (150 mL) was slowly added NaOMe (12.87 g, 238 mmol) at 35-40° C. The mixture was stirred at room temperature for 0.5 h, and then heated at reflux for 3 h. The mixture was cooled to room temperature and filtered to give a solid, which was washed with t-BuOMe, and dissolved in H$_2$O. The solution was acidified with acetic acid and the resulting oily product was extracted with CHCl$_3$. The solvent was removed in vacuo, and the crude product was obtained (12 g, 37%) and used without further purification. $^1$H NMR (400 MHz, DMSO-d$_6$) δ 8.73 (d, 2H), 7.76 (d, 2H), 6.63 (s, 1H), 2.21 (s, 3H); note: enolic OH does not appear.

12b) 6-methyl-2-oxo-1,2-dihydro-4,4'-bipyridine-3-carbonitrile and 4-methyl-6-oxo-1,6-dihydro-2,4'-bipyridine-5-carbonitrile

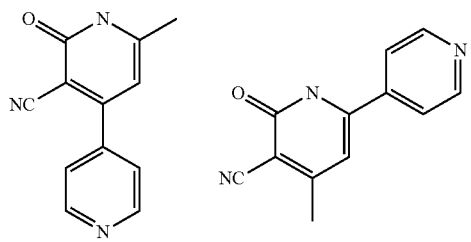 [SMILES: Cc1cc(-c2ccncc2)c(C#N)c(=O)[nH]1 ; Cc1cc(-c2ccncc2)[nH]c(=O)c1C#N]

To a solution of (2Z)-3-hydroxy-1-(4-pyridinyl)-2-buten-1-one (8 g, crude, 49 mmol) and cyanoacetamide (4.12 g, 49 mmol) in anhydrous EtOH (100 mL) was added piperidine (4.17 g, 49 mmol) under N$_2$ at 75° C. The mixture was heated at reflux for 1 h, and then cooled to room temperature. After filtration, the solid was collected and washed with H$_2$O to give the crude product (4 g) as two isomers. After separation by HPLC, 1.8 g of 6-methyl-2-oxo-1,2-dihydro-4,4'-bipyridine-3-carbonitrile and 1.2 g of 4-methyl-6-oxo-1,6-dihydro-2,4'-bipyridine-5-carbonitrile were obtained. The identity of 6-methyl-2-oxo-1,2-dihydro-4,4'-bipyridine-3-carbonitrile was established by nOE analysis. $^1$H NMR (400 MHz, DMSO-d$_6$) δ 12.79 (br. s., 1H), 8.75 (d, 2H), 7.58 (d, 2H), 6.37 (s, 1H), 2.31 (s, 3H).

12c) 3-(aminomethyl)-6-methyl-4,4'-bipyridin-2(1H)-one

To an ice bath cooled THF (100 mL) solution of 6-methyl-2-oxo-1,2-dihydro-4,4'-bipyridine-3-carbonitrile (4 g, 18.9 mmol) was added NaBH$_4$ (1.43 g, 37.9 mmol), and 12 (4.81 g, 18.9 mmol), and the mixture was stirred for 0.5 h. The reaction mixture was then heated at reflux for 4 h. After cooling to 0° C., the reaction mixture was adjusted to pH 5 with 4 N HCl. The mixture was concentrated in vacuo to give the crude compound, which was purified by HPLC to give 3-(aminomethyl)-6-methyl-4,4'-bipyridin-2(1H)-one (1.9 g, 31%) as a TFA salt. LCMS MH+=216.0 $^1$H NMR (400 MHz, DMSO-d$_6$ in D$_2$O) δ 8.87 (d, 2H), 7.87 (d, 2H), 6.13 (s, 1H), 3.65 (br s, 2H), 2.17 (s, 3H).

Intermediate 13

3-(aminomethyl)-6-cyclobutyl-4-methyl-2(1H)-pyridinone

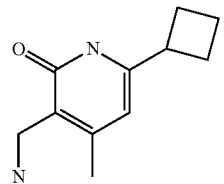

13a) Ethyl cyclobutanecarboxylate

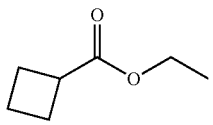

To a solution of cyclobutanecarboxylic acid (50 g, 500 mmol) in EtOH (1.2 L) was slowly added H$_2$SO$_4$ (20 mL) at room temperature. The solution was stirred at reflux overnight, and then cooled and poured into H$_2$O. The aqueous layer was extracted with ether. The combined organic layers were washed with brine, dried over Na$_2$SO$_4$, and concentrated in vacuo to give ethyl cyclobutanecarboxylate as a colorless oil (44 g, 69%). $^1$H NMR (400 MHz, CDCl$_3$-d$_3$) δ 4.04 (q, 2H), 3.04 (m, 1H), 2.12 (m, 4H), 1.88 (m, 2H), 1.18 (t, 3H).

13b) 1-cyclobutyl-1,3-butanedione

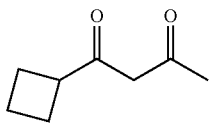

To a solution of NaNH₂ (11.7 g, 91 mmol) in anhydrous ether (150 mL) under N₂ at 30° C. was added dropwise a mixture of ethyl cyclobutanecarboxylate (19.2 g, 150 mmol) and acetone (21.75 g, 375 mmol). After addition, the reaction mixture was stirred for 4 h, then poured onto ice water with stirring. Ether was added and the unreacted components were extracted into the organic phase. The clear aqueous extract was acidified to pH 5.0 with 2 N HCl, and then to pH 7.5 with Na₂CO₃. The solution was extracted with ether. The combined organic layers were dried (Na₂SO₄), filtered, and concentrated to give the crude product of 1-cyclobutyl-1,3-butanedione (9.7 g, 76%), which was used in the next step without further purification. $^1$H NMR (400 MHz, CDCl₃-d₃) δ 5.42 (s, 1H), 3.66 (s, 1H), 2.11-2.23 (m, 4H), 2.02 (s, 3H), 1.93-1.99 (m, 2H).

13c) 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile

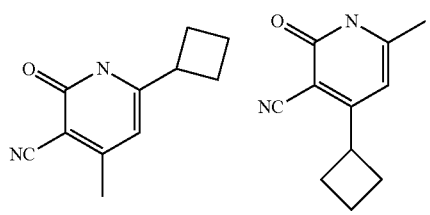

To a solution of 1-cyclobutyl-1,3-butanedione (1.5 g, 10.7 mmol) and cyanoacetamide (1.07 g, 12.8 mmol) in EtOH (25 mL) was added piperidine (1.08 g, 12.8 mmol) at 75° C. After addition, the mixture was stirred with warming to reflux. After 1 h, the mixture was cooled to room temperature during which time precipitation occurred. The contents were filtered, and the filtered solid suspended in water and stirred for 1 h. The heterogenous mixture was filtered and dried to give a mixture of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (1.14 g, 57%). $^1$H NMR (400 MHz, DMSO-d₆ in D₂O) δ 12.15-12.30 (br s, 2H), 6.39 (s, 1H), 6.34 (s, 1H), 2.40-2.28 (m, 7H), 2.23-2.25 (m, 3H), 2.18-2.21 (m, 4H), 1.99-2.11 (m, 2H), 1.84-1.90 (m, 2H).

13d) 3-(aminomethyl)-6-cyclobutyl-4-methyl-2(1H)-pyridinone and 3-(aminomethyl)-4-cyclobutyl-6-methyl-2(1H)-pyridinone

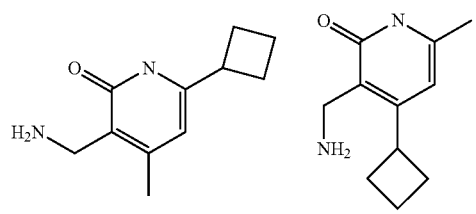

To an ice bath cooled THF (100 mL) solution of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (6 g, 32 mmol) was added NaBH₄ (2.73 g, 71.8 mmol), and 12 (8.3 g, 32 mmol), and the mixture was stirred for 30 min The reaction mixture was then heated at reflux for 3 h. After cooling to 0° C., the reaction mixture was adjusted to pH 5 with 6 N HCl. The contents were dried, filtered, and concentrated in vacuo. The crude product was purified by HPLC to give a mixture of 3-(aminomethyl)-6-cyclobutyl-4-methyl-2(1H)-pyridinone and 3-(aminomethyl)-4-cyclobutyl-6-methyl-2(1H)-pyridinone (5.6 g, 91%). $^1$H NMR (400 MHz, DMSO-d₆) δ 11.60-11.70 (br s, 2H), 7.85 (br s, 4H), 6.15 (s, 1H), 6.03 (s, 1H), 3.72-3.79 (m, 2H), 3.29-3.33 (m, 2H), 2.16 (s, 6H), 2.05-2.10 (m, 6H), 1.88-1.93 (m, 4H), 1.69-1.79 (m, 4H).

13e) 1,1-dimethylethyl [(6-cyclobutyl-4-methyl-2-oxo-1,2-dihydro-3-pyridinyl)methyl]carbamate and 1,1-dimethylethyl [(4-cyclobutyl-6-methyl-2-oxo-1,2-dihydro-3-pyridinyl)methyl]carbamate

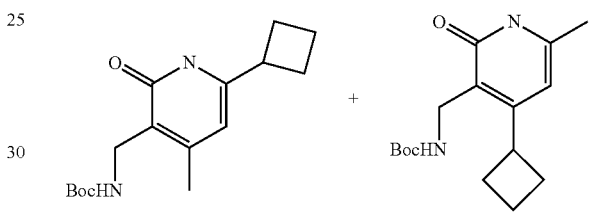

To an ice bath cooled solution of 3-(aminomethyl)-6-cyclobutyl-4-methyl-2(1H)-pyridinone and 3-(aminomethyl)-4-cyclobutyl-6-methyl-2(1H)-pyridinone (3.5 g, 18 mmol) in THF (10 mL) and DMF (10 mL) were added Boc₂O (4.68 g, 21.8 mmol) and triethylamine (5.4 g, 54 mmol). The contents were then stirred for 30 min at 30° C. The reaction was quenched by addition of ice water, during which time precipitation occurred. The reaction mixture was filtered and dried to give a mixture of the crude products. The crude products were separated by HPLC to give 1,1-dimethylethyl [(6-cyclobutyl-4-methyl-2-oxo-1,2-dihydro-3-pyridinyl)methyl]carbamate (2.1 g, 20%) and 1,1-dimethylethyl [(4-cyclobutyl-6-methyl-2-oxo-1,2-dihydro-3-pyridinyl)methyl]carbamate (1 g, 9.5%). Data for 1,1-dimethylethyl [(6-cyclobutyl-4-methyl-2-oxo-1,2-dihydro-3-pyridinyl)methyl]carbamate: $^1$H NMR (400 MHz, DMSO-d₆) δ 11.28 (br s, 1H), 6.49 (br s, 1H), 5.86 (br s, 1H), 3.85 (br s, 2H), 1.97-2.14 (m, 7H), 1.87-1.94 (m, 1H), 1.72-1.77 (m, 1H), 1.28 (s, 9H).

13f) 3-(aminomethyl)-6-cyclobutyl-4-methyl-2(1H)-pyridinone hydrochloride

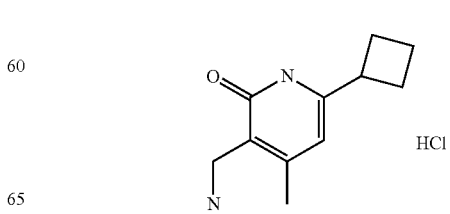

A solution of 1,1-dimethylethyl [(6-cyclobutyl-4-methyl-2-oxo-1,2-dihydro-3pyridinyl)methyl]carbamate (2.1 g, 7.2 mmol) in 4 N HCl (in 15 mL 1,4 dioxane) was heated to 60° C. for 1 h. The mixture was cooled to room temperature. The mixture was filtered and dried to give 3-(aminomethyl)-6-cyclobutyl-4-methyl-2(1H)-pyridinone as an HCl salt (1.95 g, 90%). LCMS MH+=193.1 $^1$H NMR (400 MHz, DMSO-$d_6$) δ 11.70 (br s, 1H), 8.01 (s, 3H), 6.04 (s, 1H), 3.74 (d, 2H), 3.32-3.39 (m, 1H), 2.22 (s, 3H), 2.17-2.20 (m, 2H), 2.06-2.11 (m, 2H), 1.85-1.95 (m, 1H), 1.71-1.79 (m, 1H).

Intermediate 14

3-(aminomethyl)-6-methyl-4-[(methyloxy)methyl]-2(1H)-pyridinone

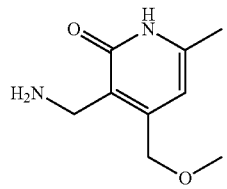

14a) 1-(methyloxy)-2,4-pentanedione

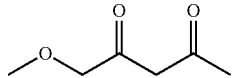

To a solution of sodium (5.83 g, 243.3 mmol) in dry toluene (62.5 mL) was added ethyl (methyloxy)acetate (24 g, 203.4 mmol) at −5° C. After stirring for 3 h, acetone (14 g, 231.4 mmol) was slowly added, upon which the mixture became brown and viscous. Next added 72 mL of tert-butyl methyl ether, and the reaction mixture was stirred at room temperature for 12 h, after which time the sodium salt precipitated. After collection and washing with additional tert-butyl methyl ether, the sodium salt was dissolved in 46 mL of 20% $H_2SO_4$. The contents were extracted with tert-butyl methyl ether and the organic layers concentrated to afford 1-(methyloxy)-2,4-pentanedione (9.76 g, 36.9%). $^1$H NMR (400 MHz, $CDCl_3$-$d_3$) δ 5.76 (s, 1H), 3.96 (s, 2H), 3.38 (s, 3H), 2.07 (s, 3H).

14b) 6-methyl-4-[(methyloxy)methyl]-2-oxo-1,2-dihydro-3-pyridinecarbonitrile

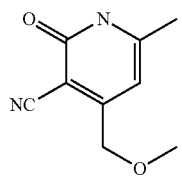

1-(methyloxy)-2,4-pentanedione (9.51 g, 73.12 mmol) and cyanoacetamide (6.17 g, 73.12 mmol) were dissolved in EtOH (76 mL) and heated until homogenous (ca. 75° C.).

Piperidine (6.25 g, 73.12 mmol) was added and the reaction mixture heated at reflux for 20 mins, followed by cooling to room temperature. The contents were filtered to give a solid which was suspended in 140 mL water and stirred vigorously for 20 min The heterogenous mixture was filtered to afford 6-methyl-4-[(methyloxy)methyl]-2-oxo-1,2-dihydro-3-pyridinecarbonitrile (7.8 g, 65.6%). LCMS MH+=179.0 $^1$H NMR (400 MHz, DMSO-$d_6$) δ 12.47 (br s, 1H), 6.26 (s, 1H), 4.40 (s, 2H), 3.29 (s, 3H), 2.25 (s, 3H).

14c) 3-(aminomethyl)-6-methyl-4-[(methyloxy)methyl]-2(1H)-pyridinone 6-methyl-4-[(methyloxy)methyl]-2-oxo-1,2-dihydro-3-pyridinecarbonitrile (1.000 g, 5.61 mmol) was suspended in acetic acid (150 ml) and the solution passed through an H-cube instrument equipped with Raney-Ni cartridge at a rate of 1 mL/min at 50 psi and 60° C. After 18 h. the acetic acid was removed under reduced pressure and the remaining residue was dissolved in MeOH. The methanolic solution was passed through a 0.2 µm teflon syringe filter. The methanolic filtrate was purified by reverse phase HPLC (Gemini 50×100 5 µm column. Run 1: 3 min, 90-10%. Run 2, 5 min 0-10%. Run 3, 10 min, 0-20%. The product fractions were concentrated to dryness on a Genevac HT-4 instrument to afford 3-(aminomethyl)-6-methyl-4-[(methyloxy)methyl]-2(1H)-pyridinone as a pale grey waxy solid (900 mg, 70.2% yield) LCMS MH+=183.0 $^1$H NMR (400 MHz, DMSO-$d_6$) δ 8.40 (br. s., 1H), 6.10 (s, 1H), 4.39 (s, 2H), 3.66 (br. s., 2H), 3.32 (s, 3H), 2.19 (s, 3H).

Intermediate 15

3-(aminomethyl)-6-methyl-4-(phenylmethyl)-2(1H)-pyridinone and 3-(aminomethyl)-4-methyl-6-(phenylmethyl)-2(1H)-pyridinone

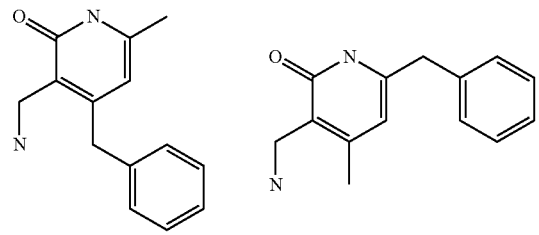 [SMILES: Cc1cc(Cc2ccccc2)c(CN)c(=O)[nH]1 ; Cc1cc(Cc2ccccc2)[nH]c(=O)c1CN]

15a) 1-phenyl-2,4-pentanedione

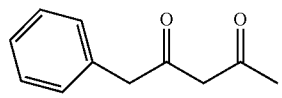

To a solution of $NaNH_2$ (19.02 g, 480 mmol) in anhydrous ether (400 mL) under $N_2$ at −5° C. was added dropwise ethyl phenylacetate (19.2 g, 150 mmol) and then acetone (21.23 g, 370 mmol) with vigorous stirring. After addition, the reaction mixture was stirred at room temperature overnight. The mixture was then acidified to pH 4.0-5.0 with 1 N HCl. The organic layer was separated and concentrated in vacuo. The crude product was purified by silica gel chromatography to give 1-phenyl-2,4-pentanedione (18.32 g, 44%). ¹H NMR (400 MHz, CDCl₃-d₃) δ 15.49 (br s, 1H), 7.33-7.45 (m, 5H), 5.53 (s, 1H), 3.66 (s, 2H), 2.10 (s, 3H).

15b) 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile

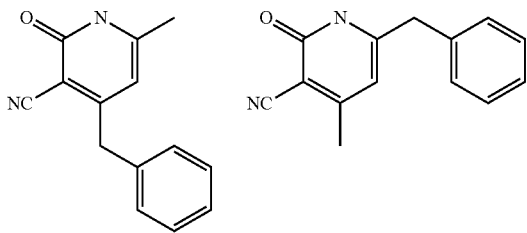 [SMILES: Cc1cc(Cc2ccccc2)c(C#N)c(=O)[nH]1 ; Cc1cc(Cc2ccccc2)[nH]c(=O)c1C#N]

1-phenyl-2,4-pentanedione (18.32 g, 104 mmol) and cyanoacetamide (8.74 g, 104 mmol) were dissolved in EtOH (104 mL) and heated until homogenous (ca. 75° C.). Piperidine (8.86 g, 104 mmol) was added and the reaction mixture heated at reflux for 15-30 min followed by cooling to room temperature, during which time precipitation occurred. The heterogenous contents were filtered to give a solid which was suspended in 200 mL water and stirred vigorously for 20 min The heterogenous mixture was filtered to afford 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (12.06 g, 52%). LCMS MH+=225.1 ¹H NMR (400 MHz, DMSO-d₆) (mixture of compounds) δ 7.21-7.31 (m, 10H), 6.06 (s, 2H), 3.89 (s, 2H), 3.79 (s, 2H), 2.24 (s, 3H), 2.15 (s, 3H).

15c) 3-(aminomethyl)-6-methyl-4-(phenylmethyl)-2(1H)-pyridinone and 3-(aminomethyl)-4-methyl-6-(phenylmethyl)-2(1H)-pyridinone

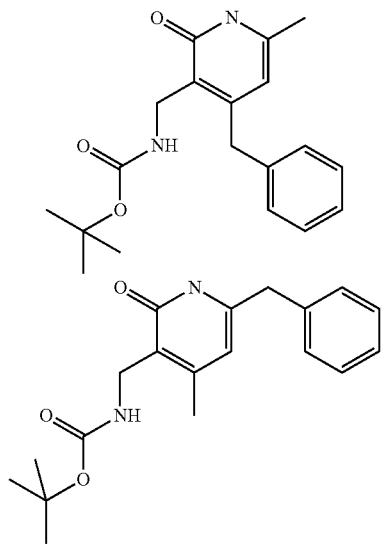

Sodium acetate (6.14 g, 74.8 mmol), Pd/C (0.65 g, 1 mmol), and platinum (II) oxide (45 mg, 1 mmol) were placed in a dried Parr bottle equipped with nitrogen inlet. A small amount of acetic acid was added to wet the catalysts. A solution of 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (6 g, 26.7 mmol) in acetic acid (300 mL) was added to the vessel. The contents were sealed and hydrogenated on Parr shaker at 45 psi for 12 h. The reaction mixture was filtered and washed with acetic acid. The filtrate was removed under reduced pressure. The residue was washed with methanol and filtered to afford a crude mixture of 3-(aminomethyl)-6-methyl-4-(phenylmethyl)-2(1H)-pyridinone and 3-(aminomethyl)-4-methyl-6-(phenylmethyl)-2(1H)-pyridinone. The reaction was run in duplicate to afford a total crude recovery of 14.5 g. To a solution of the above crude product mixture (4.0 g, 17.5 mmol) in THF (10 mL) and DMF (10 mL) was added di-tert-butoxycarbonyl anhydride (5.0 g, 23.4 mmoL) and triethylamine (5.2 g, 52.5 mmol) at 0° C. The reaction mixture was stirred with warming to room temperature and then stirred for an additional 4 h. The contents were diluted with ice water and then filtered. The collected solid was dried and the products separated by HPLC to furnish 1.2 g of 1,1-dimethylethyl {[4-methyl-2-oxo-6-(phenylmethyl)-1,2-dihydro-3-pyridinyl]methyl}carbamate (¹H NMR (400 MHz, DMSO-d₆) δ 11.55-1.60 (br s, 1H), 7.20-7.29 (m, 5H), 5.85 (s, 1H), 3.92 (s, 2H), 3.90 (s, 2H), 2.10 (s, 3H), 1.32 (s, 9H) and 1.0 g of 1,1-dimethylethyl {[6-methyl-2-oxo-4-(phenylmethyl)-1,2-dihydro-3-pyridinyl]methyl}carbamate (¹H NMR (400 MHz, DMSO-d₆) δ 11.50-11.55 (br s, 1H), 7.18-7.25 (m, 5H), 5.75 (s, 1H), 4.02 (s, 2H), 3.85 (s, 2H), 2.05 (s, 3H), 1.32 (s, 9H).

15d) 3-(aminomethyl)-4-methyl-6-(phenylmethyl)-2(1H)-pyridinone hydrochloride

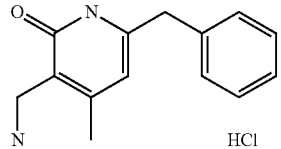 [SMILES: Cc1cc(Cc2ccccc2)[nH]c(=O)c1CN ; Cl]

A solution of 1,1-dimethylethyl {[4-methyl-2-oxo-6-(phenylmethyl)-1,2-dihydro-3-pyridinyl]methyl}carbamate (1.2 g, 3.66 mmol) in 4N HCl (in 15 mL 1,4 dioxane) was heated to 60° C. for 1 h. The mixture was cooled to room temperature. The mixture was filtered and dried to give 3-(aminomethyl)-4-methyl-6-(phenylmethyl)-2(1H)-pyridinone as an HCl salt (0.725 g, 87%). LCMS MH+=229.1 ¹H NMR (400 MHz, DMSO-d₆) δ 11.9-12.0 (br s, 1H), 7.99 (br s, 3H), 7.20 (s, 5H), 5.97 (s, 1H), 3.72-3.75 (m, 4H), 2.17 (s, 3H).

15e) 3-(aminomethyl)-6-methyl-4-(phenylmethyl)-2(1H)-pyridinone hydrochloride

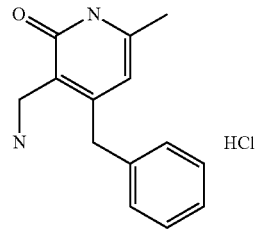 [SMILES: Cc1cc(Cc2ccccc2)c(CN)c(=O)[nH]1 ; Cl]

A solution of 1,1-dimethylethyl {[6-methyl-2-oxo-4-(phenylmethyl)-1,2-dihydro-3-pyridinyl]methyl}carbamate (1.0 g, 3.0 mmol) in 4N HCl (in 15 mL 1,4 dioxane) was heated to 60° C. for 1 h. The mixture was cooled to room temperature. The mixture was filtered and dried to give 3-(aminomethyl)-6-methyl-4-(phenylmethyl)-2(1H)-pyridinone as an HCl salt (0.600 g, 86%). LCMS MH+=229.1 $^1$H NMR (400 MHz, DMSO-$d_6$) δ 11.9-12.0 (br s, 1H), 8.03 (br s, 3H), 7.16-7.30 (m, 5H), 5.84 (s, 1H), 3.91 (s, 2H), 3.81 (s, 2H), 2.10 (s, 3H).

Intermediate 16

3-(aminomethyl)-6-methyl-4-(4-morpholinylmethyl)-2(1H)-pyridinone

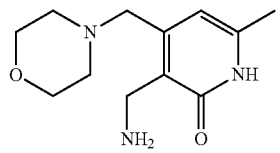

a) 5-(4-morpholinyl)-3-pentyn-2-one

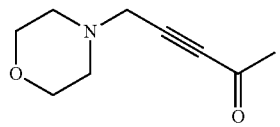

To a cooled (−40° C., CH$_3$CN/CO$_2$) solution of 4-(2-propyn-1-yl)morpholine (2.2 g, 17.58 mmol) in THF (5 mL) was added dropwise via. syringe under N$_2$ a solution of 2 M isopropylmagnesium chloride in THF (10 mL, 20.00 mmol). The reaction was stirred for 1 hr then a solution of N-methoxy-N-methylacetamide (2.2 mL, 20.69 mmol) in THF (5 mL) was added in one portion. The reaction was stirred for 2 hr (allowed to slowly warm to RT), quenched with aq. NH$_4$Cl, extracted with EtOAc, washed with brine, dried (Na$_2$SO$_4$), filtered and evaporated to dryness in vacuum. The remaining was purified by silica gel chromatography (Analogix, SF25-60 g, 0 to 80% EtOAc in hexanes). The pure fractions were combined and evaporated to dryness to give the product 5-(4-morpholinyl)-3-pentyn-2-one (2.09 g, 12.50 mmol, 71.1% yield) as a yellow oil. $^1$H NMR (400 MHz, DMSO-$d_6$) δ 3.62-3.57 (m, 4H), 3.56 (s, 2H), 2.49-2.43 (m, 4H), 2.34 (s, 3H). MS(ES)+ m/e 168.0 [M+H]$^+$.

b) 6-methyl-4-(4-morpholinylmethyl)-2-oxo-1,2-dihydro-3-pyridinecarbonitrile

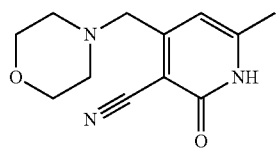 [SMILES: Cc1cc(CN2CCOCC2)c(C#N)c(=O)[nH]1]

To a stirred solution of 21 wt % sodium ethoxide in EtOH (4.2 g, 12.96 mmol) in EtOH (30 mL) was added 2-cyanoacetamide (1.1 g, 13.08 mmol). The reaction was stirred for 15 min then a solution of 5-(4-morpholinyl)-3-pentyn-2-one (2.0 g, 11.96 mmol) in EtOH was added to the reaction in one portion. (The reaction quickly turned dark red.) The reaction was stirred overnight at RT, neutralized with 6 N HCl (2.17 mL, 13.02 mmol) and evaporated to dryness under vacuum. Dried under vacuum overnight. The remaining dark solid was triturated with a solution of (9:1) CH$_2$Cl$_2$, MeOH (50 mL), filtered from insoluble material, washed with (9:1) CH$_2$Cl$_2$, MeOH, and the filtrate evaporated to dryness under vacuum. The dark solid was triturated with a solution of (1:1) EtOAc in hexanes, filtered, washed with (1:1) EtOAc in hexanes, and dried under vacuum to give a brown solid (removed a lot of fast running non-polar impurities). The crude product was purified by silica gel chromatography (Analogix, SF25-60 g, 0 to 15% CH$_2$Cl$_2$/20% (5% NH$_4$OH in MeOH) in CH$_2$Cl$_2$). The pure fractions were combined, evaporated to dryness, triturated with hexanes and dried under vacuum to give the product 6-methyl-4-(4-morpholinylmethyl)-2-oxo-1,2-dihydro-3-pyridinecarbonitrile (0.90 g, 3.86 mmol, 32.3% yield) as a light tan solid.
$^1$H NMR (400 MHz, DMSO-$d_6$) δ 12.44 (br. s., 1H), 6.34 (s, 1H), 3.63-3.56 (m, 4H), 3.48 (s, 2H), 2.45-2.36 (m, 4H), 2.27 (s, 3H) MS(ES)+ m/e 234.1 [M+H]$^+$.

c) 3-(aminomethyl)-6-methyl-4-(4-morpholinylmethyl)-2(1H)-pyridinone

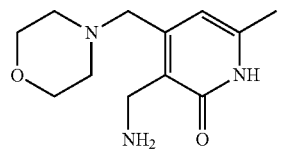 [SMILES: Cc1cc(CN2CCOCC2)c(CN)c(=O)[nH]1]

A clear solution of 6-methyl-4-(4-morpholinylmethyl)-2-oxo-1,2-dihydro-3-pyridinecarbonitrile (0.60 g, 2.57 mmol) in HOAc (20 mL) was treated on an H-Cube apparatus (50 psi, 60° C., 1 mL/min, Raney Nickel cartridge) for 18 hr overnight. LCMS showed that the reaction was complete. The reaction was evaporated to dryness, taken up in a small volume of MeOH and treated with 4 N HCl in dioxane (5 mL, 20.00 mmol). The mixture was evaporated to dryness under vacuum (began to ppt. out during evaporation), triturated with Et$_2$O, filtered and dried under vacuum to give the product 3-(aminomethyl)-6-methyl-4-(4-morpholinylmethyl)-2(1H)-pyridinone (0.76 g, 2.450 mmol, 95% yield) as a light grey solid. $^1$H NMR (400 MHz, DMSO-$d_6$) δ 6.39 (s, 1H), 4.28 (s, 2H), 3.99 (s, 2H), 3.87 (br. s., 4H), 3.27 (br. s., 4H), 2.22 (s, 3H). MS(ES)+ m/e 238.0 [M+H]$^+$ (weak), 221.3 [M+H]$^+$—NH$_3$ (strong).

Intermediate 17 tert-Butyl (5-(aminomethyl)-6-methoxy-4-methylpyridin-2-yl)carbamate

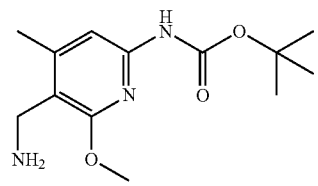 [SMILES: COc1nc(NC(=O)OC(C)(C)C)cc(C)c1CN]

a) Ethyl 4-ethoxy-2-oxopent-3-enoate

To a stirred solution of ethyl 2,4-dioxopentanoate (36.5 g, 231 mmol) and triethyl orthoformate (41 mL, 246 mmol) in ethanol (60 mL) was added ammonium chloride (3.7 g, 69 mmol). The suspension was stirred at RT overnight. LCMS showed that the reaction was mostly complete. (Hydrolyzes on LCMS to some degree?) The reaction was concentrated under vacuum. The remaining oil was taken up in $Et_2O$ (300 mL), filtered to remove insolubles, rinsed with $Et_2O$, and concentrated under vacuum. The product was obtained by short path distillation under vacuum (bp 70 to 77° C. at 0.09 mmHg) to give the product ethyl 4-ethoxy-2-oxopent-3-enoate (36.5 g, 47.3 mmol, 79% yield) as a light yellow oil. $^1$H NMR (400 MHz, CHLOROFORM-d) δ 6.24 (s, 1H), 4.32 (q, J=7.2 Hz, 2H), 4.02 (q, J=6.9 Hz, 2H), 2.41 (s, 3H), 1.41 (t, J=7.1 Hz, 3H), 1.39 (t, J=7.2 Hz, 3H). MS(ES)+ m/e 186.8 [M+H]$^+$, 208.8 M+Na$^+$.

b) ethyl 5-cyano-4-methyl-6-oxo-1,6-dihydropyridine-2-carboxylate

To a stirred solution of ethyl 4-ethoxy-2-oxopent-3-enoate (22.5 g, 121 mmol) and 2-cyanoacetamide (9.0 g, 107 mmol) in acetone (250 mL) was added potassium carbonate (15.8 g, 114 mmol). The reaction was refluxed (85° C. oil bath) for 10 hr (the reaction formed a thick ppt. in a deep red solution). The slurry was added to cold 1 N HCl (230 mL) in ice. After stirring for 30 min the suspension was filtered, washed with water and dried under vacuum to give the product ethyl 5-cyano-4-methyl-6-oxo-1,6-dihydropyridine-2-carboxylate (14.51 g, 70.4 mmol, 65.7% yield) as a light pink solid. $^1$H NMR (400 MHz, DMSO-d$_6$) δ12.60 (br. s., 1H), 7.05 (br. s., 1H), 4.34 (q, J=7.1 Hz, 2H), 2.45 (s, 3H), 1.32 (t, J=7.1 Hz, 3H). MS(ES)+ m/e 206.8 [M+H]$^+$.

c) ethyl 5-cyano-6-methoxy-4-methylpicolinate

To a stirred suspension of ethyl 5-cyano-4-methyl-6-oxo-1,6-dihydropyridine-2-carboxylate (2.0 g, 9.70 mmol) in $CH_2Cl_2$ (25 mL) was added trimethyloxonium tetrafluoroborate (2.0 g, 13.52 mmol). The reaction was rinsed down with $CH_2Cl_2$ and stirred at RT for 24 h. (The reaction eventually cleared up.) To the reaction was added 1 N NaOH (75 mL). After stirring for 10 minutes the mixture was poured into a separatory funnel. The $CH_2Cl_2$ phase was removed, dried (Na$_2$SO$_4$), filtered and concentrated under vacuum. Purification by silica gel chromatography (Analogix SF25-40 g, 50 to 100% $CH_2Cl_2$ in hexanes) gave the product ethyl 5-cyano-6-methoxy-4-methylpicolinate (1.13 g, 5.13 mmol, 52.9% yield) as a white solid. $^1$H NMR (400 MHz, DMSO-d$_6$) δ 7.75 (s, 1H), 4.37 (q, J=7.1 Hz, 2H), 4.03 (s, 3H), 2.55 (s, 3H), 1.33 (t, J=7.2 Hz, 3H). MS(ES)+ m/e 221.2 [M+H]$^+$.

d) 5-cyano-6-methoxy-4-methylpicolinic acid

To a stirred solution of ethyl 5-cyano-6-methoxy-4-methylpicolinate (1.0 g, 4.54 mmol) in MeOH (30 mL) and THF (10 mL) was added 6 N NaOH (2 mL, 12.00 mmol). The suspension was heated to 60° C. and stirred for 2 h. (The reaction cleared up right away.) LCMS indicated that the reaction was complete. The reaction was cooled to RT and concentrated to near dryness. The slurry was neutralized with 6 N HCl (2 mL) diluted with water, filtered, washed with water and dried under vacuum to give the product 5-cyano-6-methoxy-4-methylpicolinic acid (0.76 g, 3.95 mmol, 87% yield) as a white solid. $^1$H NMR (400 MHz, DMSO-d$_6$) δ13.65 (br. s., 1H), 7.73 (s, 1H), 4.03 (s, 3H), 2.54 (s, 3H). MS(ES)+ m/e 192.9 [M+H]$^+$.

e) tert-butyl (5-cyano-6-methoxy-4-methylpyridin-2-yl)carbamate

To a stirred solution of 5-cyano-6-methoxy-4-methylpicolinic acid (0.75 g, 3.90 mmol) in tert-butanol (25 mL) was added triethylamine (0.7 mL, 5.02 mmol). After the reaction became clear DPPA (1 mL, 4.64 mmol) was added dropwise over 5 minutes. The reaction was slowly heated to 100° C. and stirred for 4 h. The reaction was cooled to RT and evaporated to dryness under vacuum. Purified by silica gel chromatography (Analogix, SF25-60 g, 0 to 20% EtOAc in hexanes) to give, after trituration and filtration from hexanes, the product tert-butyl (5-cyano-6-methoxy-4-methylpyridin-2-yl)carbamate (0.61 g, 2.317 mmol, 59.4% yield) as a white solid. $^1$H NMR (400 MHz, DMSO-d$_6$) δ10.20 (s, 1H), 7.44 (s, 1H), 3.91 (s, 3H), 2.40 (s, 3H), 1.48 (s, 9H). MS(ES)+ m/e 264.0 [M+H]$^+$.

f) tert-butyl (5-(aminomethyl)-6-methoxy-4-methylpyridin-2-yl)carbamate

A clear solution of tert-butyl (5-cyano-6-methoxy-4-methylpyridin-2-yl)carbamate (0.60 g, 2.279 mmol) in HOAc (5 mL) and ethanol (20 mL) was treated on an H-Cube apparatus (50 psi, 40° C., 1 mL/min, Raney Nickel cartridge) for 18 h. LCMS showed that the reaction was complete (86% pure). The reaction was evaporated to dryness under vacuum. Purified by silica gel chromatography (Analogix, SF25-60 g, 0 to 12% (5% NH$_4$OH/MeOH) in $CH_2Cl_2$). The pure fractions were combined and evaporated to dryness under vacuum to give the product tert-butyl (5-(aminomethyl)-6-methoxy-4-methylpyridin-2-yl)carbamate (0.42 g, 1.571 mmol, 68.9% yield) as a white solid. $^1$H NMR (400 MHz, DMSO-d$_6$) δ 9.33 (s, 1H), 7.16 (s, 1H), 3.80 (s, 3H), 3.57 (s, 2H), 2.28 (s, 3H), 1.46 (s, 9H). MS(ES)+ m/e 268.1 [M+H]$^+$.

Intermediate 18

[5-(Aminomethyl)-4-methyl-6-(methyloxy)-2-pyridinyl]methanol

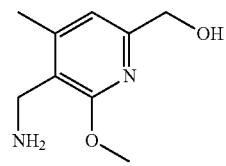

a) 6-(Hydroxymethyl)-2-methoxy-4-methylnicotinonitrile

To a stirred suspension of ethyl 5-cyano-6-methoxy-4-methylpicolinate (5.0 g, 22.70 mmol) and calcium chloride (10 g, 90 mmol) in tetrahydrofuran (50 mL) and ethanol (50.0 mL) at 0° C. in an ice bath was added sodium borohydride (2.5 g, 66.1 mmol). The reaction was slowly allowed to warm to RT and stirred for 18 h. A large amount of ppt. formed and LCMS showed that the reaction was complete. An equal volume of EtOAc was added and the reaction stirred for 1 h. The suspension was filtered through a pad of Celite and washed with EtOAc. The filtrate was transferred to a separatory funnel, washed with aq. NH₄Cl, brine, dried (Na₂SO₄), filtered and concentrated under vacuum. Purification by silica gel chromatography (Analogix, SF40-120 g, 0 to 30% EtOAc in CH₂Cl₂) gave the product 6-(hydroxymethyl)-2-methoxy-4-methylnicotinonitrile (3.75 g, 21.05 mmol, 93% yield) as a white solid. ¹H NMR (400 MHz, DMSO-d₆) δ 7.16 (s, 1H), 5.61 (t, J=5.8 Hz, 1H), 4.51 (d, J=5.8 Hz, 2H), 3.94 (s, 3H), 2.47 (s, 3H). MS(ES)+ m/e 179.1 [M+H]⁺.

b) (5-(Aminomethyl)-6-methoxy-4-methylpyridin-2-yl)methanol

A clear solution of 6-(hydroxymethyl)-2-methoxy-4-methylnicotinonitrile (0.50 g, 2.81 mmol) in HOAc (5 mL) and Ethanol (20 mL) was treated on an H-Cube apparatus (50 psi, 40° C., 1 mL/min, Raney Nickel cartridge) for 18 hr overnight. LCMS showed that the reaction was complete (crude contained 57% product and 43% dimeric side product). The reaction was evaporated to dryness under vacuum. Purified by silica gel chromatography (Analogix, SF25-40 g, 0 to 12% (5% NH₄OH in MeOH) in CH₂Cl₂) (step gradient to 8% to elute off the dimeric side product then to 12% to elute off the product). The pure fractions were combined and evaporated to dryness under vacuum to give the product (5-(aminomethyl)-6-methoxy-4-methylpyridin-2-yl)methanol (0.30 g, 1.646 mmol, 58.7% yield) as a white solid. MS(ES)+ m/e 183.1 [M+H]⁺, 166.1 [M+H]⁺—NH₃.

Intermediate 19 tert-Butyl ((5-(aminomethyl)-6-methoxy-4-methylpyridin-2-yl)methyl)carbamate

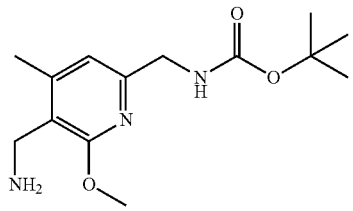 [SMILES: COc1nc(CNC(=O)OC(C)(C)C)cc(C)c1CN]

a) 6-((1,3-Dioxoisoindolin-2-yl)methyl)-2-methoxy-4-methylnicotinonitrile

To a stirred solution of 6-(hydroxymethyl)-2-methoxy-4-methylnicotinonitrile (1.50 g, 8.42 mmol), phthalimide (1.3 g, 8.84 mmol) and triphenylphosphine (2.3 g, 8.77 mmol) in tetrahydrofuran (THF) (50 mL) at 0° C. in an ice bath was added dropwise DIAD (1.8 mL, 9.26 mmol). Within minutes a white suspension formed. Additional THF (~50 mL) was added to allow stirring. The reaction was allowed to warm to RT and stirred for 3 h. LCMS showed that the reaction was complete. The reaction was evaporated to dryness under vacuum. The remaining solid was triturated with a small volume of EtOAc, filtered, washed with a small volume of EtOAc, then dried under vacuum to give the product 6-((1,3-dioxoisoindolin-2-yl)methyl)-2-methoxy-4-methylnicotinonitrile (2.12 g, 6.90 mmol, 82% yield) as a white solid. ¹H NMR (400 MHz, DMSO-d₆) δ 8.00-7.92 (m, 2H), 7.92-7.87 (m, 2H), 7.15 (s, 1H), 4.86 (s, 2H), 3.74 (s, 3H), 2.43 (s, 3H). MS(ES)+ m/e 308.2 [M+H]⁺.

b) tert-Butyl ((5-cyano-6-methoxy-4-methylpyridin-2-yl)methyl)carbamate

To a stirred fine suspension of 6-((1,3-dioxoisoindolin-2-yl)methyl)-2-methoxy-4-methylnicotinonitrile (2.1 g, 6.83 mmol) in Ethanol (100 mL) was added hydrazine monohydrate (1.4 ml, 28.9 mmol). The reaction was stirred at RT for 18 h. LCMS showed that the reaction was done. The thick white suspension was filtered, pressed dry, washed with EtOH, and the filtrate evaporated to dryness under vacuum. The remaining solid was taken up in Dichloromethane (50 ml), filtered to remove additional insoluble material, and washed with CH₂Cl₂. To the clear filtrate with stirring was added Boc₂O (1.809 ml, 7.79 mmol). After stirring at RT for 1 hr LCMS showed that the reaction was complete. The reaction was concentrated under vacuum and purified by silica gel chromatography (Analogix, SF25-60, 0 to 10% EtOAc in hexanes). The pure fractions were combined and evaporated to dryness to give the product tert-butyl ((5-cyano-6-methoxy-4-methylpyridin-2-yl)methyl)carbamate (1.42 g, 5.12 mmol, 74.9% yield) as a white solid. ¹H NMR (400 MHz, DMSO-d₆) δ 7.48 (t, J=6.1 Hz, 1H), 6.91 (s, 1H), 4.16 (d, J=6.1 Hz, 2H), 3.96 (s, 3H), 2.45 (s, 3H), 1.41 (s, 9H). MS(ES)+ m/e 278.2 [M+H]⁺.

c) tert-Butyl ((5-(aminomethyl)-6-methoxy-4-methylpyridin-2-yl)methyl)carbamate

A clear solution of tert-butyl ((5-cyano-6-methoxy-4-methylpyridin-2-yl)methyl)carbamate (0.65 g, 2.344 mmol) in HOAc (5 mL) and Ethanol (20 mL) was treated on an H-Cube apparatus (50 psi, 40° C., 1 mL/min, Raney Nickel cartridge) for 18 hr overnight. LCMS showed that the reaction was complete. The reaction was evaporated to dryness under vacuum. Purified by silica gel chromatography (Analogix, SF25-60 g, 0 to 10% (5% NH₄OH/MeOH) in CH₂Cl₂). The pure fractions were combined and evaporated to dryness under vacuum to give the product tert-butyl ((5-(aminomethyl)-6-methoxy-4-methylpyridin-2-yl)methyl)carbamate (0.58 g, 2.061 mmol, 88% yield) as a clear thick oil. ¹H NMR (400 MHz, DMSO-d₆) δ 7.31 (t, J=6.1 Hz, 1H), 6.63 (s, 1H), 4.06 (d, J=6.3 Hz, 2H), 3.84 (s, 3H), 3.61 (s, 2H), 2.29 (s, 3H), 1.53 (br. s., 2H), 1.41 (s, 9H). MS(ES)+ m/e 282.2 [M+H]⁺.

Intermediate 20

The title compound was prepared in the same manner as described for 3-(aminomethyl)-4-ethyl-6-methyl-2(1H)-pyridinone (Intermediate 10c). LCMS (ES+) m/z=195.22 (M+H). ¹H NMR (DMSO-d₆, 400 MHz): δ 0.809-0.774 (t, 3H, J=6.8 Hz), 1.113-1.097 (d, 3H, J=6.4 Hz), 1.504-1.468 (t, 2H, J=7.2 Hz), 2.184 (s, 3H), 2.839-2.822 (d, 1H, J=6.8 Hz), 3.822 (s, 2H), 6.059 (s, 1H), 8.315 (bs, 2H).

Intermediate 21

2-Methoxy-5-(tributylstannyl)thiazole

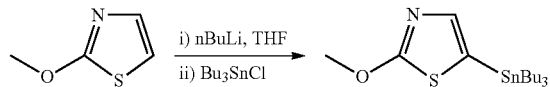

To a stirred solution of 2-methoxythiazole (5 g, 43.4 mmol) in tetrahydrofuran (THF) (50 mL) was added n-BuLi (35.3 mL, 56.4 mmol) and the contents stirred at −78° C. After 15 min, tributylchlorostannane (14.13 mL, 52.1 mmol) was added and the mixture stirred with warming to room temperature over a 3 h period. The reaction mixture was quenched with water (20 mL) and the contents extracted with ether (25 mL). The organic layer was separated and dried over anhydrous sodium sulphate, filtered, and the filtrate concentrated in vacuo to afford the crude product (6 g). The crude product was purified by silica gel column chromatography (eluent: 2% EtOAc/Hexane) to afford 2-methoxy-5-(tributylstannyl)thiazole (4 g, 22%) as yellow liquid. $^1$H NMR (400 MHz, CDCl$_3$-d$_3$) δ ppm 0.90-0.98 (m, 9H), 1.05-1.15 (m, 6H), 1.30-1.40 (m, 6H), 1.50-1.65 (m, 6H), 4.04 (s, 3H), 7.03 (s, 1H). LCMS(ES) [M+H]$^+$ 405.99.

Intermediate 22

2-Methoxythiazol-5-yl)boronic acid

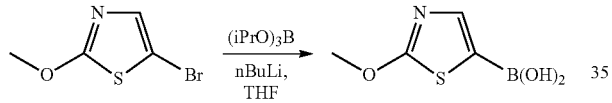

To a stirred solution of 5-bromo-2-methoxythiazole (500 mg, 2.58 mmol) in tetrahydrofuran (THF) (15 mL) was added triisopropyl borate (0.598 mL, 2.58 mmol) and then n-BuLi (2.416 mL, 3.87 mmol), and the contents stirred at −78° C. for 3 h. The reaction mixture was quenched with aq. NH$_4$C$_1$ (5 mL) and the contents extracted with ethyl acetate (15 mL). The organic layer was separated and dried over anhydrous sodium sulphate, filtered, and the filtrate concentrated in vacuo to afford the title compound (400 mg), which was used without further purification.

Intermediate 23

Methyl 2-methyl-3-((tetrahydrofuran-3-yl)oxy)benzoate

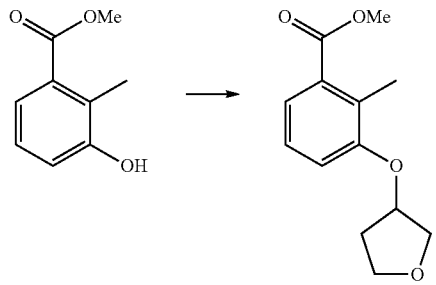 [SMILES: COC(=O)c1cccc(O)c1C ; COC(=O)c1cccc(OC2CCOC2)c1C]

To a solution of methyl 3-hydroxy-2-methylbenzoate (150 mg, 0.9 mmol) in 5 mL of THF were added tetrahydrofuran-3-ol (159 mg, 1.8 mmol), triphenylphosphine (474 mg, 1.8 mmol) and DIAD (0.49 ml, 2.5 mmol) and the mixture was stirred at room temperature overnight. The mixture was then evaporated and the residue preabsorbed on silica gel and purified using normal phase chromatography: Heptane/EtOAc (12 g column, gradient 0 to 100%) to give a colorless oil (145 mg, 67% yield). $^1$H NMR (400 MHz, DMSO-d$_6$) δ ppm 1.93-2.01 (m, 1H) 2.17-2.26 (m, 1H) 2.28-2.32 (m, 3H) 3.75-3.81 (m, 2H) 3.82 (s, 3H) 3.83-3.88 (m, 1H) 3.91 (dd, J=10.11, 4.55 Hz, 1H) 5.03-5.10 (m, 1H) 7.13-7.19 (m, 1H) 7.26 (t, J=7.83 Hz, 1H) 7.29-7.34 (m, 1H). MS(ES) [M+H]$^+$ 237.1.

Intermediate 24

Methyl 2-methyl-3-((1-methylpyrrolidin-3-yl)oxy)benzoate

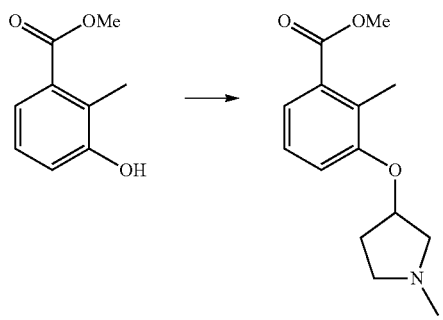 [SMILES: COC(=O)c1cccc(O)c1C ; COC(=O)c1cccc(OC2CCN(C)C2)c1C]

Following the procedure described for Intermediate 23, the title compound was prepared as a brownish oil (236 mg, 90% yield). MS(ES) [M+H]$^+$ 250.1.

Intermediate 25

Ethyl 2-methyl-3-(tetrahydro-2H-pyran-4-yloxy)benzoate

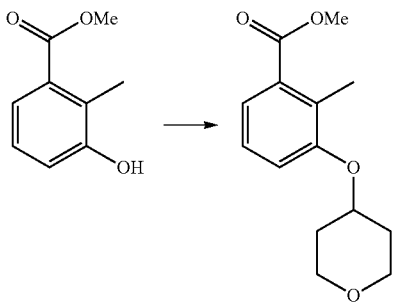 [SMILES: COC(=O)c1cccc(O)c1C ; COC(=O)c1cccc(OC2CCOCC2)c1C]

Following the procedure described for Intermediate 23, the title compound was prepared as a brownish oil (100 mg, 43% yield). MS(ES) [M+H]$^+$ 251.1.

EXAMPLES

Example 1

5-Bromo-2-methyl-3-[(1-methylethyl)amino]-N-[(6-methyl-2-oxo-4-propyl-1,2-dihydro-3-pyridinyl)methyl]benzamide

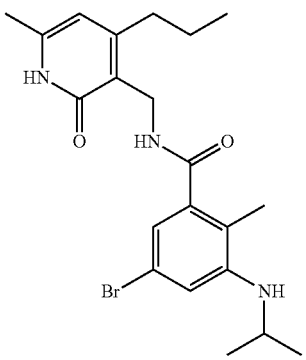 [SMILES: CCCc1cc(C)[nH]c(=O)c1CNC(=O)c1cc(Br)cc(NC(C)C)c1C]

a) Methyl 5-bromo-2-methyl-3-[(1-methylethyl)amino]benzoate

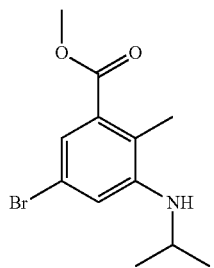 [SMILES: COC(=O)c1cc(Br)cc(NC(C)C)c1C]

To a 100 mL round bottom was added methyl 3-amino-5-bromo-2-methylbenzoate (1 g, 4.10 mmol) and acetone (3.01 mL, 41.0 mmol), followed by methanol (50 mL). Zinc chloride (1.675 g, 12.29 mmol) was added followed by sodium cyanoborohydride (1.030 g, 16.39 mmol). The reaction stirred at 40° C. for 20 h. The reaction was poured onto ice water (50 mL) that was saturated with NH$_4$Cl and was stirred for 20 min then rested for 10 min and filtered. The solid was rinsed with water (2×20 mL) to give the above product as an off-white solid. (500 mg, 1.573 mmol, 38.4% yield). $^1$H NMR (400 MHz, DMSO-d$_6$) δ ppm 6.96 (d, J=2.02 Hz, 1H) 6.82 (d, J=1.77 Hz, 1H) 4.93 (d, J=8.08 Hz, 1H) 3.79 (s, 3H) 3.59-3.70 (m, 1H) 2.10 (s, 3H) 1.17 (d, 6H). MS(ES) [M+H]$^+$ 288.1.

b) 5-Bromo-2-methyl-3-[(1-methylethyl)amino]benzoic acid

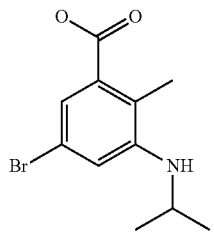

To a 10 ml vial was added methyl 5-bromo-2-methyl-3-[(1-methylethyl)amino]benzoate (500 mg, 1.747 mmol), methanol (2 mL) and tetrahydrofuran (THF) (10 mL). 6 M NaOH (0.874 mL, 5.24 mmol) was added and the reaction stirred at 40° C. for 20 h. The reaction was cooled and evaporated. The residual water was poured onto dilute acidic ice water (6 N HCl) (5 mL) pH ~4. The slurry was stirred 20 min (rested 10 min) then filtered. The solid was washed with water and dried to give the above product (270 mg, 0.962 mmol, 55.1% yield) as an off white solid. $^1$H NMR (400 MHz, DMSO-d$_6$) δ ppm 12.98 (br. s., 1H) 6.95 (s, 1H) 6.78 (bs, 1H) 4.87 (bs, 1H) 3.55-3.72 (m, 1H) 2.16 (s, 3H) 1.18 (d, J=6.32 Hz, 6H). MS(ES) [M+H]$^+$ 274.2.

c) 5-Bromo-2-methyl-3-[(1-methylethyl)amino]-N-[(6-methyl-2-oxo-4-propyl-1,2-dihydro-3-pyridinyl)methyl]benzamide

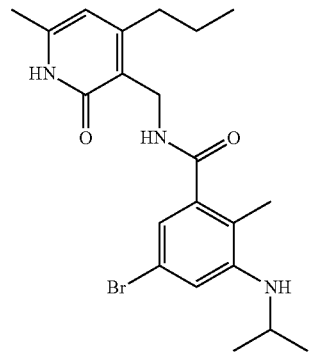 [SMILES: CCCc1cc(C)[nH]c(=O)c1CNC(=O)c1cc(Br)cc(NC(C)C)c1C]

To a 50 ml round bottom was added 5-bromo-2-methyl-3-[(1-methylethyl)amino]benzoic acid (270 mg, 0.992 mmol), 1-hydroxy-7-azabenzotriazole (203 mg, 1.488 mmol) and EDC (285 mg, 1.488 mmol) followed by dimethyl sulfoxide (DMSO) (20 mL). N-methylmorpholine (0.327 mL, 2.98 mmol) was added to the reaction followed by 3-(aminomethyl)-6-methyl-4-propyl-2(1H)-pyridinone (232 mg, 1.290 mmol). The reaction stirred at rt for 72 h. The reaction was poured onto ice water (10 mL) and was stirred for 20 min (rested for 10 min) and filtered. The solid was rinsed with water (10 mL) followed by MeOH/ice water (10 mL/10 mL) to provide the title compound as a tan solid. (299 mg, 0.661 mmol, 66.6% yield). $^1$H NMR (400 MHz, DMSO-d$_6$) δ ppm 11.48 (br. s., 1H) 8.08 (t, J=4.67 Hz, 1H) 6.66 (s, 1H) 6.52 (d, J=1.52 Hz, 1H) 5.88 (s, 1H) 4.74 (d, J=7.83 Hz, 1H) 4.24 (d, J=4.80 Hz, 2H) 3.54-3.67 (m, 1H) 2.45-2.48 (m, 2H) 2.12 (s, 3H) 1.96 (s, 3H) 1.47-1.56 (m, 2H) 1.16 (d, J=6.32 Hz, 6H) 0.90-0.94 (m, 3H). MS(ES) [M+H]$^+$ 434.0.

Example 2

2-Methyl-3-[(1-methylethyl)amino]-N-[(6-methyl-2-oxo-4-propyl-1,2-dihydro-3-pyridinyl)methyl]-5-[6-(4-methyl-1-piperazinyl)-3-pyridinyl]benzamide

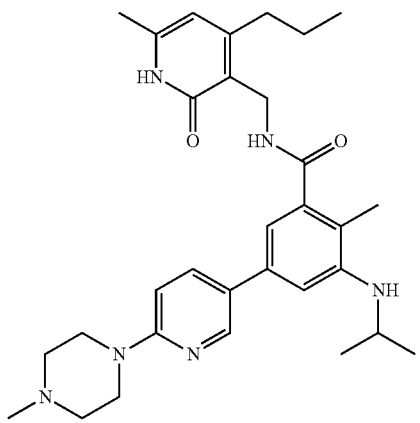 [SMILES: CCCc1cc(C)[nH]c(=O)c1CNC(=O)c1cc(-c2ccc(N3CCN(C)CC3)nc2)cc(NC(C)C)c1C]

To a 10 ml microwave vial was added 5-bromo-2-methyl-3-[(1-methylethyl)amino]-N-[(6-methyl-2-oxo-4-propyl-1,2-dihydro-3-pyridinyl)methyl]benzamide (130 mg, 0.299 mmol), 1-methyl-4-[5-(4,4,5,5-tetramethyl-1,3,2-dioxaborolan-2-yl)-2-pyridinyl]piperazine (127 mg, 0.389 mmol) then PdCl$_2$(dppf)-CH$_2$Cl$_2$ adduct (24.44 mg, 0.030 mmol) followed by 1,4-dioxane (10 mL). To the solution was added sodium bicarbonate (75 mg, 0.898 mmol) and water (2 mL). The vial was capped and the reaction stirred on a hot plate at 110° C. for 2 h. The reaction was cooled and evaporated. The residue was filtered through an acrodisc and purified by reverse phase Gilson HPLC (10-70% acetonitrile/water+ 0.1% TFA, YMC ODS-A C18 Column 75×30 mm ID S-5 um, 12 nM Column 7 minutes). The title compound was isolated as an off white solid after extraction of the desired fractions with EtOAc/NaHCO$_3$ (sat aq), evaporation precipitation (from MeOH/water (1/9)) and filtering. $^1$H NMR (400 MHz, DMSO-d$_6$) δ ppm 11.47 (br. s., 1H) 8.36 (d, J=2.53 Hz, 1H) 8.00 (t, J=4.93 Hz, 1H) 7.77 (dd, J=8.84, 2.53 Hz, 1H) 6.88 (d, J=9.09 Hz, 1H) 6.74 (d, J=1.01 Hz, 1H) 6.65 (d, J=1.52 Hz, 1H) 5.89 (s, 1H) 4.47 (d, J=8.08 Hz, 1H) 4.28 (d, J=4.80 Hz, 2H) 3.70-3.81 (m, 1H) 3.48-3.54 (m, 4H) 2.48-2.49 (m, 2H) 2.39-2.43 (m, 4H) 2.22 (s, 3H) 2.12 (s, 3H) 2.04 (s, 3H) 1.49-1.60 (m, 2H) 1.20 (d, J=6.32 Hz, 6H) 0.93 (t, 3H). MS(ES) [M+H]$^+$ 531.1.

Example 3

5-Bromo-N-[(4,6-dimethyl-2-oxo-1,2-dihydro-3-pyridinyl)methyl]-2-methyl-3-[(1-methylethyl)amino]benzamide

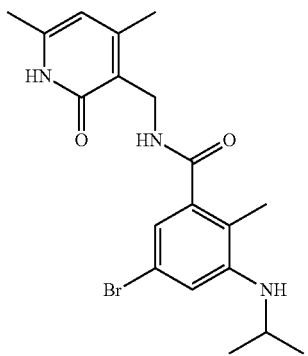 [SMILES: Cc1cc(C)c(CNC(=O)c2cc(Br)cc(NC(C)C)c2C)c(=O)[nH]1]

Following the general procedure similar of Example 1c, substituting 3-(aminomethyl)-4,6-dimethyl-2(1H)-pyridinone (407 mg, 2.68 mmol) for 3-(aminomethyl)-6-methyl-4-propyl-2(1H)-pyridinone the title compound was prepared (688 mg, 1.642 mmol, 80% yield) as a pale orange solid. $^1$H NMR (400 MHz, DMSO-d$_6$) δ ppm 11.47 (br. s., 1H) 8.05-8.20 (m, 1H) 6.66 (s, 1H) 6.53 (s, 1H) 5.86 (s, 1H) 4.73 (d, J=8.08 Hz, 1H) 4.23 (d, J=4.80 Hz, 2H) 3.63-3.58 (m, 1H) 2.18 (s, 3H) 2.11 (s, 3H) 1.95 (s, 3H) 1.16 (d, J=6.3 Hz 6H). MS(ES) [M+H]$^+$ 408.0.

Example 4

5-Bromo-2-methyl-3-[(1-methylethyl)amino]-N-{[6-methyl-2-oxo-4-(phenylmethyl)-1,2-dihydro-3-pyridinyl]methyl}benzamide

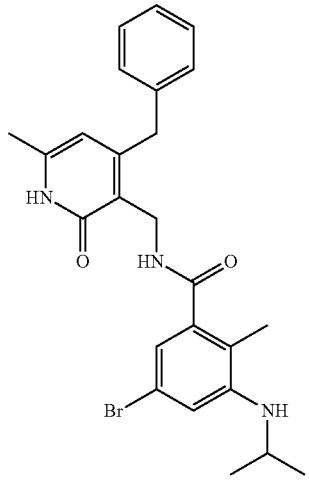 [SMILES: Cc1cc(Cc2ccccc2)c(CNC(=O)c2cc(Br)cc(NC(C)C)c2C)c(=O)[nH]1]

Following the general procedure of Example 1c, substituting 3-(aminomethyl)-6-methyl-4-(phenylmethyl)-2(1H)-pyridinone (101 mg, 0.441 mmol) for 3-(aminomethyl)-6-methyl-4-propyl-2(1H)-pyridinone, the above compound was prepared (38 mg, 0.077 mmol, 21.01% yield) as a solid. $^1$H NMR (400 MHz, DMSO-d$_6$) δ ppm 11.55 (br. s., 1H) 8.18-8.25 (m, 1H) 7.27-7.35 (m, 2H) 7.18-7.26 (m, 3H) 6.66 (d, J=1.77 Hz, 1H) 6.49 (d, J=1.77 Hz, 1H) 5.76 (s, 1H) 4.74 (d, J=8.08 Hz, 1H) 4.31 (d, J=5.05 Hz, 2H) 3.92 (s, 2H) 3.62 (s, 1H) 2.08 (s, 3H) 1.94 (s, 3H) 1.16 (d, J=6.32 Hz, 6H). MS(ES) [M+H]$^+$ 481.9

Example 5

2-Methyl-3-[(1-methylethyl)amino]-N-[(6-methyl-2-oxo-4-propyl-1,2-dihydro-3-pyridinyl)methyl]-5-[6-(methyloxy)-3-pyridinyl]benzamide

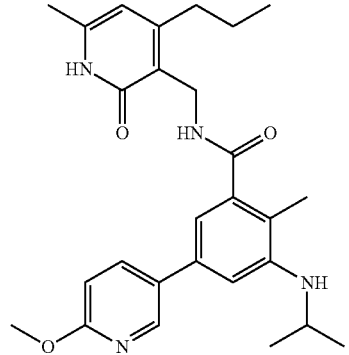 [SMILES: CCCc1cc(C)[nH]c(=O)c1CNC(=O)c1cc(-c2ccc(OC)nc2)cc(NC(C)C)c1C]

Following the general procedure of Example 2, substituting 2-methoxy-5-pyridineboronic acid (46.5 mg, 0.304 mmol) for 1-methyl-4-[5-(4,4,5,5-tetramethyl-1,3,2-dioxaborolan-2-yl)-2-pyridinyl]piperazine, 2-methyl-3-[(1-methylethyl)amino]-N-[(6-methyl-2-oxo-4-propyl-1,2-dihydro-3-pyridinyl)methyl]-5-[6-(methyloxy)-3-pyridinyl]benzamide (60 mg, 0.127 mmol, 46.0% yield) was isolated as an off white solid. $^1$H NMR (400 MHz, DMSO-d$_6$) δ ppm 11.48 (br. s., 1H) 8.40 (d, J=2.27 Hz, 1H) 8.02 (t, J=4.67 Hz, 1H) 7.94 (dd, J=8.59, 2.27 Hz, 1H) 6.88 (d, J=8.59 Hz, 1H)

6.77 (s, 1H) 6.68 (s, 1H) 5.89 (s, 1H) 4.52 (d, J=8.08 Hz, 1H) 4.29 (d, J=4.80 Hz, 2H) 3.88 (s, 3H) 3.78 (d, J=6.57 Hz, 1H) 2.48-2.49 (m, 2H) 2.12 (s, 3H) 2.05 (s, 3H) 1.49-1.62 (m, 2H) 1.20 (d, J=6.06 Hz, 6H) 0.93 (t, 3H). MS(ES) [M+H]$^+$ 463.3.

Example 6

N-[(4,6-Dimethyl-2-oxo-1,2-dihydro-3-pyridinyl)methyl]-2-methyl-3-[(1-methylethyl)amino]-5-[6-(methyloxy)-3-pyridinyl]benzamide

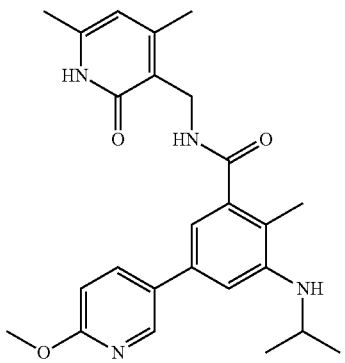 [SMILES: COc1ccc(-c2cc(NC(C)C)c(C)c(C(=O)NCc3c(C)cc(C)[nH]c3=O)c2)cn1]

Following the general procedure of Example 2, substituting 5-bromo-N-[(4,6-dimethyl-2-oxo-1,2-dihydro-3-pyridinyl)methyl]-2-methyl-3-[(1-methylethyl)amino]benzamide (150 mg, 0.369 mmol) for 5-bromo-2-methyl-3-[(1-methylethyl)amino]-N-[(6-methyl-2-oxo-4-propyl-1,2-dihydro-3-pyridinyl)methyl]benzamide and 2-methoxy-5-pyridineboronic acid (46.5 mg, 0.304 mmol) for 1-methyl-4-[5-(4,4,5,5-tetramethyl-1,3,2-dioxaborolan-2-yl)-2-pyridinyl]piperazine, N-[(4,6-dimethyl-2-oxo-1,2-dihydro-3-pyridinyl)methyl]-2-methyl-3-[(1-methylethyl)amino]-5-[6-(methyloxy)-3-pyridinyl]benzamide (110 mg, 0.248 mmol, 67.2% yield) was isolated as an off white solid. $^1$H NMR (400 MHz, DMSO-d$_6$) δ ppm 11.47 (s, 1H) 8.41 (d, J=2.02 Hz, 1H) 8.06 (t, J=5.05 Hz, 1H) 7.94 (dd, J=8.59, 2.53 Hz, 1H) 6.88 (d, J=8.59 Hz, 1H) 6.77 (s, 1H) 6.69 (d, J=1.52 Hz, 1H) 5.86 (s, 1H) 4.52 (d, J=8.08 Hz, 1H) 4.27 (d, J=5.05 Hz, 2H) 3.88 (s, 3H) 3.71-3.84 (m, 1H) 2.20 (s, 3H) 2.11 (s, 3H) 2.05 (s, 3H) 1.20 (d, J=6.63 Hz, 6H). MS(ES) [M+H]$^+$ 435.1.

Example 7

4'-[(Dimethylamino)methyl]-N-[(4,6-dimethyl-2-oxo-1,2-dihydro-3-pyridinyl)methyl]-4-methyl-5-[(1-methylethyl)amino]-3-biphenylcarboxamide

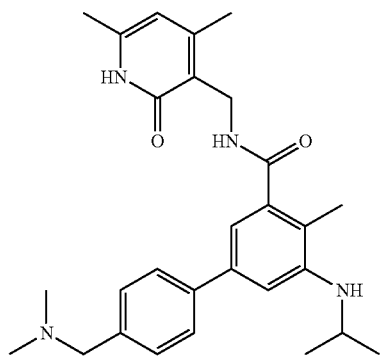 [SMILES: Cc1cc(C)c(CNC(=O)c2cc(-c3ccc(CN(C)C)cc3)cc(NC(C)C)c2C)c(=O)[nH]1]

Following the general procedure of Example 2, substituting 5-bromo-N-[(4,6-dimethyl-2-oxo-1,2-dihydro-3-pyridinyl)methyl]-2-methyl-3-[(1-methylethyl)amino]benzamide (150 mg, 0.369 mmol) for 5-bromo-2-methyl-3-[(1-methylethyl)amino]-N-[(6-methyl-2-oxo-4-propyl-1,2-dihydro-3-pyridinyl)methyl]benzamide and N,N-dimethyl-1-[4-(4,4,5,5-tetramethyl-1,3,2-dioxaborolan-2-yl)phenyl]methanamine (106 mg, 0.406 mmol) for 1-methyl-4-[5-(4,4,5,5-tetramethyl-1,3,2-dioxaborolan-2-yl)-2-pyridinyl]piperazine, 4'-[(dimethylamino)methyl]-N-[(4,6-dimethyl-2-oxo-1,2-dihydro-3-pyridinyl)methyl]-4-methyl-5-[(1-methylethyl)amino]-3-biphenylcarboxamide (55 mg, 0.112 mmol, 30.4% yield) was isolated as an off white solid. $^1$H NMR (400 MHz, DMSO-d$_6$) δ ppm 11.46 (br. s., 1H) 8.06 (t, J=4.93 Hz, 1H) 7.55 (d, J=8.08 Hz, 2H) 7.33 (d, J=8.08 Hz, 2H) 6.79 (s, 1H) 6.71 (d, J=1.52 Hz, 1H) 5.86 (s, 1H) 4.49 (d, J=8.34 Hz, 1H) 4.28 (d, J=4.80 Hz, 2H) 3.71-3.82 (m, 1H) 3.40 (s, 2H) 2.20 (s, 3H) 2.16 (s, 6H) 2.11 (s, 3H) 2.05 (s, 3H) 1.21 (d, J=6.32 Hz, 6H). MS(ES) [M+H]$^+$ 461.1.

Example 8

5-(6-Amino-3-pyridinyl)-N-[(4,6-dimethyl-2-oxo-1,2-dihydro-3-pyridinyl)methyl]-2-methyl-3-[(1-methylethyl)amino]benzamide

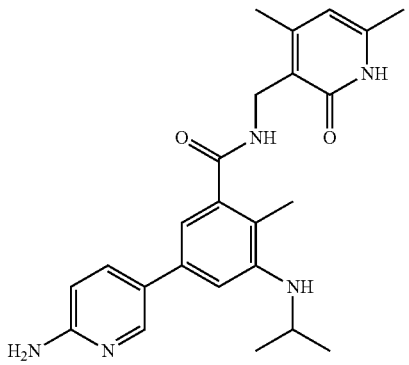 [SMILES: Cc1cc(C)c(CNC(=O)c2cc(-c3ccc(N)nc3)cc(NC(C)C)c2C)c(=O)[nH]1]

Following the general procedure of Example 2, substituting 5-bromo-N-[(4,6-dimethyl-2-oxo-1,2-dihydro-3-pyridinyl)methyl]-2-methyl-3-[(1-methylethyl)amino]benzamide (150 mg, 0.369 mmol) for 5-bromo-2-methyl-3-[(1-methylethyl)amino]-N-[(6-methyl-2-oxo-4-propyl-1,2-dihydro-3-pyridinyl)methyl]benzamide and 5-(4,4,5,5-tetramethyl-1,3,2-dioxaborolan-2-yl)-2-pyridinamine (89 mg, 0.406 mmol) for 1-methyl-4-[5-(4,4,5,5-tetramethyl-1,3,2-dioxaborolan-2-yl)-2-pyridinyl]piperazine the title compound 5-(6-amino-3-pyridinyl)-N-[(4,6-dimethyl-2-oxo-1,2-dihydro-3-pyridinyl)methyl]-2-methyl-3-[(1-methylethyl)amino]benzamide (42 mg, 0.094 mmol, 25.5% yield) was isolated as an off white solid. $^1$H NMR (400 MHz, DMSO-d$_6$) δ ppm 11.47 (s, 1H) 8.16 (d, J=2.02 Hz, 1H) 8.02 (t, J=5.05 Hz, 1H) 7.62 (dd, J=8.46, 2.65 Hz, 1H) 6.69 (d, J=1.26 Hz, 1H) 6.61 (d, J=1.52 Hz, 1H) 6.49 (d, J=8.59 Hz, 1H) 5.99 (s, 2H) 5.86 (s, 1H) 4.43 (d, J=8.34 Hz, 1H) 4.27 (d, J=5.05 Hz, 2H) 3.70-3.79 (m, 1H) 2.20 (s, 3H) 2.11 (s, 3H) 2.02 (s, 3H) 1.19 (d, J=6.32 Hz, 6H). MS(ES) [M+H]$^+$ 420.0.

Example 9

N-[(4,6-Dimethyl-2-oxo-1,2-dihydro-3-pyridinyl)methyl]-2-methyl-3-[(1-methylethyl)amino]-5-[6-(1-piperazinyl)-3-pyridinyl]benzamide

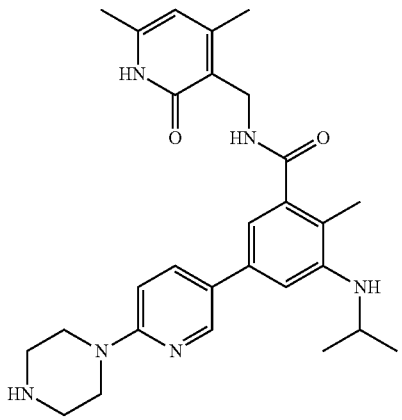 [SMILES: Cc1cc(C)c(CNC(=O)c2cc(-c3ccc(N4CCNCC4)nc3)cc(NC(C)C)c2C)c(=O)[nH]1]

Following the general procedure of Example 2, substituting 5-bromo-N-[(4,6-dimethyl-2-oxo-1,2-dihydro-3-pyridinyl)methyl]-2-methyl-3-[(1-methylethyl)amino]benzamide (150 mg, 0.369 mmol) for 5-bromo-2-methyl-3-[(1-methylethyl)amino]-N-[(6-methyl-2-oxo-4-propyl-1,2-dihydro-3-pyridinyl)methyl]benzamide and 6-(1-piperazinyl)pyridine-3-boronic acid pinacol ester (117 mg, 0.406 mmol) for 1-methyl-4-[5-(4,4,5,5-tetramethyl-1,3,2-dioxaborolan-2-yl)-2-pyridinyl]piperazine (127 mg, 0.389 mmol) the title compound was isolated as an off-white solid N-[(4,6-dimethyl-2-oxo-1,2-dihydro-3-pyridinyl)methyl]-2-methyl-3-[(1-methylethyl)amino]-5-[6-(1-piperazinyl)-3-pyridinyl]benzamide (50 mg, 0.097 mmol, 26.3% yield) $^1$H NMR (400 MHz, DMSO-$d_6$) δ ppm 11.47 (br. s., 1H) 8.36 (d, J=2.27 Hz, 1H) 8.03 (t, J=4.93 Hz, 1H) 7.73-7.81 (m, 1H) 6.84 (d, J=8.84 Hz, 1H) 6.74 (d, J=1.52 Hz, 1H) 6.65 (d, J=1.77 Hz, 1H) 5.86 (s, 1H) 4.46 (d, J=8.08 Hz, 1H) 4.27 (d, J=4.80 Hz, 2H) 3.70-3.83 (m, 1H) 3.40-3.55 (m, 4H) 2.75-2.83 (m, 4H) 2.20 (s, 3H) 2.11 (s, 3H) 2.03 (s, 3H) 1.20 (d, J=6.06 Hz, 6H). MS(ES) [M+H]$^+$ 489.1.

Example 10

N-((4,6-dimethyl-2-oxo-1,2-dihydropyridin-3-yl)methyl)-3-(isopropylamino)-5-(2-methoxythiazol-5-yl)-2-methylbenzamide

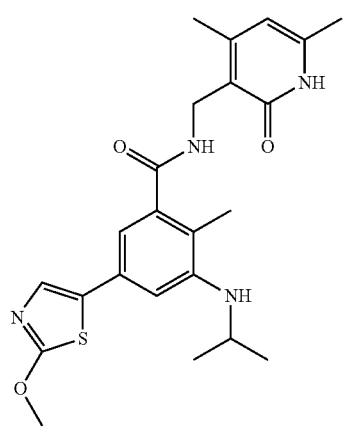 [SMILES: COc1ncc(-c2cc(NC(C)C)c(C)c(C(=O)NCc3c(C)cc(C)[nH]c3=O)c2)s1]

A stirred solution of 5-bromo-N-((4,6-dimethyl-2-oxo-1,2-dihydropyridin-3-yl)methyl)-3-(isopropylamino)-2-methylbenzamide (400 mg, 0.984 mmol), (2-methoxythiazol-5-yl)boronic acid (156 mg, 0.984 mmol) and cesium carbonate (802 mg, 2.461 mmol) in toluene (10 mL) and water (1 mL) were degassed with argon for 30 min. Next added Pd(Ph$_3$P)$_4$ (11.38 mg, 9.84 µmol) and the contents were heated to 110° C. for 16 h in a sealed tube. The contents were concentrated in vacuo and then extracted with ethyl acetate (50 mL) and washed with water (15 mL). The organic layer was separated, dried over anhydrous sodium sulphate, filtered, and concentrated to afford 500 mg of crude product. The crude product was purified by silica gel chromatography (eluent: 3% MeOH/DCM) to afford 130 mg of solid. The contents were again washed with ether (15 mL), filtered and dried to afford the title compound (100 mg, 22% yield) as a pale yellow solid. $^1$H NMR (400 MHz, DMSO-$d_6$) δ ppm 1.17 (d, 6H, J=6.4 Hz), 2.00 (s, 3H), 2.10 (s, 3H), 2.19 (s, 3H), 3.69-3.74 (m, 1H), 4.03 (s, 3H), 4.26 (d, 2H, J=4.9 Hz), 4.54 (d, 1H, J=7.9 Hz), 5.85 (s, 1H), 6.56 (d, 1H, J=1.8 Hz), 6.66 (s, 1H), 7.52 (s, 1H), 8.04 (t, 1H, J=4.9 Hz), 11.5 (s, 1H). LCMS(ES) [M+H]$^+$ 441.3.

Example 11

5-Bromo-3-(sec-butylamino)-N-((4,6-dimethyl-2-oxo-1,2-dihydropyridin-3-yl)methyl)-2-methylbenzamide

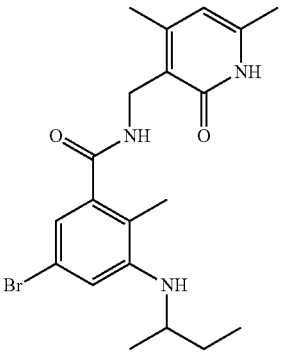 [SMILES: CCC(C)Nc1cc(Br)cc(C(=O)NCc2c(C)cc(C)[nH]c2=O)c1C]

a) Methyl 5-bromo-3-(sec-butylamino)-2-methylbenzoate

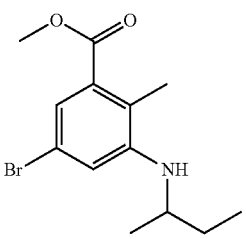 [SMILES: CCC(C)Nc1cc(Br)cc(C(=O)OC)c1C]

To a stirred solution of methyl 3-amino-5-bromo-2-methylbenzoate (5.0 g, 20.48 mmol) and butan-2-one (14.77 g, 205 mmol) in methanol (250 mL) was added zinc chloride (8.38 g, 61.5 mmol) followed by sodium cyanoborohydride (5.15 g, 82 mmol) at room temperature. The reaction mixture was stirred at 50° C. for 20 h, and then concentrated under reduced pressure. The contents were washed with water (50 mL) and extracted with EtOAC (150 mL). The organic layer was separated and dried over anhydrous sodium sulphate, filtered, and concentrated to afford the crude product (5 g). The crude product was purified by silica gel chromatography (eluent: 5% EtOAC/Hexane) to afford the title compound (3.0 g, 48%) as brown coloured liquid. LCMS(ES) [M+H]$^+$300.0.

b) 5-Bromo-3-(sec-butylamino)-2-methylbenzoic acid

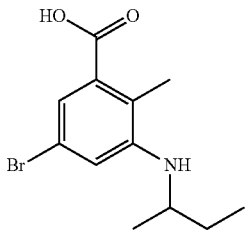 [SMILES: CCC(C)Nc1cc(Br)cc(C(=O)O)c1C]

To a suspension of methyl 5-bromo-3-(sec-butylamino)-2-methylbenzoate (3.0 g, 9.99 mmol) in tetrahydrofuran (25 mL) and water (25.00 mL) was added LiOH (1.436 g, 60.0 mmol) and the reaction mixture stirred at 70° C. for 16 h. The volatiles were removed in vacuo and the pH adjusted to 1-2 using 6 N HCl (15 mL) wherein precipitation ensued. The contents were filtered and dried to afford the title compound (2.5 g, 87%) as an off-white solid. $^1$H NMR (400 MHz, DMSO-d$_6$) δ ppm 0.95 (t, 3H, J=7.4 Hz), 1.17 (d, 3H, J=6.4 Hz), 1.41-1.54 (m, 1H), 1.57-1.64 (m, 1H), 2.17 (s, 3H), 3.37-3.43 (m, 1H), 5.78 (m, 1H), 6.77 (s, 1H), 6.95 (s, 1H), 12.8-13.0 (br s, 1H).

c) 5-Bromo-3-(sec-butylamino)-N-((4,6-dimethyl-2-oxo-1,2-dihydropyridin-3-yl)methyl)-2-methylbenzamide

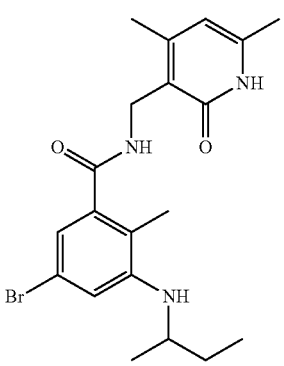

To a stirred solution of 5-bromo-3-(sec-butylamino)-2-methylbenzoic acid (1.0 g, 3.49 mmol), EDC (1.005 g, 5.24 mmol), and HOBT (0.803 g, 5.24 mmol) in dimethyl sulfoxide (DMSO) (40 mL) was added N-methylmorpholine (1.537 mL, 13.98 mmol) followed by 3-(aminomethyl)-4,6-dimethylpyridin-2(1H)-one, hydrochloride (0.791 g, 4.19 mmol). The reaction mixture was stirred at 25° C. for 16 h. The reaction mixture was poured onto ice water (50 mL), stirred for 10 min, allowed to stand for 10 min, and filtered. The collected solid was rinsed with water (50 mL) followed by 10% MeOH/ice water (50 mL), and then diethyl ether (25 mL). The contents were filtered and dried to afford the title compound (750 mg, 51%) as an off-white solid. $^1$H NMR (400 MHz, DMSO-d$_6$) δ ppm 0.86 (t, 3H, J=7.5 Hz), 1.10 (d, 3H, J=6.4 Hz), 1.41-1.48 (m, 1H), 1.55-1.62 (m, 1H), 1.95 (s, 3H), 2.11 (s, 3H), 2.17 (s, 3H), 3.34-3.39 (m, 1H), 4.23 (d, 2H, J=4.9 Hz), 4.65 (d, 1H, J=7.9 Hz), 5.85 (s, 1H), 6.55 (s, 1H), 6.63 (s, 1H), 8.03 (t, 1H, J=4.9 Hz), 11.5 (s, 1H). LCMS(ES) [M+H]$^+$ 420.4.

Example 12

3-(sec-Butylamino)-N-((4,6-dimethyl-2-oxo-1,2-dihydropyridin-3-yl)methyl)-5-(2-methoxythiazol-5-yl)-2-methylbenzamide

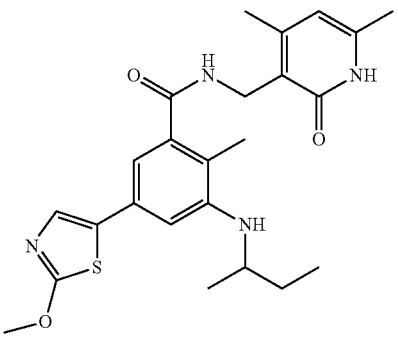

A stirred solution of 5-bromo-3-(sec-butylamino)-N-((4,6-dimethyl-2-oxo-1,2-dihydropyridin-3-yl)methyl)-2-methylbenzamide (500 mg, 1.190 mmol) and 2-methoxy-5-(tributylstannyl)thiazole (481 mg, 1.190 mmol) in toluene (15 mL) was degassed with argon for 20 min and then Pd(Ph$_3$P)$_4$ (13.75 mg, 0.012 mmol) was added. The reaction mixture was heated to 120° C. for 16 h in a sealed tube. The contents were concentrated in vacuo and the crude product was purified by silica gel chromatography (eluent: 4% MeOH/DCM) to afford the title compound (103 mg, 19% yield) as a pale yellow coloured solid. $^1$H NMR (400 MHz, DMSO-d$_6$) δ ppm 0.89 (t, 3H, J=7.4 Hz), 1.14 (d, 3H, J=6.4 Hz), 1.44-1.51 (m, 1H), 1.57-1.64 (m, 1H), 2.00 (s, 3H), 2.11 (s, 3H), 2.19 (s, 3H), 3.45-3.52 (m, 1H), 4.03 (s, 3H), 4.25 (d, 2H, J=4.9 Hz), 4.50 (d, 1H, J=8.4 Hz), 5.85 (s, 1H), 6.55 (d, 1H, J=1.5 Hz), 6.63 (s, 1H), 7.51 (s, 1H), 8.03 (t, 1H, J=4.9 Hz), 11.5 (s, 1H). LCMS(ES) [M+H]$^+$ 455.3

Example 13

5-Bromo-2-methyl-3-[methyl(1-methylethyl)amino]-N-[(6-methyl-2-oxo-4-propyl-1, 2-dihydro-3-pyridinyl)methyl]benzamide

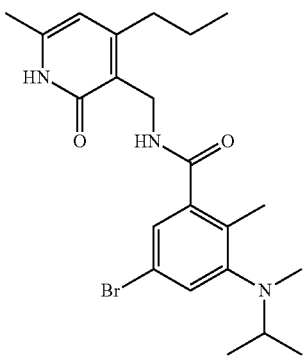

a) Methyl 5-bromo-2-methyl-3-[methyl(1-methylethyl)amino]benzoate

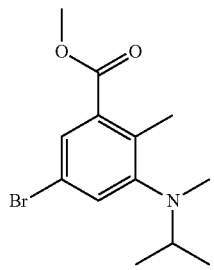 [SMILES: COC(=O)c1cc(Br)cc(N(C)C(C)C)c1C]

To a 10 ml microwave vial was added methyl 5-bromo-2-methyl-3-[(1-methylethyl)amino]benzoate (500 mg, 1.747 mmol), cesium carbonate (1708 mg, 5.24 mmol) and potassium iodide (290 mg, 1.747 mmol), followed by acetonitrile (6 mL). Methyl iodide (0.219 mL, 3.49 mmol) was added to the solution and the vial was capped and stirred at 60° C. for 4 days. The reaction was poured onto ice water (50 mL) that was saturated with NH$_4$C$_1$ and was stirred for 20 min The aqueous mixture was extracted with EtOAc. The organic layer was evaporated and purified by silica gel chromatography (Analogix IF280, 10-30% EtOAc/hexanes, SF25-40 g, 20 minutes) Purification provided methyl 5-bromo-2-methyl-3-[methyl(1-methylethyl)amino]benzoate (386 mg, 1.157 mmol, 66.2% yield) as an orange oil. $^1$H NMR (400 MHz, DMSO-d$_6$) δ ppm 7.51 (d, J=2.02 Hz, 1H) 7.35 (d, J=2.02 Hz, 1H) 3.11-3.23 (m, 1H) 2.56 (s, 3H) 2.31 (s, 3H) 1.03 (d, J=6.57 Hz, 6H) MS(ES) [M+H]$^+$ 300.2.

b) 5-Bromo-2-methyl-3-[methyl(1-methylethyl)amino]benzoic acid

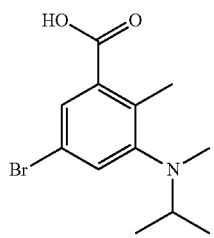 [SMILES: Cc1c(C(=O)O)cc(Br)cc1N(C)C(C)C]

Following the general procedure of Example 1b, but substituting methyl 5-bromo-2-methyl-3-[methyl(1-methylethyl)amino]benzoate (386 mg, 1.286 mmol) for methyl 5-bromo-2-methyl-3-[(1-methylethyl)amino]benzoate, the title compound 5-bromo-2-methyl-3-[methyl(1-methylethyl)amino]benzoic acid (213 mg, 0.595 mmol, 46.3% yield) was isolated as a clear oil. $^1$H NMR (400 MHz, DMSO-d$_6$) δ ppm 7.39 (d, J=2.27 Hz, 1H) 7.23 (d, J=2.27 Hz, 1H) 3.18-3.12 (m, 1H) 2.54 (s, 3H) 2.29 (s, 3H) 1.02 (d, J=6.51 Hz, 6H). MS(ES) [M+H]$^+$ 288.1.

c) 5-Bromo-2-methyl-3-[methyl(1-methylethyl)amino]-N-[(6-methyl-2-oxo-4-propyl-1,2-dihydro-3-pyridinyl)methyl]benzamide

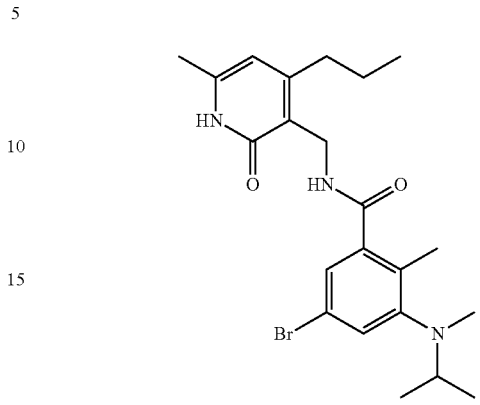

Following the general procedure of Example 1c, but substituting 5-bromo-2-methyl-3-[methyl(1-methylethyl)amino]benzoic acid (210 mg, 0.734 mmol), for 5-bromo-2-methyl-3-[(1-methylethyl)amino]benzoic acid (270 mg, 0.992 mmol), the title compound, 5-bromo-2-methyl-3-[methyl(1-methylethyl)amino]-N-[(6-methyl-2-oxo-4-propyl-1,2-dihydro-3-pyridinyl)methyl]benzamide (105 mg, 0.229 mmol, 31.3% yield), was prepared as a solid. $^1$H NMR (400 MHz, DMSO-d$_6$) δ ppm 11.49 (br. s., 1H) 8.19 (t, J=4.80 Hz, 1H) 7.15 (d, J=2.02 Hz, 1H) 7.00 (d, J=2.02 Hz, 1H) 5.89 (s, 1H) 4.25 (d, J=5.05 Hz, 2 H) 3.17 (t, J=6.57 Hz, 1H) 2.53 (s, 3H) 2.47-2.50 (m, 2H) 2.12 (d, J=2.53 Hz, 6H) 1.48-1.59 (m, 2H) 1.02 (d, J=6.57 Hz, 6H) 0.93 (t, J=7.33 Hz, 3H) MS(ES) [M+H]$^+$ 447.8.

Example 14

5-Bromo-N-((4,6-dimethyl-2-oxo-1,2-dihydropyridin-3-yl)methyl)-3-(isopropyl(methyl)amino)-2-methylbenzamide

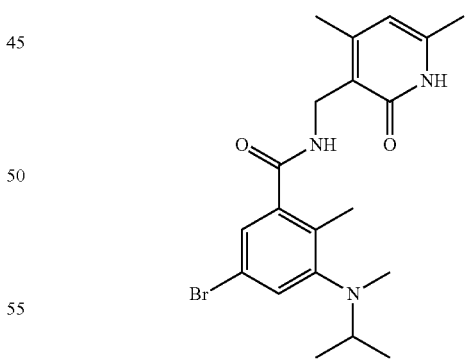

To a stirred solution of 5-bromo-3-(isopropyl(methyl)amino)-2-methylbenzoic acid (500 mg, 1.747 mmol), EDC (502 mg, 2.62 mmol), and HOBT (401 mg, 2.62 mmol) in dimethyl sulfoxide (DMSO) (20 mL) was added N-methylmorpholine (0.768 mL, 6.99 mmol), followed by 3-(aminomethyl)-4,6-dimethylpyridin-2(1H)-one hydrochloride (396 mg, 2.097 mmol). The reaction mixture was stirred at 25° C. for 16 h. The reaction mixture was poured onto ice water (25 mL), stirred for 10 min, allowed to stand for 10 min, and then filtered. The collected solid was rinsed with water (25 mL), followed by 10% MeOH/ice water (15 mL) and diethyl ether (25 mL). The contents were filtered and dried to afford the title compound (200 mg, 27%) as pale orange solid. $^1$H NMR (400 MHz, DMSO-d$_6$) δ ppm 1.01 (d, 6H, J=6.4 Hz), 2.11 (s, 6H), 2.18 (s, 3H), 2.53 (s, 3H), 3.14-3.20 (m, 1H), 4.23 (d, 2H, J=4.9 Hz), 5.85 (s, 1H), 7.00 (s, 1H), 7.14 (s, 1H), 8.17 (t, 1H, J=4.9 Hz), 11.5 (s, 1H). LCMS(ES) [M+H]$^+$ 420.5.

Example 15

N-((4,6-dimethyl-2-oxo-1,2-dihydropyridin-3-yl)methyl)-3-(isopropyl(methyl)amino)-5-(2-methoxythiazol-5-yl)-2-methylbenzamide

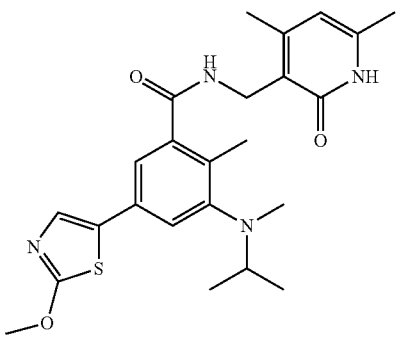

A stirred solution of 5-bromo-N-((4,6-dimethyl-2-oxo-1,2-dihydropyridin-3-yl)methyl)-3-(isopropyl(methyl)amino)-2-methylbenzamide (500 mg, 1.190 mmol) and 2-methoxy-5-(tributylstannyl)thiazole (481 mg, 1.190 mmol) in toluene (15 mL) was degassed with argon for 20 min and Pd(Ph$_3$P)$_4$ (13.75 mg, 0.012 mmol) was added. The reaction mixture was heated to 120° C. for 16 h in a sealed tube. The contents were concentrated in vacuo and the crude residue purified by silica gel chromatography (eluent: 3% MeOH/DCM) to afford 135 mg of solid. The solid was triturated with ether (15 mL), filtered, and dried in vacuo to afford the title compound (111 mg, 20%) as pale yellow coloured solid. $^1$H NMR (400 MHz, DMSO-d$_6$) δ ppm 1.02 (d, 6H, J=6.6 Hz), 2.11 (s, 3H), 2.16 (s, 3H), 2.20 (s, 3H), 2.58 (s, 3H), 3.16-3.28 (m, 1H), 4.04 (s, 3H), 4.26 (d, 2H, J=4.9 Hz), 5.86 (s, 1H), 7.00 (s, 1H), 7.13 (s, 1H), 7.59 (s, 1H), 8.14 (s, 1H), 11.5 (s, 1H). LCMS(ES) [M+H]$^+$ 455.3.

Example 16

5-Bromo-3-(sec-butyl(methyl)amino)-N-((4,6-dimethyl-2-oxo-1,2-dihydropyridin-3-yl)methyl)-2-methylbenzamide

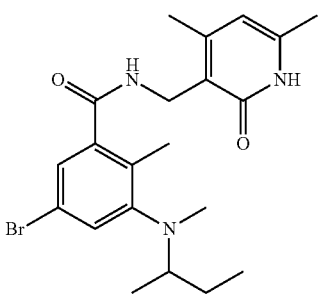 [SMILES: CCC(C)N(C)c1cc(Br)cc(C(=O)NCc2c(C)cc(C)[nH]c2=O)c1C]

a) Methyl 5-bromo-3-(sec-butyl(methyl)amino)-2-methylbenzoate

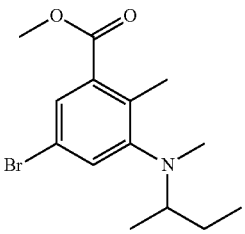 [SMILES: CCC(C)N(C)c1cc(Br)cc(C(=O)OC)c1C]

To a stirred solution of methyl 5-bromo-3-(sec-butylamino)-2-methylbenzoate (2.5 g, 8.33 mmol) and formaldehyde (12.40 mL, 167 mmol) in methanol (250 mL) was added zinc chloride (3.40 g, 24.98 mmol) followed by sodium cyanoborohydride (2.093 g, 33.3 mmol) at room temperature. The mixture was stirred at 50° C. for 20 h and then concentrated under reduced pressure. The contents were washed with water (50 mL) and extracted with EtOAC (150 mL). The organic layer was separated and dried over anhydrous sodium sulphate, filtered, and concentrated under reduced pressure to afford the crude product (4 g). The crude product was purified by silica gel chromatography (eluent: 5% EtOAC/Hexane) to afford the title compound (2.0 g, 76%) as colourless liquid. $^1$H NMR (400 MHz, DMSO-d$_6$) δ ppm 0.84 (t, 3H, J=7.4 Hz), 0.95 (d, 3H, J=6.4 Hz), 1.38-1.58 (m, 2H), 2.35 (s, 3H), 2.58 (s, 3H), 2.90-2.98 (m, 1H), 3.80 (s, 3H), 7.30 (s, 1H), 7.50 (s, 1H). LCMS(ES) [M+H]$^+$ 314.3.

b) 5-Bromo-3-(sec-butyl(methyl)amino)-2-methylbenzoic acid

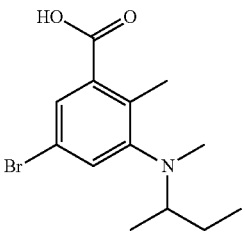 [SMILES: CCC(C)N(C)c1cc(Br)cc(C(=O)O)c1C]

To a suspension of methyl 5-bromo-3-(sec-butyl(methyl)amino)-2-methylbenzoate (2.0 g, 6.37 mmol) in tetrahydrofuran (25 mL) and water (25.00 mL) was added LiOH (0.915 g, 38.2 mmol) and the contents stirred at 70° C. for 20 h. The volatiles were removed in vacuo and the pH adjusted to 1-2 using 6 N HCl (15 mL), wherein precipitation ensued. The contents were filtered and dried to afford the title compound (1.5 g, 78%) as an off-white solid. $^1$H NMR (400 MHz, DMSO-d$_6$) δ ppm 0.84 (t, 3H, J=7.4 Hz), 0.95 (d, 3H, J=6.4 Hz), 1.38-1.58 (m, 2H), 2.35 (s, 3H), 2.58 (s, 3H), 2.85-2.95 (m, 1H), 7.30 (s, 1H), 7.45 (s, 1H), 12.8-13.2 (br s, 1H). LCMS(ES) [M+H]$^+$ 299.9.

c) 5-Bromo-3-(sec-butyl(methyl)amino)-N-((4,6-dimethyl-2-oxo-1,2-dihydropyridin-3-yl)methyl)-2-methylbenzamide

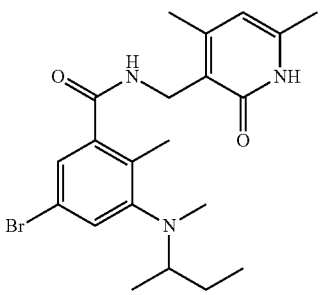 [SMILES: CCC(C)N(C)c1cc(Br)cc(C(=O)NCc2c(C)cc(C)[nH]c2=O)c1C]

To a stirred solution of 5-bromo-3-(sec-butyl(methyl)amino)-2-methylbenzoic acid (500 mg, 1.666 mmol), EDC (479 mg, 2.498 mmol), and HOBT (383 mg, 2.498 mmol) in dimethyl sulfoxide (DMSO) (40 mL) was added N-methylmorpholine (0.732 mL, 6.66 mmol), followed by 3-(aminomethyl)-4,6-dimethylpyridin-2(1H)-one hydrochloride (377 mg, 1.999 mmol). The reaction mixture was stirred at 25° C. for 16 h. The reaction mixture was poured onto ice water (50 mL), stirred for 10 min, allowed to stand for 10 min, and then filtered. The collected solid was rinsed with water (50 mL), followed by 10% MeOH/ice water (50 mL) and diethyl ether (25 mL). The contents were filtered and dried to afford 400 mg of crude product. The product was purified by silica gel chromatography (eluent: 100% EtOAc) to afford the title compound (200 mg, 27% yield) as an off-white solid. $^1$H NMR (400 MHz, DMSO-d$_6$) δ ppm 0.83 (t, 3H, J=7.5 Hz), 0.96 (d, 3H, J=6.4 Hz), 1.41-1.49 (m, 1H), 1.51-1.57 (m, 1H), 2.11 (s, 6H), 2.18 (s, 3H), 2.53 (s, 3H), 2.90-2.96 (m, 1H), 4.23 (d, 2H, J=4.9 Hz), 5.85 (s, 1H), 6.99 (s, 1H), 7.14 (s, 1H), 8.17 (t, 1H, J=4.9 Hz), 11.5 (s, 1H). LCMS(ES) [M+H]$^+$ 434.5.

Example 17

3-(sec-Butyl(methyl)amino)-N-((4,6-dimethyl-2-oxo-1,2-dihydropyridin-3-yl)methyl)-5-(2-methoxythiazol-5-yl)-2-methylbenzamide

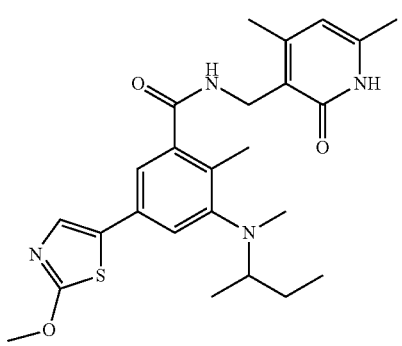

A stirred solution of 5-bromo-3-(sec-butyl(methyl)amino)-N-((4,6-dimethyl-2-oxo-1,2-dihydropyridin-3-yl)methyl)-2-methylbenzamide (500 mg, 1.151 mmol) and 2-methoxy-5-(tributylstannyl)thiazole (465 mg, 1.151 mmol) in toluene (15 mL) was degassed with argon for 20 min and then Pd(Ph$_3$P)$_4$ (13.30 mg, 0.012 mmol) was added. The reaction mixture was heated to 120° C. for 16 h in a sealed tube. The reaction mixture was concentrated under reduced pressure. The crude residue was purified by silica gel chromatography (eluent: 3% MeOH/DCM) to afford the title compound (130 mg, 24% yield) as a white solid. $^1$H NMR (400 MHz, DMSO-d$_6$) δ ppm 0.84 (t, 3H, J=7.4 Hz), 0.98 (d, 3H, J=6.4 Hz), 1.41-1.48 (m, 1H), 1.53-1.59 (m, 1H), 2.11 (s, 3H), 2.16 (s, 3H), 2.20 (s, 3H), 2.58 (s, 3H), 2.92-2.97 (m, 1H), 4.03 (s, 3H), 4.26 (d, 2H, J=4.9 Hz), 5.86 (s, 1H), 6.99 (d, 1H, J=1.8 Hz), 7.12 (s, 1H), 7.58 (s, 1H), 8.14 (t, 1H, J=4.9 Hz), 11.5 (s, 1H). LCMS(ES) [M+H]$^+$ 469.3.

Example 18

5-Bromo-N-((4,6-dimethyl-2-oxo-1,2-dihydropyridin-3-yl)methyl)-2-methyl-3-(2-methylpyrrolidin-1-yl)benzamide

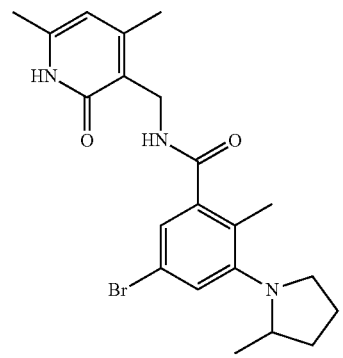 [SMILES: Cc1cc(C)c(CNC(=O)c2cc(Br)cc(N3CCCC3C)c2C)c(=O)[nH]1]

a) 5-bromo-2-methyl-3-(2-methylpyrrolidin-1-yl)benzoic acid

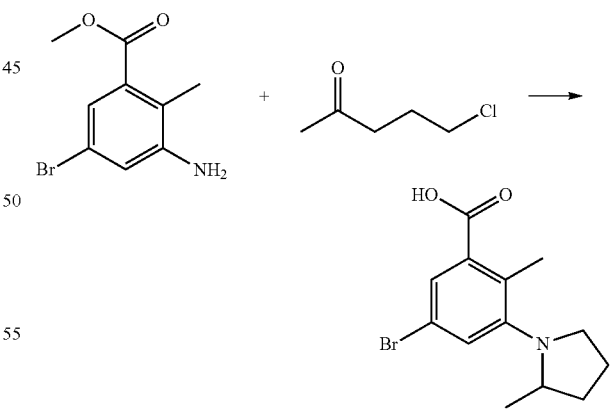

To a stirred solution of methyl 3-amino-5-bromo-2-methylbenzoate (0.5 g, 2.048 mmol) in methanol (20 mL) was added 5-chloropentan-2-one (3.0 ml, 26.3 mmol), followed by zinc chloride (0.85 g, 6.24 mmol). The reaction was stirred at room temperature for 2 h, then treated with sodium cyanoborohydride (0.7 g, 11.14 mmol) portionwise (gas evolution). The reaction was heated to 40° C. and stirred for 4 h, then heated to reflux (80° C. oil bath) and stirred overnight. LCMS showed only cyclized product (92%). The reaction was evaporated to dryness, taken up in EtOAc, washed with aq. NH₄Cl, 1 N Na₂CO₃, brine, dried (Na₂SO₄), filtered, and evaporated to dryness. Purification by silica gel chromatography (Analogix, SF25-60 g, 0 to 10% EtOAc in hexanes) gave the intermediate methyl ester (0.65 g, 2.0 mmol) as a light beige oil.

The ester was taken up in MeOH (15 mL) then treated with 6 N NaOH (5 ml, 30.0 mmol). The reaction was heated to reflux (80° C. oil bath) and stirred for 2 h. LCMS showed that the reaction was complete. The reaction was cooled to room temperature then acidified with 6 N HCl (5 mL). The organic solvents were removed by evaporation under vacuum. The remaining slurry was diluted with cold water, filtered, washed with cold water, and dried under vacuum to give 5-bromo-2-methyl-3-(2-methylpyrrolidin-1-yl)benzoic acid (0.52 g, 1.744 mmol, 85% yield) as an off-white solid. $^1$H NMR (400 MHz, DMSO-d₆) δ=13.12 (br. s., 1H), 7.41 (d, J=2.0 Hz, 1H), 7.23 (d, J=2.0 Hz, 1H), 3.74-3.59 (m, 1H), 3.55-3.45 (m, 1H), 2.69 (td, J=4.0, 8.7 Hz, 1H), 2.28 (s, 3H), 2.20-2.08 (m, 1H), 1.88 (tt, J=4.1, 7.7 Hz, 1H), 1.83-1.67 (m, 1H), 1.51 (dq, J=8.9, 11.9 Hz, 1H), 0.92 (d, J=5.8 Hz, 3H). MS(ES)+ m/e 298.1 [M+H]⁺.

b) 5-bromo-N-((4,6-dimethyl-2-oxo-1,2-dihydropyridin-3-yl)methyl)-2-methyl-3-(2-methylpyrrolidin-1-yl)benzamide

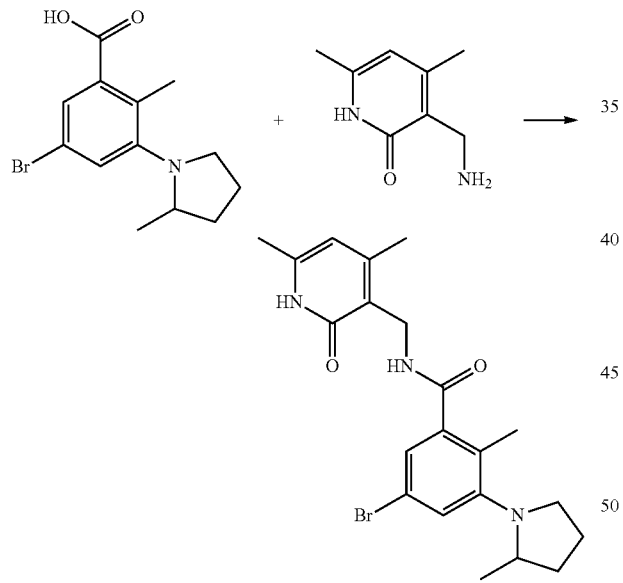

To a mixture of 5-bromo-2-methyl-3-(2-methylpyrrolidin-1-yl)benzoic acid (250 mg, 0.838 mmol), 3-(aminomethyl)-4,6-dimethylpyridin-2(1H)-one hydrochloride salt (160 mg, 0.848 mmol) and HOAt (110 mg, 0.808 mmol) in dichloromethane (DCM) (15 mL) was added N-methylmorpholine (100 µL, 0.910 mmol), followed by EDC free base (150 mg, 0.966 mmol). The reaction was stirred at room temperature for 18 h. LCMS showed that the reaction was complete. The reaction was concentrated under vacuum then purified by silica gel chromatography (Analogix, SF25-40 g, 0 to 4% MeOH in CH₂Cl₂) to give 5-bromo-N-((4,6-dimethyl-2-oxo-1,2-dihydropyridin-3-yl)methyl)-2-methyl-3-(2-methylpyrrolidin-1-yl)benzamide (323 mg, 0.747 mmol, 89% yield), after trituration with 20% CH₂Cl₂ in hexanes, filtration, and drying under vacuum as an off-white solid. $^1$H NMR (400 MHz, DMSO-d₆) δ=11.48 (s, 1H), 8.22 (t, J=4.8 Hz, 1H), 7.07 (d, J=2.0 Hz, 1H), 6.93 (d, J=2.0 Hz, 1H), 5.86 (s, 1H), 4.24 (d, J=5.1 Hz, 2H), 3.70-3.58 (m, 1H), 3.53-3.44 (m, 1H), 2.70 (td, J=3.8, 8.7 Hz, 1H), 2.19 (s, 3H), 2.17-2.12 (m, 1H), 2.11 (s, 3H), 2.08 (s, 3H), 1.92-1.80 (m, 1H), 1.80-1.68 (m, 1H), 1.56-1.43 (m, 1H), 0.92 (d, J=5.8 Hz, 3H). MS(ES)+ m/e 432.2 [M+H]⁺.

Example 19

5-Bromo-N-((4,6-dimethyl-2-oxo-1,2-dihydropyridin-3-yl)methyl)-2-methyl-3-(2-methylpiperidin-1-yl)benzamide

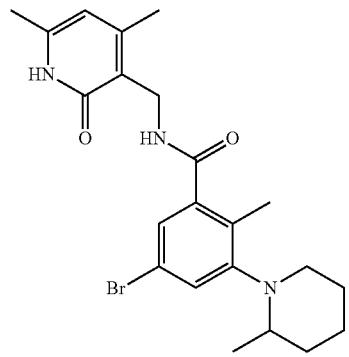 [SMILES: Cc1cc(C)c(CNC(=O)c2cc(Br)cc(N3CCCCC3C)c2C)c(=O)[nH]1]

a) 5-Bromo-2-methyl-3-(2-methylpiperidin-1-yl) benzoic acid

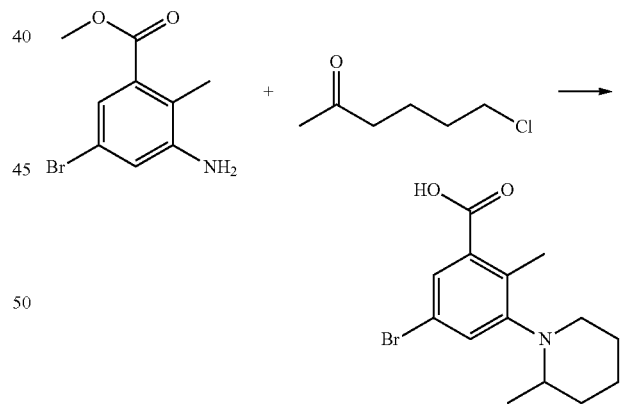

To a stirred solution of methyl 3-amino-5-bromo-2-methylbenzoate (0.5 g, 2.048 mmol) in methanol (20 mL) was added 6-chlorohexan-2-one (3.5 ml, 26.5 mmol), followed by zinc chloride (0.85 g, 6.24 mmol). The reaction was stirred at room temperature for 2 h. The reaction was treated with sodium cyanoborohydride (0.7 g, 11.14 mmol) portionwise (gas evolution) then heated to 40° C. and stirred overnight for 18 h. The reaction was then heated to reflux (80° C. oil bath) and stirred overnight. The reaction was evaporated to dryness, taken up in EtOAc, washed with aq. NH₄Cl, 1 N Na₂CO₃, brine, dried (Na₂SO₄), filtered, and evaporated to dryness. Purification by silica gel chromatography (Analogix, SF25-60 g, 0 to 10% EtOAc in hexanes) gave the crude methyl ester (0.59 g) as a light orange oil, contaminated with some UV negative material (most likely the excess 6-chlorohexan-2-one).

The crude ester was taken up in MeOH (12 mL) and THF (4 mL), then treated with 6 N NaOH (5 ml, 30.0 mmol). The reaction was heated to reflux for 2 h. The reaction was cooled to RT then acidified with 6 N HCl (5 mL). The organic solvents were removed by evaporation under vacuum. The remaining slurry was diluted with cold water, filtered, washed with cold water, and dried under vacuum to give 5-bromo-2-methyl-3-(2-methylpiperidin-1-yl)benzoic acid (0.40 g, 1.281 mmol, 62.5% yield) as an off-white solid. $^1$H NMR (400 MHz, DMSO-$d_6$) δ=13.15 (br. s., 1H), 7.59 (d, J=2.0 Hz, 1H), 7.44 (s, 1H), 3.12-2.97 (m, 1H), 2.85 (d, J=11.1 Hz, 1H), 2.50-2.43 (m, 1H), 2.38 (s, 3H), 1.83-1.67 (m, 2H), 1.66-1.53 (m, 2H), 1.51-1.26 (m, 2H), 0.76 (d, J=6.3 Hz, 3H). MS(ES)+ m/e 312.1 [M+H]$^+$.

b) 5-bromo-N-((4,6-dimethyl-2-oxo-1,2-dihydropyridin-3-yl)methyl)-2-methyl-3-(2-methylpiperidin-1-yl)benzamide

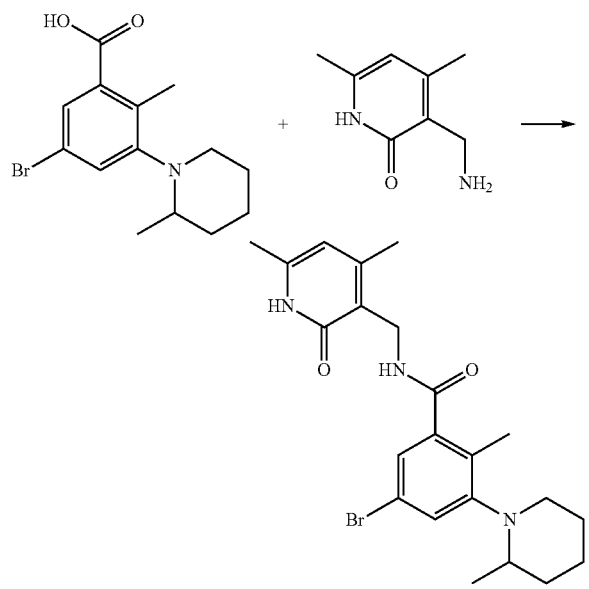

To a mixture of 5-bromo-2-methyl-3-(2-methylpiperidin-1-yl)benzoic acid (250 mg, 0.801 mmol), 3-(aminomethyl)-4,6-dimethylpyridin-2(1H)-one hydrochloride salt (160 mg, 0.848 mmol) and HOAt (110 mg, 0.808 mmol) in dichloromethane (DCM) (15 mL) was added N-methylmorpholine (100 μL, 0.910 mmol), followed by EDC free base (150 mg, 0.966 mmol). The reaction was stirred at room temperature for 18 h. LCMS showed that the reaction was complete. The reaction was concentrated under vacuum then purified by silica gel chromatography (Analogix, SF25-40 g, 0 to 4% MeOH in CH$_2$Cl$_2$) to give 5-bromo-N-((4,6-dimethyl-2-oxo-1,2-dihydropyridin-3-yl)methyl)-2-methyl-3-(2-methylpiperidin-1-yl)benzamide (268 mg, 0.600 mmol, 75.0% yield), after trituration with 20% CH$_2$Cl$_2$ in hexanes, filtration, and drying under vacuum as an off-white solid. $^1$H NMR (400 MHz, DMSO-$d_6$) δ=11.48 (s, 1H), 8.23 (t, J=4.9 Hz, 1H), 7.26 (d, J=1.8 Hz, 1H), 7.09 (d, J=2.0 Hz, 1H), 5.86 (s, 1H), 4.24 (d, J=5.1 Hz, 2H), 3.08-2.96 (m, 1H), 2.84 (d, J=11.4 Hz, 1H), 2.49-2.39 (m, 1H), 2.18 (s, 3H), 2.16 (s, 3H), 2.11 (s, 3H), 1.81-1.66 (m, 2H), 1.64-1.52 (m, 2H), 1.48-1.25 (m, 2H), 0.77 (d, J=6.1 Hz, 3H). MS(ES)+ m/e 446.3 [M+H]$^+$.

Example 20

5-Bromo-3-(sec-butoxy)-N-((4,6-dimethyl-2-oxo-1,2-dihydropyridin-3-yl)methyl)-2-methylbenzamide

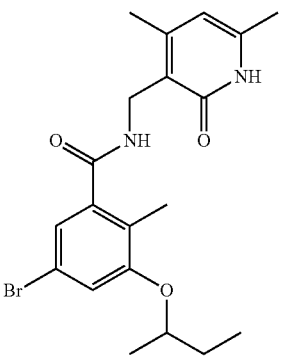 [SMILES: CCC(C)Oc1cc(Br)cc(C(=O)NCc2c(C)cc(C)[nH]c2=O)c1C]

a) 3-Amino-5-bromo-2-methylbenzoic acid

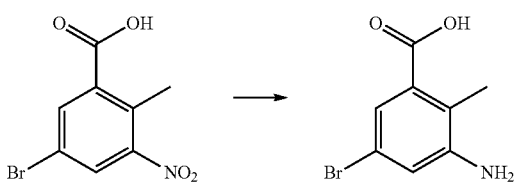

To a mechanically stirred mixture of 5-bromo-2-methyl-3-nitrobenzoic acid (4.0 g, 15.38 mmol) and ammonium chloride (8.0 g, 149.6 mmol) in ethanol (80 mL) and water (80 mL) was added iron powder (2.8 g, 50.1 mmol). The reaction mixture was heated to reflux (70° C. oil bath) and stirred for 18 hr. The reaction mixture was diluted with EtOH (80 mL), filtered through a pad of Celite, washed with EtOH (40 mL) and evaporated to near dryness under vacuum. The remaining brown residue was triturated with a small volume of water, filtered, washed with cold water, and dried under vacuum to give 3-amino-5-bromo-2-methylbenzoic acid (2.70 g, 11.7 mmol, 76% yield) as a beige solid. $^1$H NMR (400 MHz, MeOH-$d_4$) δ=7.16 (br. s., 1H), 7.00 (br. s., 1H), 2.26 (br. s., 3H). MS(ES)+ m/e 230.0 [M+H]$^+$.

b) 5-Bromo-3-hydroxy-2-methylbenzoic acid

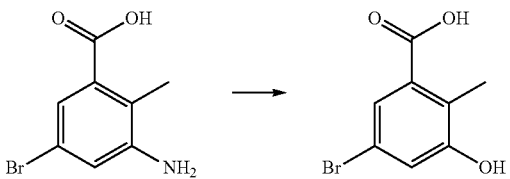

To a stirred suspension of 3-amino-5-bromo-2-methyl-benzoic acid (1.0 g, 4.35 mmol) in 10% H₂SO₄ (10 mL) at 0° C. in an ice bath was added dropwise a solution of sodium nitrite (0.300 g, 4.35 mmol) in water (2.0 mL). The reaction mixture was stirred for 1 hr. A solution of 50% H₂SO₄ in water (10 mL) was added and the reaction mixture was heated to 100° C. and stirred for 1 hr. The reaction mixture was poured into ice water (100 mL), stirred for 30 minutes, filtered, washed with water, and dried under vacuum to give 5-bromo-3-hydroxy-2-methylbenzoic acid (0.65 g, 2.81 mmol, 64.9% yield) as an orange solid. $^1$H NMR (400 MHz, DMSO-$d_6$) δ=13.10 (br. s., 1H), 10.17 (s, 1H), 7.30 (d, J=2.0 Hz, 1H), 7.11 (d, J=2.0 Hz, 1H), 2.25 (s, 3H). MS(ES)+ m/e 230.9 $[M+H]^+$.

c) Methyl 5-bromo-3-(sec-butoxy)-2-methylbenzoate

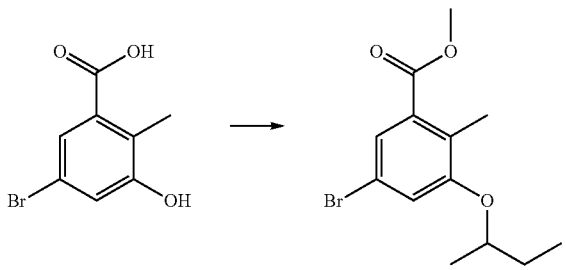 [SMILES: Cc1c(O)cc(Br)cc1C(=O)O ; CCC(C)Oc1cc(Br)cc(C(=O)OC)c1C]

To methanol (20 mL) with stirring at 0° C. in an ice bath was added dropwise thionyl chloride (0.65 mL, 8.91 mmol). The reaction mixture was stirred for 10 minutes, then 5-bromo-3-hydroxy-2-methylbenzoic acid (0.40 g, 1.731 mmol) was added. The reaction mixture was allowed to warm to room temperature and stirred overnight. The reaction mixture was evaporated to dryness. Re-evaporation from toluene gave the crude methyl ester as a yellow-orange solid. The ester was taken up in N,N-Dimethylformamide (DMF) (10 mL) and treated with cesium carbonate (0.7 g, 2.148 mmol), followed by 2-iodobutane (0.28 mL, 2.431 mmol). The reaction mixture was stirred at room temperature over the weekend. Another 0.50 g of cesium carbonate and 0.20 mL 2-iodobutane were added and the reaction stirred for another 18 hrs at 40° C. The reaction mixture was evaporated to dryness, taken up in EtOAc, washed with water, brine, dried (MgSO₄), filtered, and evaporated to dryness. Purification by silica gel (Analogix, SF25-40 g, 0 to 10% EtOAc in hexanes) gave methyl 5-bromo-3-(sec-butoxy)-2-methylbenzoate (0.35 g, 1.162 mmol, 67.1% yield) as a clear oil. $^1$H NMR (400 MHz, CHCl₃-d) δ=7.53 (d, J=1.8 Hz, 1H), 7.09 (d, J=2.0 Hz, 1H), 4.30 (sxt, J=6.0 Hz, 1H), 3.90 (s, 3H), 2.37 (s, 3H), 1.85-1.61 (m, 2H), 1.32 (d, J=6.1 Hz, 3H), 1.00 (t, J=7.5 Hz, 3H). MS(ES)+ m/e 301.1 $[M+H]^+$.

d) 5-Bromo-3-(sec-butoxy)-2-methylbenzoic acid

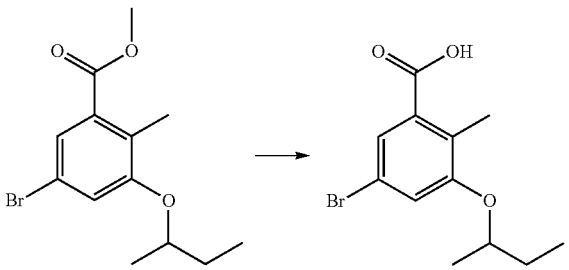 [SMILES: CCC(C)Oc1cc(Br)cc(C(=O)OC)c1C ; CCC(C)Oc1cc(Br)cc(C(=O)O)c1C]

To a stirred solution of methyl 5-bromo-3-(sec-butoxy)-2-methylbenzoate (350 mg, 1.162 mmol) in methanol (20 mL) was added 1 N NaOH (5.0 mL, 5.00 mmol). The reaction mixture was stirred at 60° C. for 2 hr. The reaction mixture was acidified with 1 N HCl (5 mL) and concentrated to near dryness under vacuum. The remaining suspension was triturated with water, filtered, and dried under vacuum to give 5-bromo-3-(sec-butoxy)-2-methylbenzoic acid (340 mg, 1.184 mmol, 102% yield (existence of residual solvent or small amount of impurities)) as a white solid. $^1$H NMR (400 MHz, DMSO-$d_6$) δ=13.22 (br. s., 1H), 7.40 (d, J=1.8 Hz, 1H), 7.32 (d, J=1.8 Hz, 1H), 4.50 (sxt, J=5.9 Hz, 1H), 2.26 (s, 3H), 1.74-1.55 (m, 2H), 1.22 (d, J=5.8 Hz, 3H), 0.93 (t, J=7.3 Hz, 3H). MS(ES)+ m/e 287.0 $[M+H]^+$.

e) 5-Bromo-3-(sec-butoxy)-N-((4,6-dimethyl-2-oxo-1,2-dihydropyridin-3-yl)methyl)-2-methylbenzamide

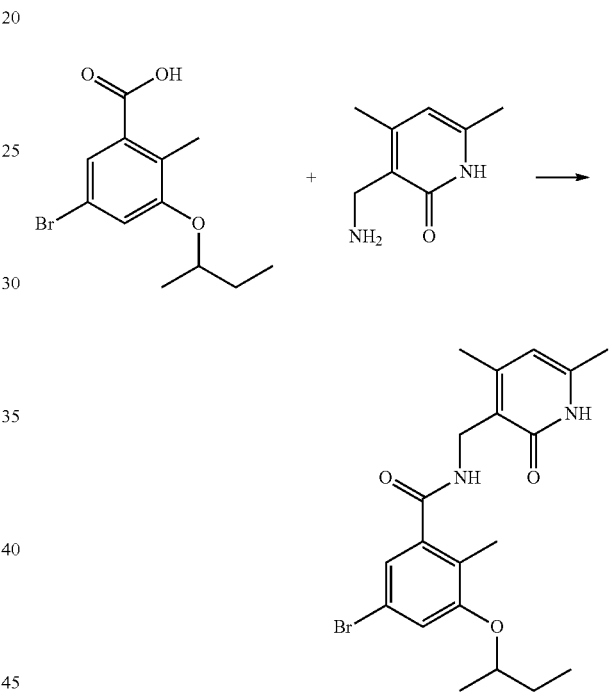

To a mixture of 5-bromo-3-(sec-butoxy)-2-methylbenzoic acid (335 mg, 1.167 mmol), 3-(aminomethyl)-4,6-dimethylpyridin-2(1H)-one hydrochloride salt (242 mg, 1.283 mmol) and HOAt (159 mg, 1.167 mmol) in dichloromethane (DCM) (15 mL) was added N-methylmorpholine (0.141 mL, 1.283 mmol) followed by EDC free base (217 mg, 1.400 mmol). The reaction mixture was stirred at RT for 3 hr. The reaction mixture was concentrated under vacuum then purified by silica gel chromatography (Analogix, SF25-40 g, 0 to 5% MeOH in CH₂Cl₂; loaded as a suspension in CH₂Cl₂) to give 5-bromo-3-(sec-butoxy)-N-((4,6-dimethyl-2-oxo-1,2-dihydropyridin-3-yl)methyl)-2-methylbenzamide (346 mg, 0.821 mmol, 70.4% yield) as a white solid, after trituration with 5% MeOH in water, filtration, and drying under vacuum. $^1$H NMR (400 MHz, DMSO-$d_6$) δ=11.47 (br. s., 1H), 8.24 (t, J=4.9 Hz, 1H), 7.15 (d, J=1.8 Hz, 1H), 6.92 (d, J=1.8 Hz, 1H), 5.86 (s, 1H), 4.45 (sxt, J=5.9 Hz, 1H), 4.24 (d, J=5.1 Hz, 2H), 2.18 (s, 3H), 2.11 (s, 3H), 2.04 (s, 3H), 1.70-1.52 (m, 2H), 1.21 (d, J=6.1 Hz, 3H), 0.92 (t, J=7.5 Hz, 3H). MS(ES)+ m/e 421.2 $[M+H]^+$.

Example 21

5-Bromo-N-((4,6-dimethyl-2-oxo-1,2-dihydropyridin-3-yl)methyl)-3-isopropoxy-2-methylbenzamide

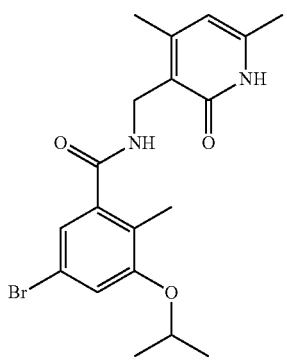

a) Methyl 5-bromo-3-isopropoxy-2-methylbenzoate

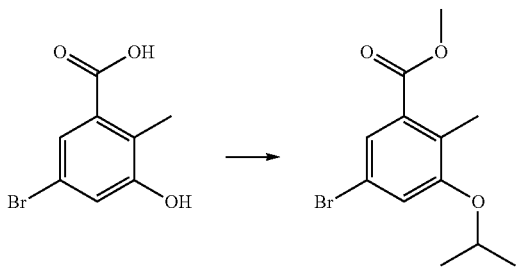 [SMILES: Cc1c(O)cc(Br)cc1C(=O)O ; COC(=O)c1cc(Br)cc(OC(C)C)c1C]

To methanol (20 mL) with stirring at 0° C. in an ice bath was added dropwise thionyl chloride (0.65 mL, 8.91 mmol). The reaction mixture was stirred for 10 minutes, then 5-bromo-3-hydroxy-2-methylbenzoic acid (0.40 g, 1.731 mmol) was added. The reaction mixture was allowed to warm to room temperature and stirred overnight. The reaction mixture was evaporated to dryness. Re-evaporation from toluene gave the crude methyl ester as a beige solid. The ester was taken up in N,N-dimethylformamide (DMF) (10 mL) and treated with cesium carbonate (0.7 g, 2.148 mmol), followed by 2-iodopropane (0.28 mL, 2.63 mmol). The reaction mixture was stirred at 40° C. for 18 hr. The reaction mixture was evaporated to dryness, taken up in EtOAc, washed with water, brine, dried (MgSO$_4$), filtered, and evaporated to dryness. Purification by silica gel (Analogix, SF25-40 g, 0 to 10% EtOAc in hexanes) gave methyl 5-bromo-3-isopropoxy-2-methylbenzoate (0.45 g, 1.567 mmol, 91% yield) as a clear oil. $^1$H NMR (400 MHz, CHCl$_3$-d) δ=7.54 (d, J=2.0 Hz, 1H), 7.11 (d, J=2.0 Hz, 1H), 4.58-4.44 (m, 1H), 3.90 (s, 3H), 2.36 (s, 3H), 1.37 (d, J=6.1 Hz, 6H). MS(ES)+ m/e 287.0 [M+H]$^+$.

b) 5-Bromo-3-isopropoxy-2-methylbenzoic acid

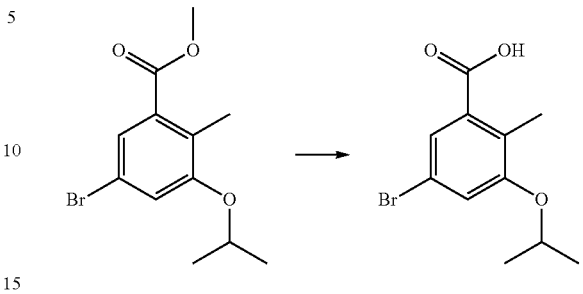

To a stirred solution of methyl 5-bromo-3-isopropoxy-2-methylbenzoate (450 mg, 1.567 mmol) in methanol (20 mL) was added 1 N NaOH (5.0 mL, 5.00 mmol). The reaction mixture was stirred at 60° C. for 2 hr. The reaction mixture was acidified with 1N HCl (5 mL) and concentrated to near dryness under vacuum. The remaining suspension was triturated with water, filtered, and dried under vacuum to give 5-bromo-3-isopropoxy-2-methylbenzoic acid (440 mg, 1.611 mmol, 103% yield (existence of residual solvent or small amount of impurities)) as a white solid. $^1$H NMR (400 MHz, DMSO-d$_6$) δ=13.26 (br. s., 1H), 7.40 (d, J=2.0 Hz, 1H), 7.32 (d, J=2.0 Hz, 1H), 4.68 (spt, J=6.0 Hz, 1H), 2.25 (s, 3H), 1.27 (d, J=6.1 Hz, 6H). MS(ES)+ m/e 273.0 [M+H]$^+$.

c) 5-Bromo-N-((4,6-dimethyl-2-oxo-1,2-dihydropyridin-3-yl)methyl)-3-isopropoxy-2-methylbenzamide

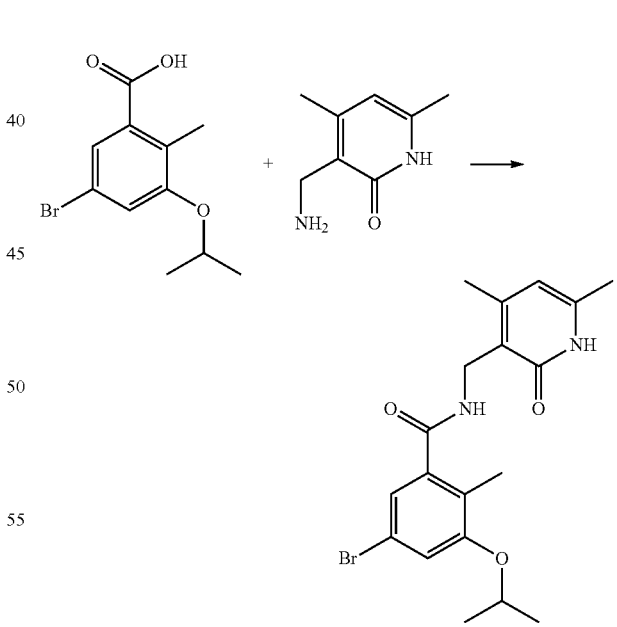

To a mixture of 5-bromo-3-isopropoxy-2-methylbenzoic acid (430 mg, 1.574 mmol), 3-(aminomethyl)-4,6-dimethylpyridin-2(1H)-one hydrochloride salt (327 mg, 1.732 mmol) and HOAt (214 mg, 1.574 mmol) in dichloromethane (DCM) (15 mL) was added N-methylmorpholine (0.190 mL, 1.732 mmol), followed by EDC free base (293 mg, 1.889 mmol). The reaction mixture was stirred at RT for 3 hr. The reaction mixture was concentrated under vacuum then purified by silica gel chromatography (Analogix, SF25-40 g, 0 to 5% MeOH in $CH_2Cl_2$; loaded as a suspension in $CH_2Cl_2$) to give 5-bromo-N-((4,6-dimethyl-2-oxo-1,2-dihydropyridin-3-yl)methyl)-3-isopropoxy-2-methylbenzamide (334 mg, 0.820 mmol, 52.1% yield) as a white solid, after trituration with water, filtration, and drying under vacuum. $^1$H NMR (400 MHz, DMSO-$d_6$) δ=11.48 (br. s., 1H), 8.24 (t, J=4.9 Hz, 1H), 7.17 (d, J=1.8 Hz, 1H), 6.93 (d, J=1.8 Hz, 1H), 5.86 (s, 1H), 4.64 (dt, J=6.0, 12.1 Hz, 1H), 4.24 (d, J=5.1 Hz, 2H), 2.18 (s, 3H), 2.11 (s, 3H), 2.03 (s, 3H), 1.26 (d, J=5.8 Hz, 6H). MS(ES)+ m/e 407.1 [M+H]$^+$.

Example 22

3-[Acetyl(1-methylpropyl)amino]-5-bromo-N-[(4,6-dimethyl-2-oxo-1,2-dihydro-3-pyridinyl)methyl]-2-methylbenzamide

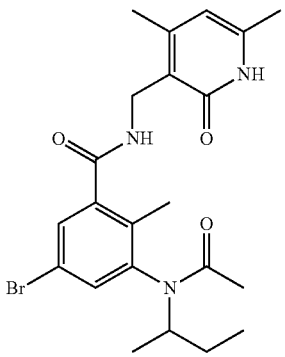

a) Methyl 3-[acetyl(1-methylpropyl)amino]-5-bromo-2-methylbenzoate

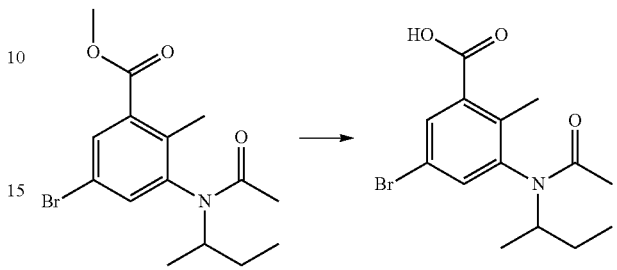

To methyl 5-bromo-3-(sec-butylamino)-2-methylbenzoate (0.50 g, 1.666 mmol) was added acetic anhydride (10 ml, 106 mmol). The reaction was stirred and heated at 100° C. for 18 hr. LCMS showed that the reaction was complete. The reaction was evaporated to dryness under vacuum. Purified by silica gel chromatography (Analogix, SF25-60 g, 0 to 40% EtOAc in hexanes) to give the product methyl 5-bromo-3-(N-(sec-butyl)acetamido)-2-methylbenzoate (0.57 g, 1.666 mmol, 100% yield) as a clear oil. $^1$H NMR (400 MHz, DMSO-$d_6$) (amide rotomers) δ=7.98 and 7.95 (2d, J=2.0 Hz, 1H), 7.69 and 7.57 (2d, J=2.0 Hz, 1H), 4.53-4.45 and 4.30-4.23 (2m, 1H), 3.86 (s, 3H), 2.31 and 2.29 (2s, 3H), 1.68-1.62 and 1.52-1.44 (2m, 1H), 1.60 and 1.14 (2d, J=6.6 Hz, 3H), 1.43-1.31 and 1.03-0.94 (2m, 1H), 0.89 and 0.80 (2t, J=7.5 Hz, 3H). MS(ES) [M+H]$^+$ 342.1.

b) 3-[Acetyl(1-methylpropyl)amino]-5-bromo-2-methylbenzoic acid

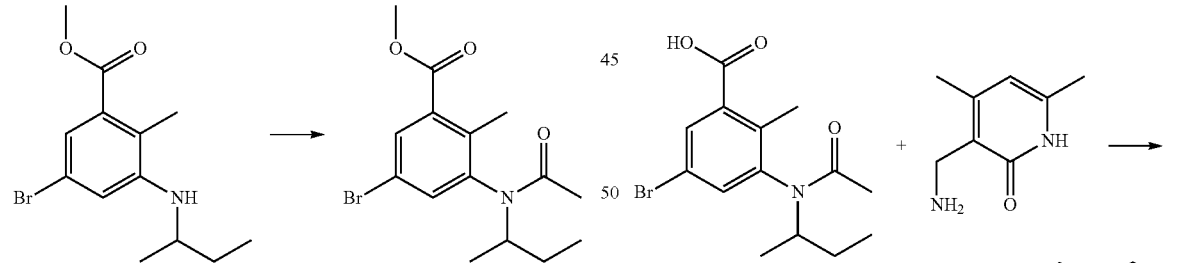

To a stirred solution of methyl 5-bromo-3-(N-(sec-butyl)acetamido)-2-methylbenzoate (0.55 g, 1.607 mmol) in methanol (15 mL) was added 6 N sodium hydroxide (2.0 mL, 12.00 mmol). The reaction was stirred at 60° C. for 2 hr. LCMS showed that the reaction was complete. The reaction was acidified with 6 N HCl (2 mL) then evaporated to remove methanol. The remaining was diluted with water, extracted with $CH_2Cl_2$, dried (MgSO$_4$), filtered, and evaporated to dryness. Re-evaporation from hexanes gave the product 5-bromo-3-(N-(sec-butyl)acetamido)-2-methylbenzoic acid (0.50 g, 1.523 mmol, 95% yield) as a white solid foam. $^1$H NMR (400 MHz, DMSO-$d_6$) (amide rotomers) δ=13.46 (br. s., 1H), 7.95 and 7.93 (2d, J=2.0 Hz, 1H), 7.64 and 7.52 (2d, J=2.0 Hz, 0H), 4.49 and 4.24 (2dq, J=6.8, 14.1 Hz, 1H), 2.32 and 2.30 (2s, 3H), 1.70-1.60 and 1.54-1.43 (2m, 1H), 1.60-1.14 (2d, J=6.6 Hz, 3H), 1.43-1.24 and 1.06-0.94 (2m, 1H), 0.89 and 0.80 (2t, J=7.3 Hz, 3H). MS(ES) [M+H]$^+$ 328.1.

c) 3-[Acetyl(1-methylpropyl)amino]-5-bromo-N-[(4,6-dimethyl-2-oxo-1,2-dihydro-3-pyridinyl)methyl]-2-methylbenzamide

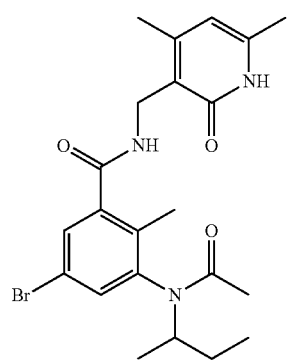 [SMILES: CCC(C)N(C(C)=O)c1cc(Br)cc(C(=O)NCc2c(C)cc(C)[nH]c2=O)c1C]

To a mixture of 5-bromo-3-(N-(sec-butyl)acetamido)-2-methylbenzoic acid (250 mg, 0.762 mmol), 3-(aminomethyl)-4,6-dimethylpyridin-2(1H)-one hydrochloride salt (160 mg, 0.848 mmol) and HOAt (110 mg, 0.808 mmol) in Dichloromethane (DCM) (15 mL) was added N-methylmorpholine (100 μL, 0.910 mmol) followed by EDC free base (150 mg, 0.966 mmol). The reaction was stirred at room temperature for 4 hr. LCMS showed that the reaction was complete. The reaction was concentrated under vacuum then purified by silica gel chromatography (Analogix, SF25-60 g, 0 to 5% MeOH in $CH_2Cl_2$) to give the product 5-bromo-3-(N-(sec-butyl)acetamido)-N-((4,6-dimethyl-2-oxo-1,2-dihydropyridin-3-yl)methyl)-2-methylbenzamide (310 mg, 0.670 mmol, 88% yield), after trituration with 10% $CH_2Cl_2$ in hexanes, filtration, and drying under vacuum as an off-white solid. $^1$H NMR (400 MHz, DMSO-$d_6$) (amide rotomers) δ=11.51 (br. s., 1H), 8.45 (q, J=5.1 Hz, 1H), 7.43 (td, J=2.0, 7.6 Hz, 1H), 7.34 (d, J=2.0 Hz, 1H), 5.87 (s, 1H), 4.49-4.41 and 4.20-4.16 (2m, 1H), 4.26 (d, J=4.8 Hz, 2H), 2.20 (s, 3H), 2.12 (s, 3H), 2.09 and 2.07 (2s, 3H), 1.13 and 0.80 (2d, J=6.82, 3H), 0.89 and 0.81 (2t, J=7.4, 3H). MS(ES) [M+H]$^+$ 462.2.

Example 23

2,5-Dichloro-N-[(4,6-dimethyl-2-oxo-1,2-dihydro-3-pyridinyl)methyl]-3-[(1-methylpropyl)amino]benzamide

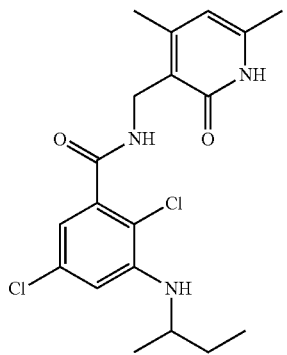 [SMILES: CCC(C)Nc1cc(Cl)cc(C(=O)NCc2c(C)cc(C)[nH]c2=O)c1Cl]

a) Methyl 3-amino-2,5-dichlorobenzoate

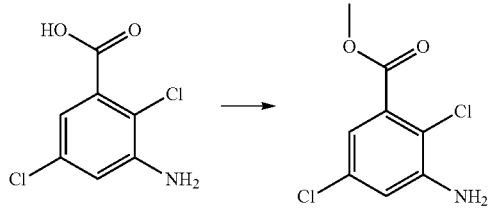

To methanol (50 mL) with stirring at 0° C. was slowly added thionyl chloride (4.0 mL, 54.8 mmol) dropwise. After stirring for 15 minutes 3-amino-2,5-dichlorobenzoic acid (2.5 g, 12.13 mmol) was added. The reaction was allowed to warm to RT and stirred for 24 hr. LCMS showed that the reaction was 59% complete. The reaction was heated to reflux (70° C. oil bath) and stirred for 5 hr. LCMS now showed that the reaction was complete. The reaction was evaporated to dryness, taken up in EtOAc, washed with 1N $Na_2CO_3$, brine, dried ($Na_2SO_4$), filtered and evaporated to dryness to give the product methyl 3-amino-2,5-dichlorobenzoate (2.63 g, 11.95 mmol, 98% yield) as a beige oil (solidified under vacuum). $^1$H NMR (400 MHz, DMSO-$d_6$) δ=6.98 (d, J=2.5 Hz, 1H), 6.88 (d, J=2.5 Hz, 1H), 5.99 (s, 2H), 3.83 (s, 3H). MS(ES) [M+H]$^+$ 220.0.

b) Methyl 2,5-dichloro-3-[(1-methylpropyl)amino]benzoate

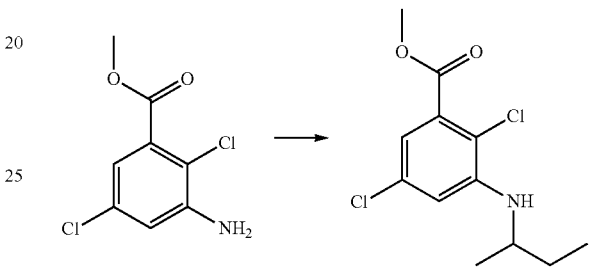

In a 20 mL microwave vial was added methyl 3-amino-2,5-dichlorobenzoate (500 mg, 2.272 mmol), DIEA (0.5 mL, 2.86 mmol), 2-iodobutane (1.0 mL, 8.68 mmol) and Dimethyl Sulfoxide (DMSO) (0.5 mL). The vial was capped and stirred at 100° C. for 24 hr. LCMS showed 36% product and 19% starting material (45% of an unknown). Purification by silica gel chromatography (Analogix, SF25-60 g, 0 to 15% EtOAc in hexanes) gave the product methyl 3-(sec-butylamino)-2,5-dichlorobenzoate (180 mg, 0.652 mmol, 28.7% yield) as a clear oil. LCMS showed that it was 91% pure. H-NMR was messy (~70% pure). Used as is in the next reaction. $^1$H NMR (400 MHz, DMSO-$d_6$) δ=6.91 (d, J=2.5 Hz, 1H), 6.88 (d, J=2.3 Hz, 1H), 5.33 (d, J=8.6 Hz, 1H), 3.84 (s, 3H), 3.57-3.49 (m, 1H), 1.60 (dq, J=6.9, 14.1 Hz, 1H), 1.55-1.44 (m, 1H), 1.14 (d, J=6.3 Hz, 3H), 0.89 (t, J=7.5 Hz, 3H). MS(ES) [M+H]$^+$ 276.1.

c) 2,5-Dichloro-N-[(4,6-dimethyl-2-oxo-1,2-dihydro-3-pyridinyl)methyl]-3-[(1-methylpropyl)amino]benzamide

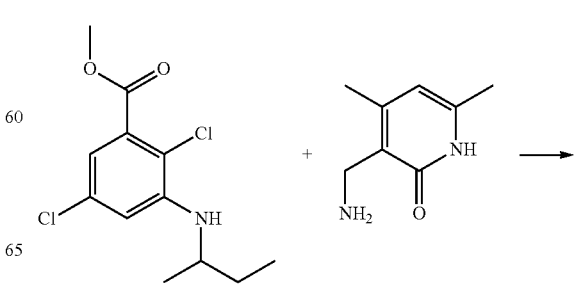

85

-continued

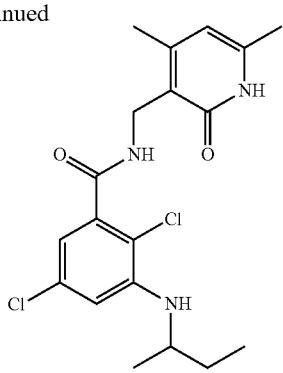

To a stirred solution of methyl 3-(sec-butylamino)-2,5-dichlorobenzoate (180 mg, 0.652 mmol) in methanol (15 mL) was added 1N sodium hydroxide (2.5 mL, 2.500 mmol). The reaction was stirred at room temperature over the weekend. LCMS showed that the reaction was complete. The reaction was evaporated under vacuum to remove the methanol then acidified with 1N HCl (2.5 mL). The sticky solid that separated was extracted with $CH_2Cl_2$, dried ($MgSO_4$), filtered and concentrated under vacuum to give the crude carboxylic acid.

To a stirred mixture of the above acid, 3-(aminomethyl)-4,6-dimethylpyridin-2(1H)-one hydrochloride salt (135 mg, 0.717 mmol) and HOAt (90 mg, 0.661 mmol) in Dichloromethane (DCM) (20 mL) was added N-methylmorpholine (80 µL, 0.728 mmol) followed by EDC free base (125 mg, 0.805 mmol). The reaction was stirred at room temperature overnight for 18 hr. LCMS showed that the reaction was complete. The reaction was concentrated under vacuum and purified by silica gel chromatography (Analogix, SF25-80 g, 0 to 4% MeOH in $CH_2Cl_2$). TLC of the fractions showed a very closely eluting lower spot which partially separated out. The fractions containing what appeared as pure were combined, evaporated to dryness, triturated with hexanes, filtered, and dried under vacuum to give the product as a white solid. LCMS showed a very closely eluting impurity that did not separate (~70% pure).

This crude product was re-purified by preparative chiral HPLC on a Chiralcel OJ-H, 5 microns (30 mm×250 mm) column eluted with (80:20) n-heptane, ethanol. Carried out 10 prep runs. Collected the pure product fractions and evaporated under vacuum at 50° C. to a constant weight. The product 3-(sec-butylamino)-2,5-dichloro-N-((4,6-dimethyl-2-oxo-1,2-dihydropyridin-3-yl)methyl)benzamide (119 mg, 0.30 mmol, 46.0% yield) was obtained as a white solid. $^1$H NMR (400 MHz, DMSO-$d_6$) δ=11.48 (s, 1H), 8.33 (t, J=4.9 Hz, 1H), 6.74 (d, J=2.3 Hz, 1H), 6.48 (d, J=2.3 Hz, 1H), 5.86 (s, 1H), 5.12 (d, J=8.6 Hz, 1H), 4.24 (d, J=5.1 Hz, 2H), 3.54-3.43 (m, 1H), 2.18 (s, 3H), 2.11 (s, 3H), 1.65-1.53 (m, 1H), 1.53-1.42 (m, 1H), 1.13 (d, J=6.3 Hz, 3H), 0.88 (t, J=7.3 Hz, 3H). MS(ES) [M+H]$^+$ 396.1.

86

Example 24

2,5-Dichloro-N-[(4,6-dimethyl-2-oxo-1,2-dihydro-3-pyridinyl)methyl]-3-[(1-methylethyl)oxy]benzamide

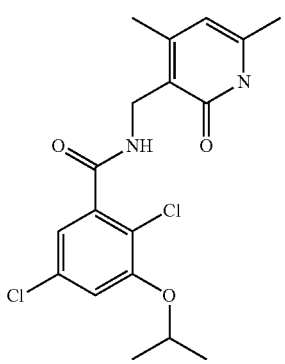 [SMILES: Cc1cc(C)c(CNC(=O)c2cc(Cl)cc(OC(C)C)c2Cl)c(=O)[nH]1]

a) 2,5-Dichloro-3-iodobenzoic acid

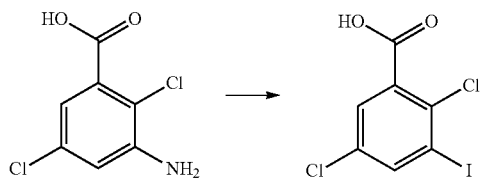 [SMILES: Nc1cc(Cl)cc(C(=O)O)c1Cl ; O=C(O)c1cc(Cl)cc(I)c1Cl]

To a stirred solution of iodine (4.84 g, 19.08 mmol) in DMSO (9.0 mL) was added t-butylnitrile (3.4 ml, 28.6 mmol). A solution of 3-amino-2,5-dichlorobenzoic acid (3.93 g, 19.08 mmol) in DMSO (13 mL) was then added slowly dropwise to the above. Exothermic (Do not let the temperature rise above 50° C.). Stopped halfway through to let the reaction cool down. (Saw gas evolution during addition.) The reaction was allowed to stir overnight at room temperature. The reaction was poured into water and extracted with EtOAc (2×). The EtOAc phases were combined and washed with an aqueous solution of sodium bisulfite, water, dried ($MgSO_4$), filtered, and evaporated to dryness to give the product 2,5-dichloro-3-iodobenzoic acid (5.38 g, 16.98 mmol, 89% yield) as a orange brown solid. The product was 80% pure by LCMS and was used as is in the next reaction. $^1$H NMR (400 MHz, DMSO-$d_6$) δ=13.92 (br. s., 1H), 8.21 (d, J=2.5 Hz, 1H), 7.79 (d, J=2.5 Hz, 1H). MS(ES) [M+H]$^+$ 316.9.

b) 2,5-Dichloro-3-hydroxybenzoic acid

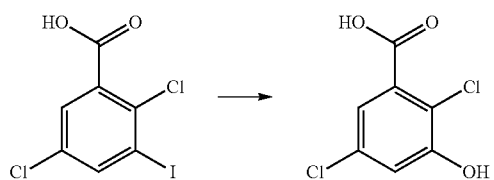 [SMILES: O=C(O)c1cc(Cl)cc(I)c1Cl ; O=C(O)c1cc(Cl)cc(O)c1Cl]

To a flask containing water (100 mL) was added sodium hydroxide (9.7 g, 243 mmol). After the sodium hydroxide was completely dissolved, 2,5-dichloro-3-iodobenzoic acid (5.0 g, 15.78 mmol) was added followed by copper(II) sulfate pentahydrate (2.6 g, 10.41 mmol). The reaction was heated to 100° C. and stirred for 3 hr. LCMS showed that the reaction was mostly complete. The dark reaction was cooled in an ice bath and acidified with conc. HCl (~20 mL). The mixture was extracted with EtOAc, filtered to remove a small amount of insoluble material, washed with water, aq. sodium bisulfite, brine, dried (MgSO$_4$), filtered and evaporated to dryness to give the product 2,5-dichloro-3-hydroxybenzoic acid (3.26 g, 9.76 mmol, 61.9% yield) (62% pure by LCMS) as a orange brown solid. This crude was used as is and was purified in the next step. $^1$H NMR (400 MHz, DMSO-d$_6$) δ=13.59 (br. s., 1H), 11.02 (s, 1H), 7.18 (d, J=2.5 Hz, 1H), 7.10 (d, J=2.5 Hz, 1H). MS(ES) [M+H]$^+$ 206.9.

c) Methyl 2,5-dichloro-3-hydroxybenzoate

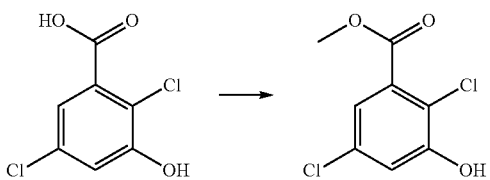

To methanol (100 mL) with stirring at 0° C. was slowly added thionyl chloride (8.0 mL, 110 mmol) dropwise. After stirring for 15 minutes 2,5-dichloro-3-hydroxybenzoic acid (3.25 g, 15.70 mmol) was added. The reaction was allowed to warm to room temperature and stirred for 24 hr. LCMS showed that the reaction was complete. The reaction was evaporated to dryness. Purified by silica gel chromatography (Analogix, SF40-120 g, 0 to 10% EtOAc in hexanes) (Did not dissolve well in CH$_2$Cl$_2$) to give the crude product, which was triturated with hexanes to remove most of the orange color, and dried to give the product methyl 2,5-dichloro-3-hydroxybenzoate (1.83 g, 8.28 mmol, 52.7% yield) as a light orange solid. The colored impurity was removed in the next step. $^1$H NMR (400 MHz, DMSO-d$_6$) δ=11.14 (s, 1H), 7.23 (d, J=2.5 Hz, 1H), 7.15 (d, J=2.5 Hz, 1H), 3.85 (s, 3H). MS(ES) [M+H]$^+$ 221.0.

d) M ethyl 2,5-dichloro-3-[(1-methylethyl)oxy]benzoate

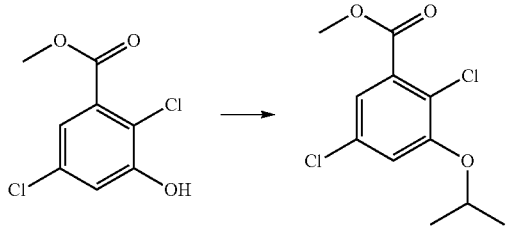 [SMILES: COC(=O)c1cc(Cl)cc(O)c1Cl ; COC(=O)c1cc(Cl)cc(OC(C)C)c1Cl]

To a stirred mixture of methyl 2,5-dichloro-3-hydroxybenzoate (0.6 g, 2.71 mmol) and cesium carbonate (1.1 g, 3.38 mmol) in N,N-Dimethylformamide (DMF) (10 mL) was added 2-iodopropane (0.44 mL, 4.40 mmol). The reaction was stirred overnight at room temperature. LCMS showed that the reaction was complete. The reaction was evaporated to dryness, taken up in EtOAc, washed with water, brine, dried (MgSO$_4$), filtered and concentrated under vacuum, Purified by silica gel chromatography (Analogix, SF25-60 g, 0 to 10% EtOAc in hexanes) to give the product methyl 2,5-dichloro-3-isopropoxybenzoate (0.72 g, 2.74 mmol, 101% yield) as a clear oil. $^1$H NMR (400 MHz, DMSO-d$_6$) δ=7.49 (d, J=2.5 Hz, 1H), 7.35 (d, J=2.3 Hz, 1H), 4.81 (dt, J=6.0, 11.9 Hz, 1H), 3.86 (s, 3H), 1.30 (d, J=6.1 Hz, 6H). MS(ES) [M+H]$^+$ 263.0.

e) 2,5-Dichloro-3-[(1-methylethyl)oxy]benzoic acid

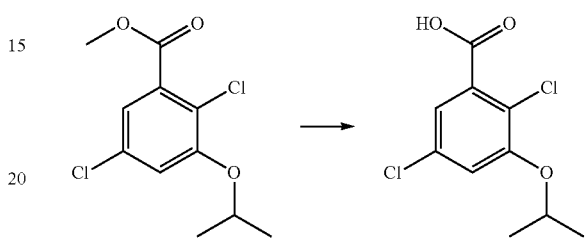

To a stirred solution of methyl 2,5-dichloro-3-isopropoxybenzoate (0.7 g, 2.66 mmol) in methanol (30 mL) was added 1N sodium hydroxide (10 ml, 10.00 mmol). The reaction was heated to 40° C. and stirred for 18 hr. LCMS showed that the reaction was complete. The reaction was concentrated under vacuum to remove the methanol then acidified with 1N HCl (10 mL). The precipitated solid was triturated, filtered, washed with water and dried under vacuum to give the product 2,5-dichloro-3-isopropoxybenzoic acid (643 mg, 2.58 mmol, 97% yield) as an off-white solid. $^1$H NMR (400 MHz, DMSO-d$_6$) δ=13.69 (br. s., 1H), 7.43 (d, J=2.3 Hz, 1H), 7.29 (d, J=2.5 Hz, 1H), 4.80 (dt, J=6.0, 12.1 Hz, 1H), 1.30 (d, J=6.1 Hz, 6H). MS(ES) [M+H]$^+$ 249.0.

f) 2,5-Dichloro-N-[(4,6-dimethyl-2-oxo-1,2-dihydro-3-pyridinyl)methyl]-3-[(1-methylethyl)oxy]benzamide

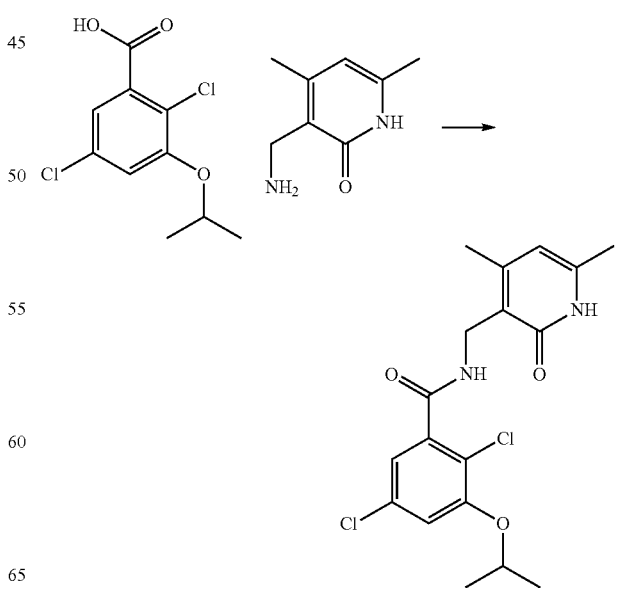

To a stirred mixture of 2,5-dichloro-3-isopropoxybenzoic acid (250 mg, 1.004 mmol), 3-(aminomethyl)-4,6-dimethylpyridin-2(1H)-one hydrochloride salt (220 mg, 1.166 mmol) and HOAt (137 mg, 1.004 mmol) in Dichloromethane (DCM) (20 mL) was added N-methylmorpholine (130 µL, 1.182 mmol) followed by EDC free base (210 mg, 1.353 mmol). The reaction was stirred at room temperature overnight for 18 hr. LCMS showed that the reaction was complete. The reaction was concentrated under vacuum and purified by silica gel chromatography (Analogix, SF25-60 g, 0 to 5% MeOH in $CH_2Cl_2$) (Not real soluble in $CH_2Cl_2$.). The pure fractions were combined, evaporated to dryness, triturated with 5% MeOH in water, filtered, washed with water and dried under vacuum to give the product 2,5-dichloro-N-((4,6-dimethyl-2-oxo-1,2-dihydropyridin-3-yl)methyl)-3-isopropoxybenzamide (340 mg, 0.887 mmol, 88% yield) as a white solid. $^1H$ NMR (400 MHz, DMSO-$d_6$) δ=11.49 (s, 1H), 8.41 (t, J=4.9 Hz, 1H), 7.29 (d, J=2.3 Hz, 1H), 6.93 (d, J=2.3 Hz, 1H), 5.87 (s, 1H), 4.76 (dt, J=6.1, 12.1 Hz, 1H), 4.25 (d, J=4.8 Hz, 2H), 2.18 (s, 3H), 2.11 (s, 3H), 1.28 (d, J=6.1 Hz, 6H). MS(ES) $[M+H]^+$ 383.1.

Example 25

5-Chloro-N-[(4,6-dimethyl-2-oxo-1,2-dihydro-3-pyridinyl)methyl]-2-methyl-3-{[1-methyl-2-(methyloxy)ethyl]amino}benzamide

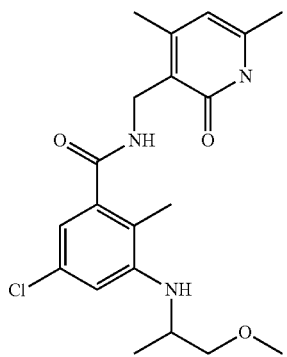 [SMILES: COCC(C)Nc1cc(Cl)cc(C(=O)NCc2c(C)cc(C)[nH]c2=O)c1C]

a) 5-Chloro-2-methyl-3-nitrobenzoic acid

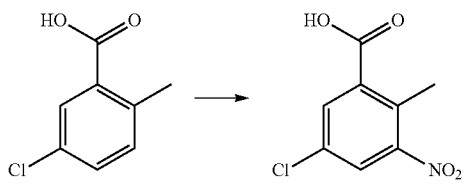

To $H_2SO_4$ (250 ml, 4690 mmol) with stirring at −15° C. (NaCl ice bath) was added portionwise 5-chloro-2-methylbenzoic acid (25 g, 147 mmol) (slowly went into solution). Next a cooled mixture of fuming nitric acid (12.5 ml, 280 mmol) in $H_2SO_4$ (62 mL) was added dropwise. After stirring at −15° C. for 2 hr a cloudy suspension began to form. The reaction was poured onto ice (~500 mL) and stirred for 30 minutes. The suspension was filtered, washed with water, and dried under vacuum to give the product 5-chloro-2-methyl-3-nitrobenzoic acid (30.58 g, 142 mmol, 97% yield) as an off-white solid. 81% pure by LCMS did not show a mass ion. Only ~73% pure by NMR. Used as is in the next reaction. $^1H$ NMR (400 MHz, DMSO-$d_6$) δ=13.89 (br. s., 1H), 8.22 (d, J=2.0 Hz, 1H), 8.03 (d, J=2.0 Hz, 1H), 2.47 (s, 3H).

b) Methyl 5-chloro-2-methyl-3-nitrobenzoate

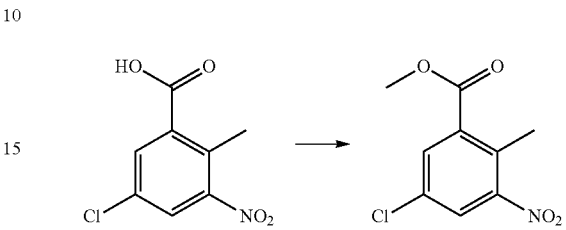

To methanol (150 mL) with stirring at 0° C. was slowly added thionyl chloride (18 ml, 247 mmol) dropwise. After stirring for 15 minutes 5-chloro-2-methyl-3-nitrobenzoic acid (10.0 g, 46.4 mmol) was added. The reaction was allowed to warm to room temperature and stirred for 24 hr. LCMS showed that the reaction was complete. The reaction was evaporated to dryness. The remaining was taken up in a small volume of $CH_2Cl_2$. A white solid crashed out of solution. After trituration the insoluble solid was filtered off and rinsed with a small volume of $CH_2Cl_2$. This white solid corresponded to the impurity from the crude acid starting material. The $CH_2Cl_2$ soluble filtrate was concentrated under vacuum and purified by silica gel chromatography (Analogix, SF40-120 g, 0 to 10% EtOAc in hexanes) to give the product methyl 5-chloro-2-methyl-3-nitrobenzoate (7.37 g, 32.1 mmol, 69.2% yield) as a light yellow oil (solidified to a white solid under vacuum). $^1H$ NMR (400 MHz, DMSO-$d_6$) δ=8.27 (d, J=2.3 Hz, 1H), 8.07 (d, J=2.3 Hz, 1H), 3.89 (s, 3H), 2.45 (s, 3H). MS(ES) $[M+H]^+$ 230.0 (Very weak).

c) Methyl 3-amino-5-chloro-2-methylbenzoate

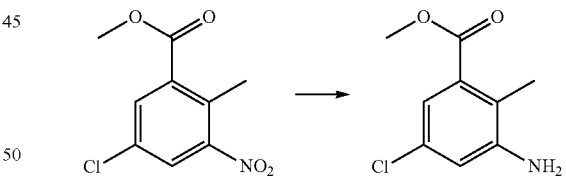

To a stirred solution of methyl 5-chloro-2-methyl-3-nitrobenzoate (5.0 g, 21.78 mmol) in ethyl acetate (150 mL) was added tin(II) chloride dihydrate (20 g, 89 mmol). The mixture was stirred and heated to reflux (85° C. oil bath) for 3 hr (clear solution). LCMS showed that the reaction was complete. The reaction was cooled to room temperature and poured into 1N $Na_2CO_3$ (200 mL). The resultant suspension was stirred for 30 minutes, filtered through a pad of Celite (slow! used a large filter funnel), and rinsed with EtOAc. The filtrate was transferred to a separatory funnel. The EtOAc phase was isolated, washed with water, brine, dried ($Na_2SO_4$), filtered and concentrated under vacuum. Purification by silica gel chromatography (Analogix, SF40-120 g, 0 to 30% EtOAc in hexanes) gave the product methyl 3-amino-5-chloro-2-methylbenzoate (4.05 g, 20.29 mmol, 93% yield) as a yellow oil. $^1$H NMR (400 MHz, DMSO-$d_6$) δ=6.84 (d, J=6.7 Hz, 1H), 6.83 (d, J=6.7 Hz, 1H), 5.47 (s, 2H), 3.79 (s, 3H), 2.13 (s, 3H). MS(ES) [M+H]$^+$ 200.0.

d) Methyl 5-chloro-2-methyl-3-{[1-methyl-2-(methyloxy)ethyl]amino}benzoate

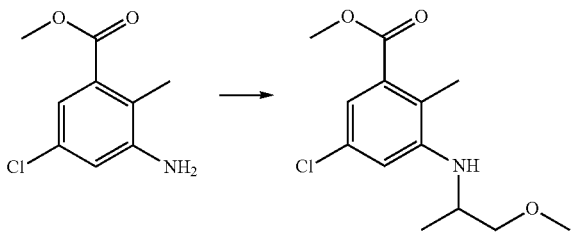 [SMILES: COC(=O)c1cc(Cl)cc(N)c1C ; COCC(C)Nc1cc(Cl)cc(C(=O)OC)c1C]

To a stirred mixture of methyl 3-amino-5-chloro-2-methylbenzoate (750 mg, 3.76 mmol) and 1-methoxypropan-2-one (1.7 mL, 18.47 mmol) in methanol (30 mL) was added zinc chloride (1.5 g, 11.01 mmol). After stirring for 2 hr sodium cyanoborohydride (1.2 g, 19.10 mmol) was added portionwise over 30 minutes (gas evolution). The reaction was heated to 40° C. and stirred overnight. LCMS showed that the reaction was 81% complete. The reaction was evaporated to dryness under vacuum, taken up in EtOAc, washed with sat. NH$_4$Cl, water, brine, dried (Na$_2$SO$_4$), filtered and concentrated under vacuum. Purification by silica gel chromatography (Analogix, SF25-60 g, 0 to 20% EtOAc in hexanes) gave the product methyl 5-chloro-3-((1-methoxypropan-2-yl)amino)-2-methylbenzoate (0.69 g, 2.54 mmol, 67.6% yield) as a clear oil. $^1$H NMR (400 MHz, DMSO-$d_6$) δ=6.85 (d, J=2.0 Hz, 1H), 6.78 (d, J=2.0 Hz, 1H), 4.92 (d, J=8.3 Hz, 1H), 3.80 (s, 3H), 3.78-3.68 (m, 1H), 3.44-3.39 (m, 1H), 3.34-3.29 (m, 1H), 3.28 (s, 3H), 2.15 (s, 3H), 1.16 (d, J=6.6 Hz, 3H). MS(ES) [M+H]$^+$ 272.1.

e) 5-Chloro-2-methyl-3-{[1-methyl-2-(methyloxy)ethyl]amino}benzoic acid

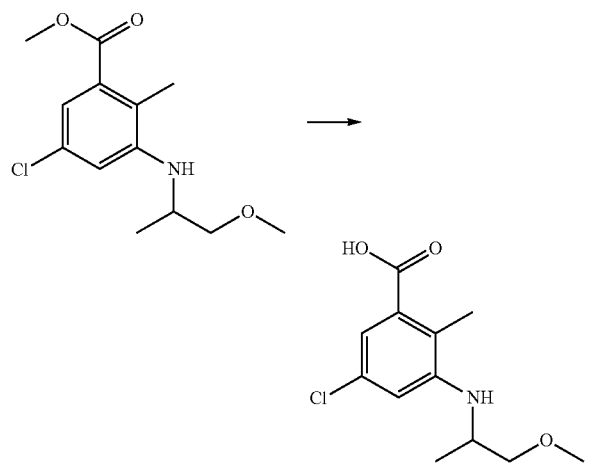

To a stirred solution of methyl 5-chloro-3-((1-methoxypropan-2-yl)amino)-2-methylbenzoate (0.65 g, 2.392 mmol) in methanol (30 mL) was added 1N sodium hydroxide (10 mL, 10.00 mmol). The reaction was heated to 40° C. and stirred for 18 hr. LCMS showed that the reaction was complete. The reaction was concentrated under vacuum to remove the methanol then acidified with 1N HCl (10 mL). The precipitated gummy solid was extracted with CH$_2$Cl$_2$, washed with brine, dried (Na$_2$SO$_4$), filtered, and evaporated to dryness to give the product 5-chloro-3-((1-methoxypropan-2-yl)amino)-2-methylbenzoic acid (0.62 g, 2.406 mmol, 101% yield (existence of residual solvent or small amount of impurities)) as an off-white solid. $^1$H NMR (400 MHz, DMSO-$d_6$) δ=13.02 (br. s., 1H), 6.84 (d, J=2.0 Hz, 1H), 6.74 (d, J=2.0 Hz, 1H), 4.86 (d, J=8.1 Hz, 1H), 3.78-3.66 (m, 1H), 3.45-3.37 (m, 1H), 3.32 (dd, J=5.9, 9.5 Hz, 2H), 2.17 (s, 3H), 1.15 (d, J=6.3 Hz, 3H). MS(ES) [M+H]$^+$ 258.1.

f) 5-Chloro-N-[(4,6-dimethyl-2-oxo-1,2-dihydro-3-pyridinyl)methyl]-2-methyl-3-{[1-methyl-2-(methyloxy)ethyl]amino}benzamide

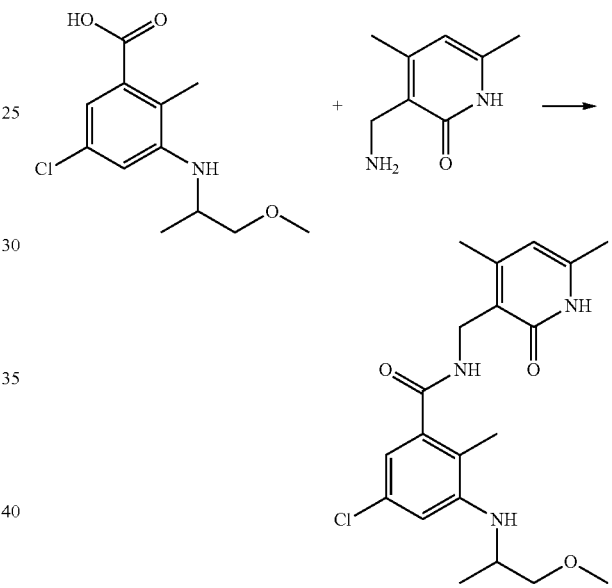

To a stirred mixture of 5-chloro-3-((1-methoxypropan-2-yl)amino)-2-methylbenzoic acid (400 mg, 1.552 mmol), 3-(aminomethyl)-4,6-dimethylpyridin-2(1H)-one hydrochloride salt (300 mg, 1.590 mmol) and HOAt (215 mg, 1.580 mmol) in Dichloromethane (DCM) (20 mL) was added N-methylmorpholine (0.18 mL, 1.637 mmol) followed by EDC free base (290 mg, 1.868 mmol). The reaction was stirred at room temperature overnight for 18 hr. LCMS showed that the reaction was complete. The reaction was concentrated under vacuum and purified by silica gel chromatography (Analogix, SF25-60 g, 0 to 5% MeOH in CH$_2$Cl$_2$). The pure fractions were combined, evaporated to dryness, triturated with hexanes, filtered, washed with hexanes and dried under vacuum to give the product 5-chloro-N-((4,6-dimethyl-2-oxo-1,2-dihydropyridin-3-yl)methyl)-3-((1-methoxypropan-2-yl)amino)-2-methylbenzamide (561 mg, 1.432 mmol, 92% yield) as a white solid. $^1$H NMR (400 MHz, DMSO-$d_6$) δ=11.47 (s, 1H), 8.11 (t, J=4.9 Hz, 1H), 6.61 (d, J=2.0 Hz, 1H), 6.43 (d, J=2.0 Hz, 1H), 5.86 (s, 1H), 4.72 (d, J=8.3 Hz, 1H), 4.23 (d, J=5.1 Hz, 2H), 3.74-3.64 (m, 1H), 3.42-3.37 (m, 1H), 3.33 (s, 3H), 3.32-3.29 (m, 1H), 2.18 (s, 3H), 2.11 (s, 3H), 1.96 (s, 3H), 1.14 (d, J=6.3 Hz, 3H). MS(ES) [M+H]$^+$ 392.2.

Example 26

5-Chloro-N-[(4,6-dimethyl-2-oxo-1,2-dihydro-3-pyridinyl)methyl]-3-[(2-hydroxy-1-methylethyl)amino]-2-methylbenzamide

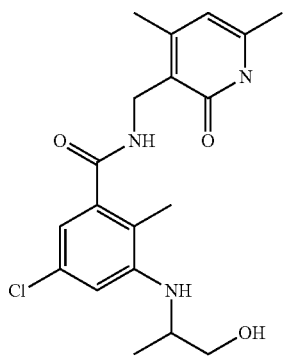 [SMILES: Cc1cc(C)c(CNC(=O)c2cc(Cl)cc(NC(C)CO)c2C)c(=O)[nH]1]

To a stirred suspension of 5-chloro-N-((4,6-dimethyl-2-oxo-1,2-dihydropyridin-3-yl)methyl)-3-((1-methoxypropan-2-yl)amino)-2-methylbenzamide (250 mg, 0.638 mmol) in acetonitrile (10 mL) was added TMSI (500 μl, 3.67 mmol) dropwise (the reaction quickly cleared up). The reaction was heated to 70° C. (a condenser was attached). After 1 hr LCMS showed that the reaction was only 39% complete. An additional 200 uL of TMSI was added and the reaction stirred at 70° C. for another 1 hr. LCMS now showed that the reaction was 55% complete. One more 200 uL of TMSI was added and the reaction stirred for an additional 2 hr at 70° C. Total time was 4 hr. A total of 900 uL TMSI (~10 equiv.) was used. LCMS showed that the reaction was ~80% complete. The reaction was cooled to room temperature and treated with methanol (10 mL) and stirred for 10 minutes then treated with aq. $Na_2S_2O_4$ (10 mL) and stirred for 20 minutes. (The color eventually disappeared.) The organics were removed by evaporation under vacuum. The insoluble material was removed by filtration, washed with a small volume of water then dried under vacuum to give the crude product. Purified by silica gel chromatography (Analogix, SF25-60 g, 0 to 10% MeOH in $CH_2Cl_2$) (A DASi column with just a filter was used since the starting material was not soluble in $CH_2Cl_2$.) The pure fractions were combined, evaporated to dryness, triturated with water, filtered and dried under vacuum to give the product 5-chloro-N-((4,6-dimethyl-2-oxo-1,2-dihydropyridin-3-yl)methyl)-3-((1-hydroxypropan-2-yl)amino)-2-methylbenzamide (99 mg, 0.262 mmol, 41.1% yield) as a white solid. $^1$H NMR (400 MHz, DMSO-$d_6$) δ=11.47 (s, 1H), 8.11 (t, J=4.9 Hz, 1H), 6.59 (d, J=2.0 Hz, 1H), 6.42 (d, J=2.0 Hz, 1H), 5.86 (s, 1H), 4.78 (br. s., 1H), 4.68 (d, J=7.3 Hz, 1H), 4.23 (d, J=5.1 Hz, 2H), 3.52-3.41 (m, 2H), 3.39-3.30 (m, 1H), 2.18 (s, 3H), 2.11 (s, 3H), 1.97 (s, 3H), 1.13 (d, J=6.3 Hz, 3H). MS(ES) [M+H]$^+$ 378.1.

Example 27

5-Chloro-N-[(4,6-dimethyl-2-oxo-1,2-dihydro-3-pyridinyl)methyl]-2-methyl-3-[(1-methylethyl)oxy]benzamide

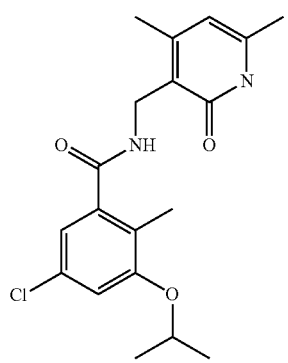

a) Methyl 5-chloro-3-hydroxy-2-methylbenzoate

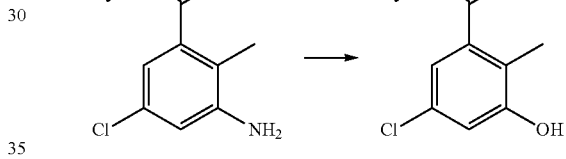

To a vigorously stirred solution of methyl 5-chloro-3-hydroxy-2-methylbenzoate (1.28 g, 6.38 mmol, 70.8% yield) in methanol (5 mL) was added dropwise 10% $H_2SO_4$ (20 ml, 37.5 mmol). (The solution quickly formed a suspension.) The stirred mixture was cooled to 0° C. in an ice bath then a solution of sodium nitrite (0.80 g, 11.59 mmol) in water (6 mL) was added dropwise slowly over 15 minutes. The suspension was stirred at 0° C. for 1 hr. Clumps were occasionally broken up with the aid of a spatula. After 1 hr a small volume of methanol (~5 mL) was used to rinse down the sides of the flask. The reaction was allowed to warm to room temperature then treated with a solution of 50% $H_2SO_4$ (20 ml, 188 mmol). The reaction was heated to 100° C. and stirred for 1 hr. (A blast shield was used for safety.) The resulting suspension was poured into ice water (~300 mL), the solids filtered off, washed with water, then dried under vacuum to give the crude phenol. LCMS showed 22% hydrolyzed methyl ester and 76% product.

A stirred solution of MeOH (100 mL) at 0° C. in an ice bath was slowly treated with thionyl chloride (5.0 ml, 68.5 mmol). After stirring for 15 minutes the solution was added to the above. The reaction was stirred overnight at room temperature. LCMS showed that all of the mixture was converted to the methyl ester. The reaction was evaporated to dryness then purified by silica gel chromatography (Analogix, SF25-60 g, 0 to 20% EtOAc in hexanes). The pure fractions were combined and evaporated to dryness to give the product methyl 5-chloro-3-hydroxy-2-methylbenzoate (1.28 g, 6.38 mmol, 70.8% yield) as a pale yellow solid. $^1$H NMR (400 MHz, DMSO-$d_6$) δ=10.30 (br. s., 1H), 7.18 (d, J=2.3 Hz, 1H), 7.01 (d, J=2.0 Hz, 1H), 3.82 (s, 3H), 2.25 (s, 3H). MS(ES) [M+H]⁺201.0.

b) Methyl 5-chloro-2-methyl-3-[(1-methylethyl)oxy]benzoate

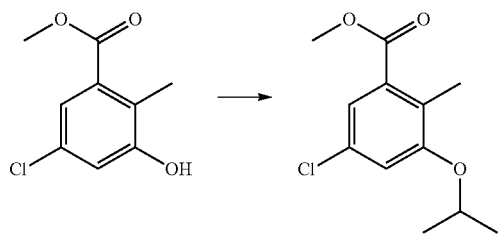 [SMILES: COC(=O)c1cc(Cl)cc(O)c1C ; COC(=O)c1cc(Cl)cc(OC(C)C)c1C]

To a stirred mixture of methyl 5-chloro-3-hydroxy-2-methylbenzoate (0.6 g, 2.99 mmol) and cesium carbonate (1.2 g, 3.68 mmol) in N,N-Dimethylformamide (DMF) (10 mL) was added 2-iodopropane (0.45 mL, 4.50 mmol). The reaction was stirred overnight at room temperature. LCMS showed that the reaction was complete. The reaction was evaporated to dryness, taken up in EtOAc, washed with water, brine, dried (MgSO$_4$), filtered and concentrated under vacuum. Purified by silica gel chromatography (Analogix, SF25-60 g, 0 to 10% EtOAc in hexanes) to give the product methyl 5-chloro-3-isopropoxy-2-methylbenzoate (0.62 g, 2.55 mmol, 85% yield) as a clear oil. $^1$H NMR (400 MHz, DMSO-d$_6$) δ=7.29 (d, J=2.0 Hz, 1H), 7.28 (d, J=2.2 Hz, 1H), 4.70 (dt, J=6.1, 12.1 Hz, 1H), 3.83 (s, 3H), 2.25 (s, 3H), 1.28 (d, J=6.1 Hz, 6H). MS(ES) [M+H]⁺ 243.1.

c) 5-Chloro-2-methyl-3-[(1-methylethyl)oxy]benzoic acid

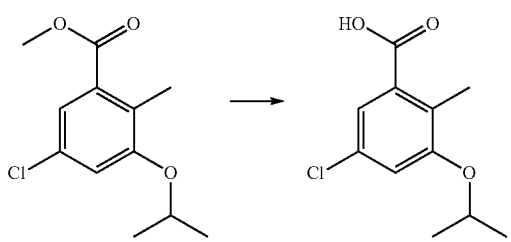 [SMILES: COC(=O)c1cc(Cl)cc(OC(C)C)c1C ; Cc1c(OC(C)C)cc(Cl)cc1C(=O)O]

To a stirred solution of methyl 5-chloro-3-isopropoxy-2-methylbenzoate (0.60 g, 2.472 mmol) in methanol (20 mL) was added 1N sodium hydroxide (10 mL, 10.00 mmol). The reaction was heated to 40° C. and stirred for 18 hr. LCMS showed that the reaction was complete. The reaction was evaporated under vacuum to remove the methanol then acidified with 1N HCl (10 mL). The precipitated solids were filtered off, washed with water and dried under vacuum to give the product 5-chloro-3-isopropoxy-2-methylbenzoic acid (0.53 g, 2.318 mmol, 94% yield) as a white solid. This material was 93% pure by LCMS and had 7% starting ester. Used as is in the next reaction. $^1$H NMR (400 MHz, DMSO-d$_6$) δ=13.20 (br. s., 1H), 7.27 (d, J=2.0 Hz, 1H), 7.23 (d, J=2.3 Hz, 1H), 4.68 (dt, J=6.0, 11.9 Hz, 1H), 2.27 (s, 3H), 1.28 (d, J=5.8 Hz, 6H). MS(ES) [M+H]⁺229.1.

d) 5-Chloro-N-[(4,6-dimethyl-2-oxo-1,2-dihydro-3-pyridinyl)methyl]-2-methyl-3-[(1-methylethyl)oxy]benzamide

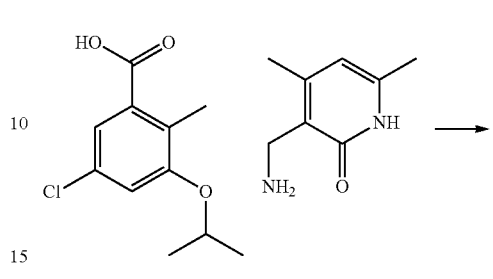

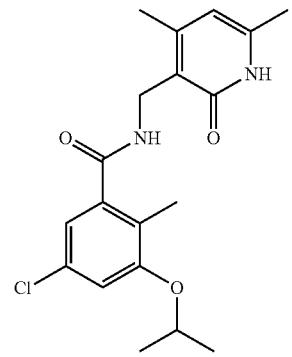

To a stirred mixture of 5-chloro-3-isopropoxy-2-methylbenzoic acid (250 mg, 1.093 mmol), 3-(aminomethyl)-4,6-dimethylpyridin-2(1H)-one hydrochloride salt (230 mg, 1.219 mmol) and HOAt (150 mg, 1.102 mmol) in Dichloromethane (DCM) (20 mL) was added N-methylmorpholine (140 L, 1.273 mmol) followed by EDC free base (210 mg, 1.353 mmol). The reaction was stirred at room temperature overnight for 18 hr. LCMS showed that the reaction was complete. The reaction was concentrated under vacuum and purified by silica gel chromatography (Analogix, SF25-60 g, 0 to 5% MeOH in CH$_2$Cl$_2$) (Not real soluble in CH$_2$Cl$_2$. Used a DASi filter). The pure fractions were combined, evaporated to dryness, triturated with 5% MeOH in water, filtered, washed with water and dried under vacuum to give the product 5-chloro-N-((4,6-dimethyl-2-oxo-1,2-dihydropyridin-3-yl)methyl)-3-isopropoxy-2-methylbenzamide (338 mg, 0.932 mmol, 85% yield) as a white solid.

$^1$H NMR (400 MHz, DMSO-d$_6$) δ=11.48 (s, 1H), 8.24 (t, J=4.9 Hz, 1H), 7.07 (d, J=2.0 Hz, 1H), 6.80 (d, J=2.0 Hz, 1H), 5.86 (s, 1H), 4.65 (dt, J=6.0, 12.1 Hz, 1H), 4.24 (d, J=5.1 Hz, 2H), 2.18 (s, 3H), 2.11 (s, 3H), 2.04 (s, 3H), 1.26 (d, J=5.8 Hz, 6H). MS(ES) [M+H]⁺ 363.1.

Example 28

5-Chloro-3-(cyclopentyloxy)-N-[(4,6-dimethyl-2-oxo-1,2-dihydro-3-pyridinyl)methyl]-2-methylbenzamide

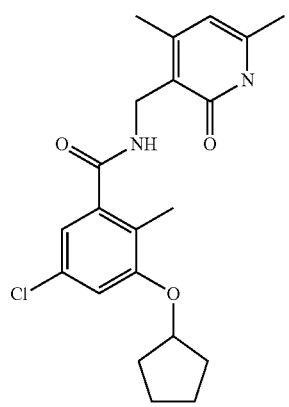 [SMILES: Cc1cc(C)c(CNC(=O)c2cc(Cl)cc(OC3CCCC3)c2C)c(=O)[nH]1]

a) Methyl 5-chloro-3-(cyclopentyloxy)-2-methylbenzoate

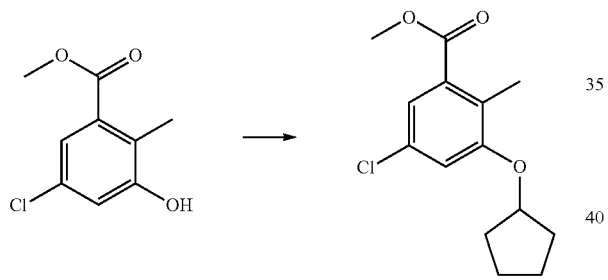

To a stirred mixture of methyl 5-chloro-3-hydroxy-2-methylbenzoate (0.6 g, 2.99 mmol) and cesium carbonate (1.2 g, 3.68 mmol) in N,N-Dimethylformamide (DMF) (10 mL) was added iodocyclopentane (0.55 mL, 4.76 mmol). The reaction was stirred overnight at room temperature. LCMS showed that the reaction was 62% complete. The reaction was heated at 60° C. and stirred overnight. LCMS showed that the reaction was complete. The reaction was evaporated to dryness, taken up in EtOAc, washed with water, brine, dried (MgSO$_4$), filtered and concentrated under vacuum, Purified by silica gel chromatography (Analogix, SF25-60 g, 0 to 10% EtOAc in hexanes) to give the product methyl 5-chloro-3-(cyclopentyloxy)-2-methylbenzoate (0.81 g, 3.01 mmol, 101% yield (existence of residual solvent or small amount of impurities)) as a clear oil. $^1$H NMR (400 MHz, DMSO-d$_6$) δ=7.28 (d, J=2.0 Hz, 1H), 7.22 (d, J=2.0 Hz, 1H), 4.94 (t, J=5.4 Hz, 1H), 3.82 (s, 3H), 2.24 (s, 3H), 1.96-1.85 (m, 2H), 1.76-1.66 (m, 4H), 1.65-1.57 (m, 2H). MS(ES) [M+H]$^+$ 269.1.

b) 5-Chloro-3-(cyclopentyloxy)-2-methylbenzoic acid

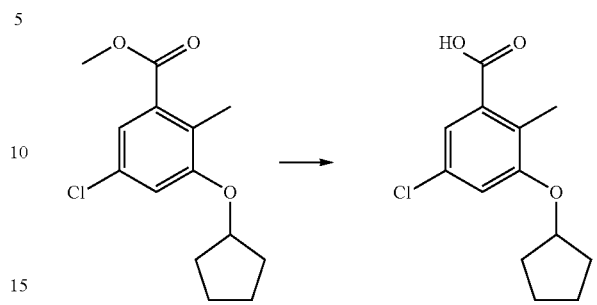

To a stirred solution of methyl 5-chloro-3-(cyclopentyloxy)-2-methylbenzoate (0.80 g, 2.98 mmol) in methanol (40 mL) was added 1N sodium hydroxide (10 ml, 10.00 mmol). The reaction was heated to 40° C. and stirred for 18 hr. LCMS showed that the reaction was complete. The reaction was evaporated under vacuum to remove the methanol then acidified with 1N HCl (10 mL). The precipitated solids were filtered off, washed with water and dried under vacuum to give the product 5-chloro-3-(cyclopentyloxy)-2-methylbenzoic acid (0.74 g, 2.91 mmol, 98% yield) as a white solid. $^1$H NMR (400 MHz, DMSO-d$_6$) δ=13.24 (br. s., 1H), 7.26 (d, J=2.3 Hz, 1H), 7.17 (d, J=2.0 Hz, 1H), 4.92 (t, J=5.6 Hz, 1H), 2.25 (s, 3H), 1.96-1.84 (m, 2H), 1.77-1.65 (m, 4H), 1.65-1.54 (m, 2H). MS(ES) [M+H]$^+$ 255.1.

c) 5-Chloro-3-(cyclopentyloxy)-N-[(4,6-dimethyl-2-oxo-1,2-dihydro-3-pyridinyl)methyl]-2-methylbenzamide

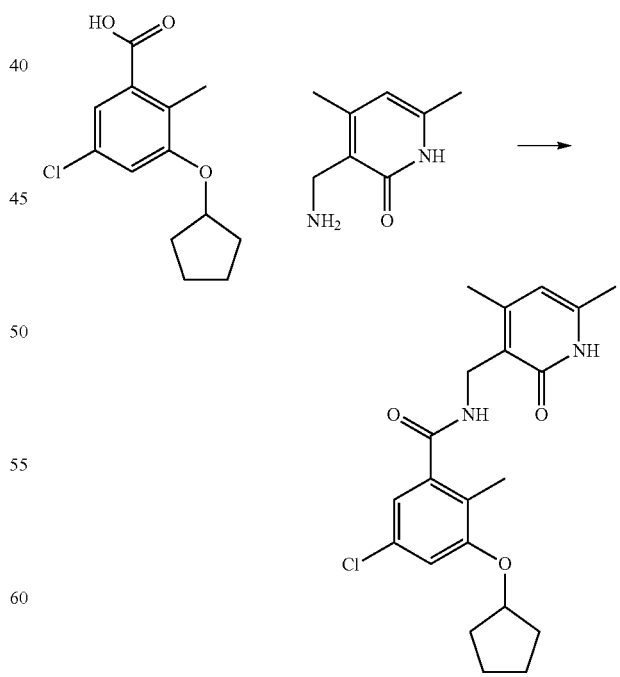

To a stirred mixture of 5-chloro-3-(cyclopentyloxy)-2-methylbenzoic acid (250 mg, 0.982 mmol), 3-(aminomethyl)-4,6-dimethylpyridin-2(1H)-one hydrochloride salt (200 mg, 1.060 mmol) and HOAt (140 mg, 1.029 mmol) in Dichloromethane (DCM) (20 mL) was added N-methylmorpholine (120 μL, 1.091 mmol) followed by EDC free base (190 mg, 1.224 mmol). The reaction was stirred at room temperature overnight for 18 hr. LCMS showed that the reaction was complete. The reaction was concentrated under vacuum and purified by silica gel chromatography (Analogix, SF25-60 g, 0 to 4% MeOH in CH$_2$Cl$_2$) (Not real soluble in CH$_2$Cl$_2$. Used a DASi filter). The pure fractions were combined, evaporated to dryness, triturated with 5% MeOH in water, filtered, washed with water and dried under vacuum to give the product 5-chloro-3-(cyclopentyloxy)-N-((4,6-dimethyl-2-oxo-1,2-dihydropyridin-3-yl)methyl)-2-methylbenzamide (332 mg, 0.854 mmol, 87% yield) as a white solid. $^1$H NMR (400 MHz, DMSO-d$_6$) δ=11.48 (br. s., 1H), 8.23 (t, J=4.9 Hz, 1H), 7.02 (d, J=1.8 Hz, 1H), 6.80 (d, J=2.0 Hz, 1H), 5.86 (s, 1H), 4.89 (t, J=5.4 Hz, 1H), 4.24 (d, J=5.1 Hz, 2H), 2.18 (s, 3H), 2.11 (s, 3H), 2.02 (s, 3H), 1.93-1.83 (m, 2H), 1.76-1.64 (m, 4H), 1.63-1.55 (m, 2H). MS(ES) [M+H]$^+$389.1.

Example 29

2,5-Dichloro-N-[(4,6-dimethyl-2-oxo-1,2-dihydro-3-pyridinyl)methyl]-3-(1-methyl-1H-pyrazol-5-yl)benzamide

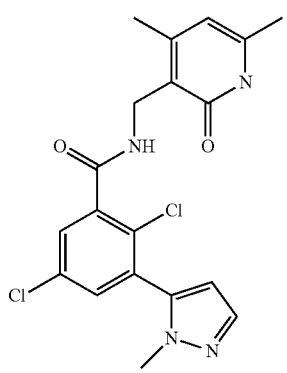 [SMILES: Cc1cc(C)c(CNC(=O)c2cc(Cl)cc(-c3ccnn3C)c2Cl)c(=O)[nH]1]

a) Methyl 2,5-dichloro-3-iodobenzoate

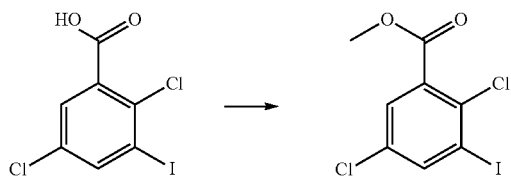

To methanol (100 mL) at 0° C. with stirring was added dropwise thionyl chloride (5.0 ml, 68.5 mmol). After 15 minutes 2,5-dichloro-3-iodobenzoic acid (5.0 g, 15.78 mmol) was added. The reaction was stirred overnight at room temperature then refluxed at 70° C. for 4 hr. LCMS showed that the reaction was complete. The reaction was evaporated to dryness under vacuum then purified by silica gel chromatography (Analogix, SF40-115 g, 0 to 15% EtOAc in hexanes). The pure fractions were combined and evaporated to dryness to give the product methyl 2,5-dichloro-3-iodobenzoate (4.17 g, 12.60 mmol, 80% yield) as a yellow oil (solidified under vacuum). $^1$H NMR (400 MHz, DMSO-d$_6$) δ=8.27 (d, J=2.5 Hz, 1H), 7.85 (d, J=2.5 Hz, 1H), 3.87 (s, 3H). MS(ES) [M+H]$^+$ 330.7 (weak).

b) Methyl 2,5-dichloro-3-(1-methyl-1H-pyrazol-5-yl)benzoate

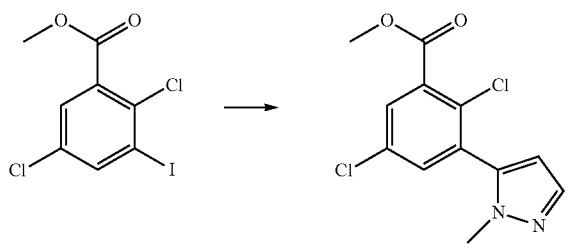 [SMILES: COC(=O)c1cc(Cl)cc(I)c1Cl ; COC(=O)c1cc(Cl)cc(-c2ccnn2C)c1Cl]

In a 20 mL microwave vial was added methyl 2,5-dichloro-3-iodobenzoate (500 mg, 1.511 mmol), 1-methyl-5-(4,4,5,5-tetramethyl-1,3,2-dioxaborolan-2-yl)-1H-pyrazole (500 mg, 2.403 mmol), sodium bicarbonate (381 mg, 4.53 mmol), N,N-Dimethylformamide (DMF) (20 mL) and water (2 mL). The mixture was stirred and purged with N$_2$. To the reaction was added PdCl$_2$(PPh$_3$)$_2$ (60 mg, 0.085 mmol). The vial was capped and stirred at 90° C. for 2 hr. The reaction turned black after ~1.5 hrs. LCMS showed after 2 hr the reaction was complete. The reaction was evaporated to dryness under vacuum and purified by silica gel chromatography (Analogix, SF25-60 g, 0 to 30% EtOAc in hexanes) (loaded with CH$_2$Cl$_2$ onto a DASi column). The pure fractions were combined and evaporated to dryness to give the product methyl 2,5-dichloro-3-(1-methyl-1H-pyrazol-5-yl)benzoate (0.36 g, 1.263 mmol, 84% yield) as a clear oil. $^1$H NMR (400 MHz, DMSO-d$_6$) δ=7.98 (d, J=2.8 Hz, 1H), 7.81 (d, J=2.5 Hz, 1H), 7.54 (d, J=1.8 Hz, 1H), 6.42 (d, J=1.8 Hz, 1H), 3.90 (s, 3H), 3.66 (s, 3H). MS(ES) [M+H]$^+$ 285.0.

c) 2,5-Dichloro-3-(1-methyl-1H-pyrazol-5-yl)benzoic acid

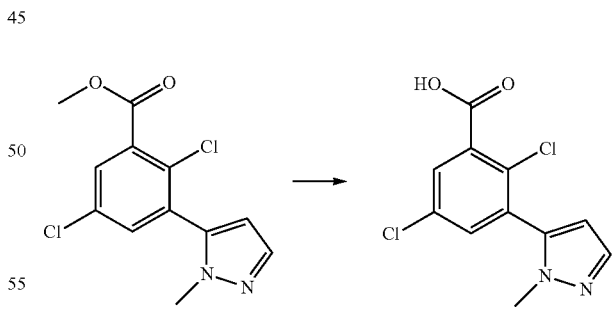

To a stirred solution of methyl 2,5-dichloro-3-(1-methyl-1H-pyrazol-5-yl)benzoate (0.35 g, 1.228 mmol) in Methanol (25 mL) was added 1N sodium hydroxide (5.0 ml, 5.00 mmol). The reaction was heated to 40° C. and stirred overnight. LCMS showed that the reaction was complete. The reaction was evaporated under vacuum to remove the methanol then acidified with 1N HCl (5.0 mL). The solid which separated was filtered off washed with water and dried under vacuum to give the product 2,5-dichloro-3-(1-methyl-1H-pyrazol-5-yl)benzoic acid (299 mg, 1.103 mmol, 90% yield) as an off-white solid. ¹H NMR (400 MHz, DMSO-d₆) δ=13.94 (br. s., 1H), 7.92 (d, J=2.5 Hz, 1H), 7.74 (d, J=2.8 Hz, 1H), 7.53 (d, J=2.0 Hz, 1H), 6.41 (d, J=2.0 Hz, 1H), 3.65 (s, 3H). MS(ES) [M+H]⁺ 271.0.

d) 2,5-Dichloro-N-[(4,6-dimethyl-2-oxo-1,2-dihydro-3-pyridinyl)methyl]-3-(1-methyl-1H-pyrazol-5-yl)benzamide

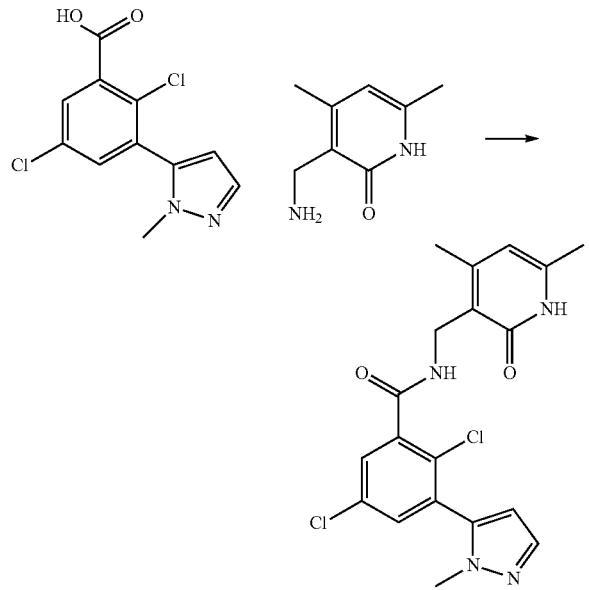

To a stirred mixture of 2,5-dichloro-3-(1-methyl-1H-pyrazol-5-yl)benzoic acid (250 mg, 0.922 mmol), 3-(aminomethyl)-4,6-dimethylpyridin-2(1H)-one hydrochloride salt (190 mg, 1.007 mmol) and HOAt (130 mg, 0.955 mmol) in Dichloromethane (DCM) (20 mL) was added N-methylmorpholine (110 µL, 1.001 mmol) followed by EDC free base (180 mg, 1.159 mmol). The reaction was stirred at room temperature overnight for 18 hr. Reaction formed a thick suspension. LCMS showed that the reaction was complete. Tried to purify by silica gel chromatography (Analogix, SF25-60 g, 0 to 10% MeOH in CH₂Cl₂) (Not real soluble in CH₂Cl₂. Used a DASi filter). Most of the product remained on the DASi filter. This insoluble material was removed as well as product which streaked off the column, triturated with 10% MeOH in water, filtered, washed with the same and dried under vacuum to give the product 2,5-dichloro-N-((4,6-dimethyl-2-oxo-1,2-dihydropyridin-3-yl)methyl)-3-(1-methyl-1H-pyrazol-5-yl)benzamide (342 mg, 0.844 mmol, 92% yield) as a white solid. The sample for the LCMS was suspended in MeOH with 1 drop of 6N HCl to dissolve. ¹H NMR (400 MHz, DMSO-d₆) δ=11.51 (br. s., 1H), 8.57 (t, J=4.8 Hz, 1H), 7.60 (d, J=2.5 Hz, 1H), 7.55 (d, J=2.5 Hz, 1H), 7.52 (d, J=1.8 Hz, 1H), 6.36 (d, J=1.8 Hz, 1H), 5.88 (s, 1H), 4.29 (d, J=4.8 Hz, 2H), 3.64 (s, 3H), 2.20 (s, 3H), 2.11 (s, 3H). MS(ES) [M+H]⁺ 405.1.

Examples 30-41 were prepared by the methods either described above or in the intermediates section, or routine variations thereof:

| Ex | Structure | Name | 1H NMR | MS(ES) [M + H]⁺ |
|---|---|---|---|---|
| 30 | 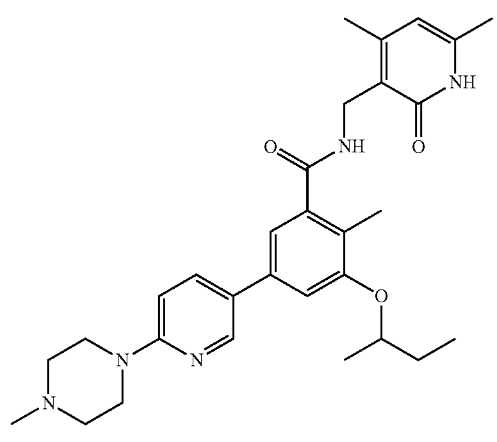 | 3-(sec-butoxy)-N-((4,6-dimethyl-2-oxo-1,2-dihydropyridin-3-yl)methyl)-2-methyl-5-(6-(4-methylpiperazin-1-yl)pyridin-3-yl)benzamide | 0.94 (t, J = 7.33 Hz, 3 H) 1.25 (d, J = 5.81 Hz, 3 H) 1.58-1.73 (m, 2 H) 2.11 (d, J = 3.28 Hz, 6 H) 2.20 (s, 3 H) 2.22 (s, 3 H) 2.37-2.44 (m, 4 H) 3.48-3.56 (m, 4 H) 4.27 (s, 1 H) 4.28 (s, 1 H) 4.51-4.60 (m, 1 H) 5.86 (s, 1 H) 6.90 (d, J = 8.84 Hz, 1 H) 7.00 (d, J = 1.52 Hz, 1 H) 7.14-7.18 (m, 1 H) 7.84 (dd, J = 8.84, 2.53 Hz, 1 H) 8.19 (br. s., 1 H) 8.43 (d, J = 2.27 Hz, 1 H) 11.38 (br. s., 1 H) | 518.4 |

-continued

| Ex | Structure | Name | 1H NMR | MS(ES) [M + H]+ |
|---|---|---|---|---|
| 31 | 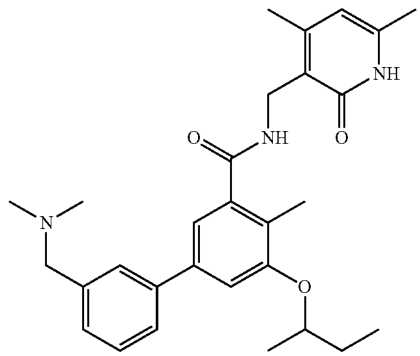 | 5-(sec-butoxy)-N-((4,6-dimethyl-2-oxo-1,2-dihydropyridin-3-yl)methyl)-3'-((dimethylamino)methyl)-4-methyl-[1,1'-biphenyl]-3-carboxamide | 0.95 (t, J = 7.45 Hz, 3 H) 1.26 (d, J = 6.06 Hz, 3 H) 1.62-1.72 (m, 2 H) 2.11 (s, 3 H) 2.13 (s, 3 H) 2.16 (s, 6 H) 2.20 (s, 3 H) 3.45 (s, 2 H) 4.28 (s, 1 H) 4.29 (s, 1 H) 4.56 (q, J = 5.98 Hz, 1 H) 5.86 (s, 1 H) 7.04 (d, J = 1.52 Hz, 1 H) 7.18 (d, J = 1.52 Hz, 1 H) 7.27 (d, J = 7.58 Hz, 1 H) 7.40 (t, J = 7.96 Hz, 1 H) 7.52-7.55 (m, 2 H) 8.25 (br. s., 1 H) 11.39 (br. s., 1 H) | 476.3 |
| 32 | 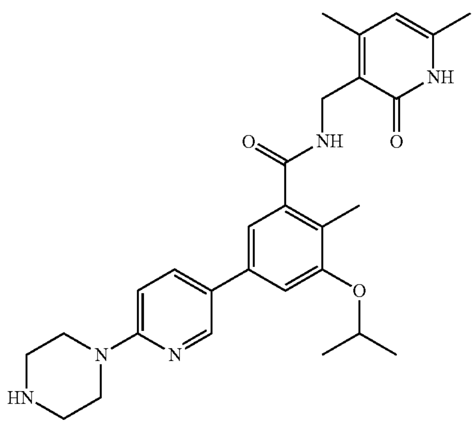 [SMILES: Cc1cc(C)c(CNC(=O)c2cc(-c3ccc(N4CCNCC4)nc3)cc(OC(C)C)c2C)c(=O)[nH]1] | N-((4,6-dimethyl-2-oxo-1,2-dihydropyridin-3-yl)methyl)-3-isopropoxy-2-methyl-5-(6-(piperazin-1-yl)pyridin-3-yl)benzamide | 11.48 (br. s., 1 H), 8.42 (d, J = 2.5 Hz, 1 H), 8.16 (t, J = 4.9 Hz, 1 H), 7.83 (dd, J = 9.0, 2.7 Hz, 1 H), 7.17 (d, J = 1.5 Hz, 1 H), 7.01 (d, J = 1.8 Hz, 1 H), 6.85 (d, J = 8.8 Hz, 1 H), 5.86 (s, 1 H), 4.73 (quin, J = 6.1 Hz, 1 H), 4.27 (d, J = 5.1 Hz, 2 H), 3.44 (m, 4 H), 2.78 (m, 4 H), 2.20 (s, 3 H), 2.09 (m, 6 H), 1.28 (m, 6 H) | 490.4 |
| 33 | 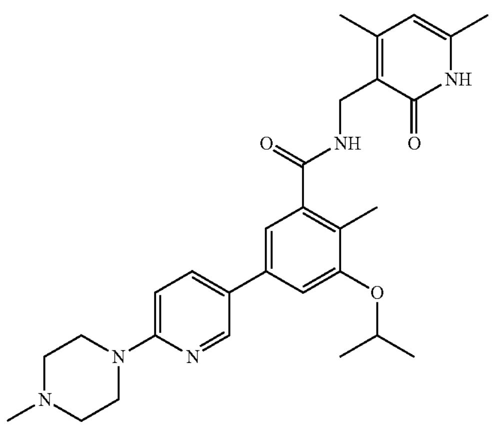 | N-((4,6-dimethyl-2-oxo-1,2-dihydropyridin-3-yl)methyl)-3-isopropoxy-2-methyl-5-(6-(4-methylpiperazin-1-yl)pyridin-3-yl)benzamide | 11.47 (s, 1 H), 8.43 (d. J = 2.3 Hz, 1 H), 8.16 (t, J = 4.9 Hz, 1 H), 7.84 (dd, J = 8.8, 2.5 Hz, 1 H), 7.17 (m, 1 H), 7.01 (d, J = 1.5 Hz, 1 H), 6.89 (d, J = 8.8 Hz, 1 H), 5.86 (s, 1 H), 4.73 (quin, J = 6.0 Hz, 1 H), 4.28 (d, J = 5.1 Hz, 2 H), 3.51 (m, 4 H), 2.40 (m, 4 H), 2.21 (d, J = 8.6 Hz, 6 H), 2.09 (m, 6 H), 1.29 (m, 6 H) | 504.7 |
| 34 | 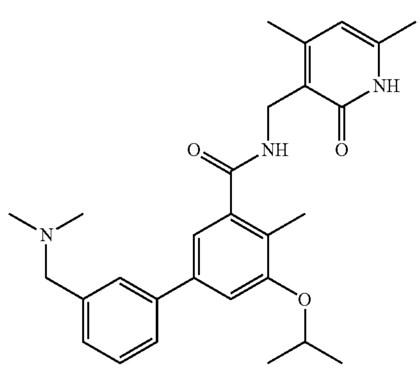 | N-((4,6-dimethyl-2-oxo-1,2-dihydropyridin-3-yl)methyl)-3'-((dimethylamino)methyl)-5-isopropoxy-4-methyl-[1,1'-biphenyl]-3-carboxamide | 11.46 (s, 1 H), 8.21 (t, J = 4.9 Hz, 1 H), 7.53 (m, 2 H), 7.39 (t, J = 7.6 Hz, 1 H), 7.27 (d, J = 7.6 Hz, 1 H), 7.20 (m, 1 H), 7.05 (d, J = 1.5 Hz, 1 H), 5.86 (s, 1 H), 4.74 (m, 1 H), 4.28 (d, J = 4.8 Hz, 2 H), 3.44 (s, 2 H), 2.20 (s, 3 H), 2.16 (s, 6 H), 2.13 (s, 3 H), 2.10 (s, 3 H), 1.30 (m, 6 H) | 462.4 |

-continued

| Ex | Structure | Name | 1H NMR | MS(ES) [M + H]+ |
|---|---|---|---|---|
| 35 | 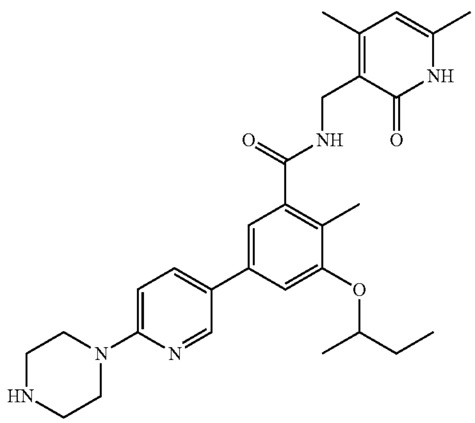 [SMILES: CCC(C)Oc1cc(-c2ccc(N3CCNCC3)nc2)cc(C(=O)NCc2c(C)cc(C)[nH]c2=O)c1C] | 3-(sec-butoxy)-N-((4,6-dimethyl-2-oxo-1,2-dihydropyridin-3-yl)methyl)-2-methyl-5-(6-(piperazin-1-yl)pyridin-3-yl)benzamide | 0.94 (t, J = 7.33 Hz, 3 H) 1.25 (d, J = 5.81 Hz, 3 H) 1.58-1.72 (m, 2 H) 2.11 (d, J = 2.27 Hz, 6 H) 2.20 (s, 3 H) 2.71-2.85 (m, 3 H) 3.40-3.55 (m, 4 H) 4.27 (s, 1 H) 4.29 (s, 1 H) 4.52-4.59 (m, 1 H) 5.86 (s, 1 H) 6.86 (d, J = 9.09 Hz, 1 H) 7.00 (d, J = 1.26 Hz, 1 H) 7.13-7.17 (m, 1 H) 7.83 (dd, J = 8.84, 2.53 Hz, 1 H) 8.17 (t, J = 4.93 Hz, 1 H) 8.43 (d, J = 2.53 Hz, 1 H) 11.49 (br. s., 1 H) | 504.4 |
| 36 | 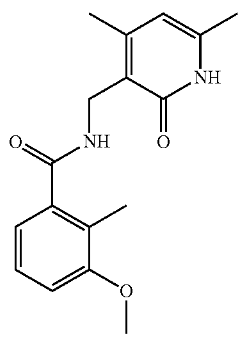 [SMILES: COc1cccc(C(=O)NCc2c(C)cc(C)[nH]c2=O)c1C] | N-((4,6-dimethyl-2-oxo-1,2-dihydropyridin-3-yl)methyl)-3-methoxy-2-methylbenzamide | 2.10 (d, J = 4.80 Hz, 6 H) 2.19 (s, 3 H) 3.78 (s, 3 H) 4.26 (d, J = 5.05 Hz, 2 H) 5.86 (s, 1 H) 6.81 (d, J = 6.82 Hz, 1 H) 6.97 (d, J = 7.83 Hz, 1 H) 7.16 (t, J = 7.96 Hz, 1 H) 8.05 (t, J = 4.93 Hz, 1 H) 11.46 (s, 1 H) | 301.2 |
| 37 | 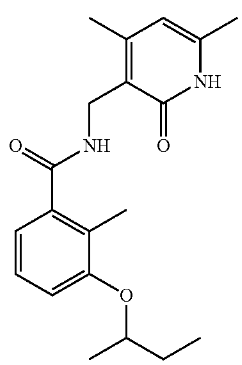 [SMILES: CCC(C)Oc1cccc(C(=O)NCc2c(C)cc(C)[nH]c2=O)c1C] | 3-(sec-butoxy)-N-((4,6-dimethyl-2-oxo-1,2-dihydropyridin-3-yl)methyl)-2-methylbenzamide | 0.93 (t, J = 7.33 Hz, 3 H) 1.22 (d, J = 6.06 Hz, 3 H) 1.63 (ddd, J = 11.56, 7.39, 6.06 Hz, 2 H) 2.09 (s, 3 H) 2.11 (s, 3 H) 2.19 (s, 3 H) 4.25 (s, 1 H) 4.26 (s, 1 H) 4.34-4.40 (m, 1 H) 5.86 (s, 1 H) 6.77 (d, J = 7.33 Hz, 1 H) 6.96 (d, J = 8.08 Hz, 1 H) 7.11 (t, J = 7.83 Hz, 1 H) 8.04 (t, J = 4.93 Hz, 1 H) 11.46 (br. s., 1 H) | 343.2 |
| 38 | 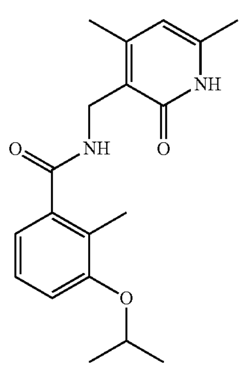 [SMILES: Cc1cc(C)c(CNC(=O)c2cccc(OC(C)C)c2C)c(=O)[nH]1] | N-((4,6-dimethyl-2-oxo-1,2-dihydropyridin-3-yl)methyl)-3-isopropoxy-2-methylbenzamide | 1.25 (s, 3 H) 1.27 (s, 3 H) 2.08 (s, 3 H) 2.11 (s, 3 H) 2.19 (s, 3 H) 4.25 (s, 1 H) 4.26 (s, 1 H) 4.57 (dt, J = 12.06, 5.97 Hz, 1 H) 5.86 (s, 1 H) 6.78 (d, J = 6.82 Hz, 1 H) 6.98 (d, J = 8.08 Hz, 1 H) 7.12 (t, J = 7.83 Hz, 1 H) 8.03 (t, J = 4.93 Hz, 1 H) 11.46 (br. s., 1 H) | 329.2 |

| Ex | Structure | Name | 1H NMR | MS(ES) [M + H]+ |
|---|---|---|---|---|
| 39 | 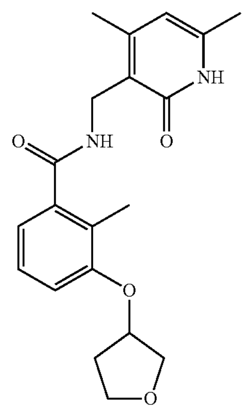 [SMILES: Cc1cc(C)c(CNC(=O)c2cccc(OC3CCOC3)c2C)c(=O)[nH]1] | N-((4,6-dimethyl-2-oxo-1,2-dihydropyridin-3-yl)methyl)-2-methyl-3-((tetrahydrofuran-3-yl)oxy)benzamide | 1.91-1.99 (m, 1 H) 2.09 (s, 3 H) 2.11 (s, 3 H) 2.15-2.24 (m, 4 H) 3.74-3.87 (m, 3 H) 3.90 (dd, J = 10.11, 4.55 Hz, 1 H) 4.25 (s, 1 H) 4.26 (s, 1 H) 4.99-5.06 (m, 1 H) 5.86 (s, 1 H) 6.82 (d, J = 7.07 Hz, 1 H) 6.96 (d, J = 8.08 Hz, 1 H) 7.14 (t, J = 7.83 Hz, 1 H) 8.06 (t, J = 4.93 Hz, 1 H) 11.46 (s, 1 H) | 357.1 |
| 40 | 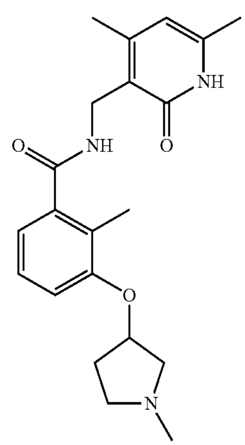 [SMILES: Cc1cc(C)c(CNC(=O)c2cccc(OC3CCN(C)C3)c2C)c(=O)[nH]1] | N-((4,6-dimethyl-2-oxo-1,2-dihydropyridin-3-yl)methyl)-2-methyl-3-((1-methylpyrrolidin-3-yl)oxy)benzamide | 1.76 (ddd, J = 12.57, 6.63, 2.78 Hz, 1 H) 2.08 (s, 3 H) 2.11 (s, 3 H) 2.19 (s, 3 H) 2.24-2.29 (m, 4 H) 2.35-2.41 (m, 1 H) 2.56 (dd, J = 10.36, 2.78 Hz, 1 H) 2.61-2.67 (m, 1 H) 2.80 (dd, J = 10.36, 6.06 Hz, 1 H) 4.25 (s, 1 H) 4.26 (s, 1 H) 4.82-4.87 (m, 1 H) 5.85 (s, 1 H) 6.79 (d, J = 6.82 Hz, 1 H) 6.88 (d, J = 8.08 Hz, 1 H) 7.09-7.14 (m, 1 H) 8.05 (t, J = 4.93 Hz, 1 H) 11.44 (br. s., 1 H) | 370.2 |
| 41 | 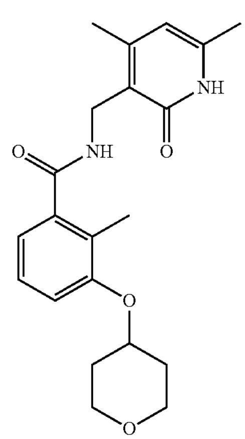 [SMILES: Cc1cc(C)c(CNC(=O)c2cccc(OC3CCOCC3)c2C)c(=O)[nH]1] | N-((4,6-dimethyl-2-oxo-1,2-dihydropyridin-3-yl)methyl)-2-methyl-3-((tetrahydro-2H-pyran-4-yl)oxy)benzamide | 1.61 (m, J = 12.82, 8.53, 4.11, 4.11 Hz, 2 H) 1.90-1.98 (m, 2 H) 2.11 (s, 3 H) 2.13 (s, 3 H) 2.19 (s, 3 H) 3.50 (ddd, J = 11.49, 8.46, 3.03 Hz, 2 H) 3.79-3.85 (m, 2 H) 4.25 (s, 1 H) 4.27 (s, 1 H) 4.57 (dt, J = 7.89, 4.01 Hz, 1 H) 5.86 (s, 1 H) 6.79-6.83 (m, 1 H) 7.04 (d, J = 7.58 Hz, 1 H) 7.12 (t, J = 7.83 Hz, 1 H) 8.05 (t, J = 4.93 Hz, 1 H) 11.46 (br. s., 1 H) | 371.5 |

Example 42

3-(sec-Butoxy)-N-((4,6-dimethyl-2-oxo-1,2-dihydro-pyridin-3-yl)methyl)-2-methyl-5-(methylsulfonyl)benzamide

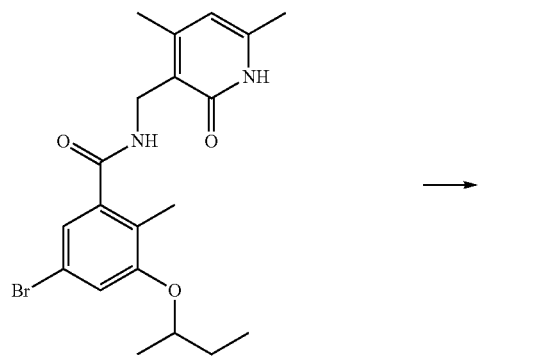

In a microwave vial, copper(II) trifluoromethanesulfonate (86 mg, 0.237 mmol) and methanesulfinate, sodium salt (57.0 mg, 0.475 mmol) were dissolved in dimethyl sulfoxide (DMSO) (2 mL). The solution stirred under nitrogen for 10 min before, at which time was added N1,N2-dimethyl-ethane-1,2-diamine (0.054 mL, 0.498 mmol) and 5-bromo-3-(sec-butoxy)-N-((4,6-dimethyl-2-oxo-1,2-dihydropyridin-3-yl)methyl)-2-methylbenzamide (100 mg, 0.237 mmol). The dark blue clear solution was stirred at 120° C. for 2 hours. The LCMS spectrum of the crude mixture showed 52% conversion into desired product. 43 mg of copper(II) trifluoromethanesulfonate, 38 mg of methanesulfinate, sodium salt and 27 L of N1,N2-dimethylethane-1,2-diamine were added and the deep blue solution was stirred at 120° C. for 1.75 h, then at room temperature for 4 days. The mixture was purified by Gilson reversed-phase HPLC (30×100 Varian Polaris C18, 3-70% gradient of MeCN in water with 0.1% TFA over 12 minutes) to give 3-(sec-butoxy)-N-((4,6-dimethyl-2-oxo-1,2-dihydropyridin-3-yl)methyl)-2-methyl-5-(methylsulfonyl)benzamide (44.6 mg, 0.105 mmol, 44.2% yield) as a white solid. $^1$H NMR (400 MHz, DMSO-$d_6$) δ 0.94 (t, J=7.33 Hz, 3H) 1.26 (d, J=6.06 Hz, 3H) 1.63-1.72 (m, 2H) 2.12 (s, 3H) 2.17 (s, 3H) 2.20 (s, 3H) 3.21 (s, 3H) 4.28 (s, 1H) 4.29 (s, 1H) 4.56 (q, J=5.81 Hz, 1H) 5.87 (s, 1H) 7.29 (d, J=1.52 Hz, 1H) 7.40 (d, J=1.77 Hz, 1H) 8.38 (t, J=4.93 Hz, 1H) 11.50 (s, 1H). MS(ES) [M+H]$^+$ 421.3.

Example 43

N-((4,6-dimethyl-2-oxo-1,2-dihydropyridin-3-yl)methyl)-3-(isopropylamino)-2-methyl-5-(methylsulfonyl)benzamide

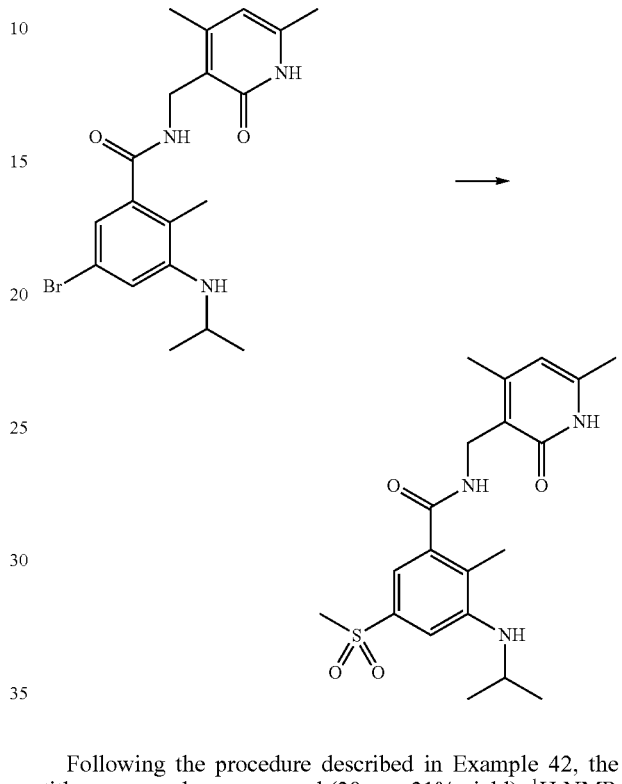

Following the procedure described in Example 42, the title compound was prepared (20 mg, 31% yield). $^1$H NMR (400 MHz, DMSO-$d_6$) δ 1.20 (s, 3H) 1.21 (s, 3H) 2.08 (s, 3H) 2.11 (s, 3H) 2.19 (s, 3H) 3.13 (s, 3H) 3.70 (s, 1H) 4.27 (s, 1H) 4.28 (s, 1H) 5.02 (d, J=8.08 Hz, 1H) 5.87 (s, 1H) 6.91 (d, J=1.52 Hz, 1H) 6.94-6.97 (m, 1H) 8.23 (t, J=4.93 Hz, 1H) 11.48 (br. s., 1H). MS(ES) [M+H]$^+$ 406.3.

Example 44

3-(sec-Butoxy)-5-cyano-N-((4,6-dimethyl-2-oxo-1,2-dihydropyridin-3-yl)methyl)-2-methylbenzamide

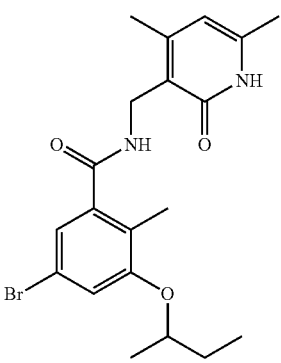

111

-continued

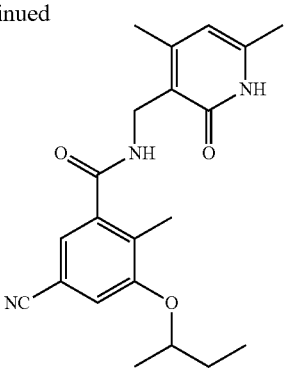

5-Bromo-3-(sec-butoxy)-N-((4,6-dimethyl-2-oxo-1,2-dihydropyridin-3-yl)methyl)-2-methylbenzamide (100 mg, 0.24 mmol), dicyanozinc (32 mg, 0.27 mmol), PdCl$_2$(dppf)-CH$_2$Cl$_2$ adduct (29.1 mg, 0.04 mmol), Dppf (32.9 mg, 0.06 mmol) and zinc (3.9 mg, 0.06 mmol) in 3 mL of DMA were degassed for 10 min and sealed in a microwave vial. The mixture was heated to 120° C. for 19 hours. The reaction was allowed to cool to ambient temperature, quenched with water and stirred for 1 h. The resulting precipitate was filtered, dissolved in DCM/MeOH (1:1), preabsorbed on silica gel and purified using normal phase chromatography: DCM/(40 g, gradient 0 to 80:20:2 in DCM) to give a brown oil. EtOAc was added (along with some hexanes) and the resulting precipitate was filtered, air-dried for 15 min, and dried in vacuum-oven overnight to give the title compound (46 mg, 53% yield). $^1$H NMR (400 MHz, DMSO-d$_6$) δ 0.92 (t, J=7.45 Hz, 3H) 1.23 (d, J=6.06 Hz, 3H) 1.57-1.71 (m, 2H) 2.11 (s, 3H) 2.14 (s, 3H) 2.17-2.21 (m, 3H) 4.25 (s, 1H) 4.26 (s, 1H) 4.53 (q, J=6.06 Hz, 1H) 5.86 (s, 1H) 7.21 (d, J=1.26 Hz, 1H) 7.45 (d, J=1.26 Hz, 1H) 8.33 (t, J=5.05 Hz, 1H) 11.48 (br. s., 1H). MS(ES) [M+H]$^+$368.3.

Example 45

5-Cyano-N-((4,6-dimethyl-2-oxo-1,2-dihydropyridin-3-yl)methyl)-3-isopropoxy-2-methylbenzamide

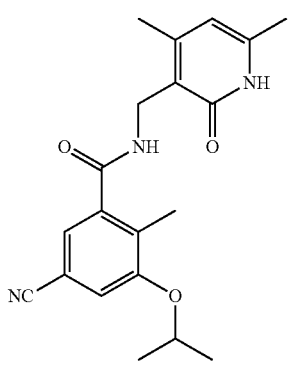 [SMILES: Cc1cc(C)c(CNC(=O)c2cc(C#N)cc(OC(C)C)c2C)c(=O)[nH]1]

Following the procedure described in Examples 44 and 1, the title compound was prepared. $^1$H NMR (400 MHz, DMSO-d$_6$) δ1.27 (s, 3H) 1.28 (s, 3H) 2.11 (s, 3H) 2.13 (s, 3H) 2.19 (s, 3H) 4.25 (s, 1H) 4.26 (s, 1H) 4.68-4.76 (m, 1H) 5.87 (s, 1H) 7.22 (d, J=1.26 Hz, 1H) 7.47 (d, J=1.26 Hz, 1H) 8.33 (t, J=4.93 Hz, 1H) 11.49 (br. s., 1H). MS(ES) [M+H]$^+$ 354.2.

112

Example 46

3-(sec-Butoxy)-N-((4,6-dimethyl-2-oxo-1,2-dihydropyridin-3-yl)methyl)-5-methoxy-2-methylbenzamide

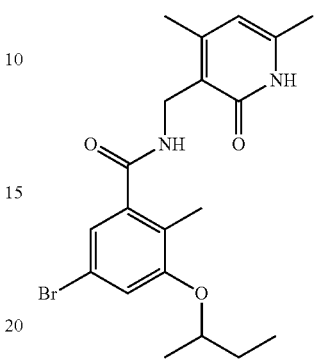

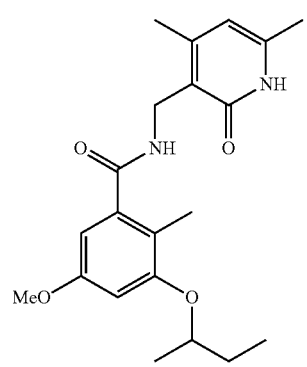

To 5-bromo-3-(sec-butoxy)-N-((4,6-dimethyl-2-oxo-1,2-dihydropyridin-3-yl)methyl)-2-methylbenzamide (130 mg, 0.31 mmol) and copper(I) iodide (70.5 mg, 0.37 mmol) was added N-methyl-2-pyrrolidone (NMP) (3 mL). To the mixture was added dropwise a solution of 25 wt % sodium methoxide in MeOH (0.28 mL, 1.23 mmol) with stirring. The reaction was heated to 120° C. and stirred for 36 h. The reaction mixture was then diluted with water and EtOAc was added. The mixture was filtered through Celite and washed with EtOAc. The filtrate was poured into a separatory funnel, the organic phase was separated, washed with brine, dried over MgSO$_4$, filtered, and concentrated under vacuum. The residue was purified by Gilson reversed-phase HPLC (30×100 Varian Polaris C18, 20-70% gradient of MeCN in water with 0.1% TFA over 12 minutes). Most of the solvent was evaporated and sat. aq. NaHCO$_3$ was added. The solids that crashed out were filtered, air-dried for 15 min and dried in vacuum-oven overnight to give the title compound (24 mg, 20% yield). $^1$H NMR (400 MHz, DMSO-d$_6$) δ0.92 (t, J=7.45 Hz, 3H) 1.21 (d, J=6.06 Hz, 3H) 1.55-1.68 (m, 2H) 1.96-2.04 (m, 3H) 2.08-2.13 (m, 3H) 2.18 (s, 3H) 3.68-3.76 (m, 3H) 4.25 (d, J=5.05 Hz, 2H) 4.37 (sxt, J=5.96 Hz, 1H) 5.86 (s, 1H) 6.36 (d, J=2.27 Hz, 1H) 6.52 (d, J=2.27 Hz, 1H) 8.03 (t, J=4.93 Hz, 1H) 11.47 (s, 1H). MS(ES) [M+H]$^+$ 373.2.

Example 47

N-((4,6-dimethyl-2-oxo-1,2-dihydropyridin-3-yl)methyl)-3-isopropoxy-5-methoxy-2-methylbenzamide

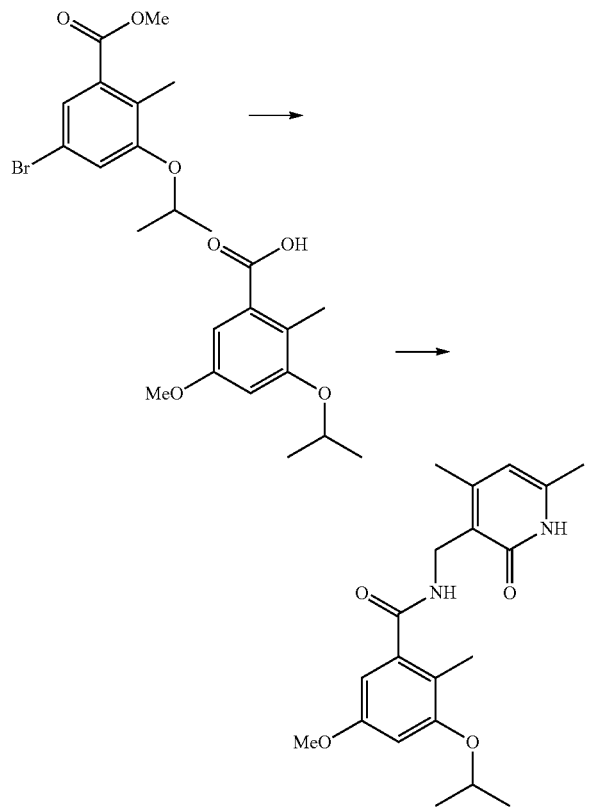

Following the procedure described in Examples 46 and 1, the title compound was prepared. $^1$H NMR (400 MHz, DMSO-$d_6$) δ 1.24 (s, 3H) 1.26 (s, 3H) 1.99 (s, 3H) 2.11 (s, 3H) 2.18 (s, 3H) 3.72 (s, 3H) 4.24 (s, 1H) 4.25 (s, 1H) 4.54-4.60 (m, 1H) 5.86 (s, 1H) 6.37 (d, J=2.27 Hz, 1H) 6.55 (d, J=2.53 Hz, 1H) 8.04 (t, J=4.93 Hz, 1H). MS(ES) [M+H]$^+$ 359.2.

Example 48

N-((4,6-dimethyl-2-oxo-1,2-dihydropyridin-3-yl)methyl)-3-(isopropylamino)-2-methylbenzamide

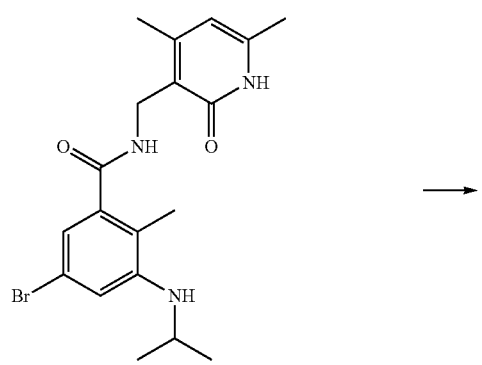

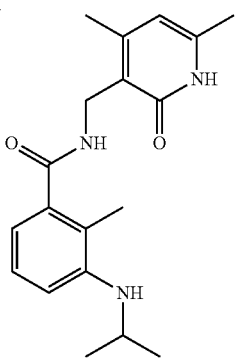

To a mixture of 5-bromo-N-((4,6-dimethyl-2-oxo-1,2-dihydropyridin-3-yl)methyl)-3-(isopropylamino)-2-methylbenzamide (84.7 mg, 0.208 mmol) in EtOAc (3 mL), THF (1 mL), MeOH (0.5 mL) and triethylamine (0.5 mL) was added Pd/C (10% wet Degussa type; 22 mg, 0.21 mmol). The insoluble mixture was stirred under a balloon of hydrogen at room temperature for 1.5 h. LCMS showed 16% conversion. The mixture was then stirred at room temperature for 18 h. LCMS showed no change. More Pd/C was added and the reaction was stirred at room temperature for 5 h. LCMS showed only 32% conversion. DMF (0.5 mL) was added to try to solubilize the compound and the reaction solution was filtered through celite, washed with ethyl acetate and evaporated. The residue was dissolved in a mixture of EtOAc (4 mL). THF (1.6 mL) and DMF (0.5 mL) (The mixture was first a clear solution but after 10 minutes, some solid started crystallizing) and hydrogenated again using Pd/C (10% wet Degussa type; 22 mg, 0.21 mmol) and a balloon of hydrogen. It was stirred at room temperature overnight. LCMS showed 35% conversion. The reaction mixture was filtered through celite, washed with EtOAc and the filtrate was evaporated. The residue was dissolved in EtOH and hydrogenated using H-Cube hydrogenation reactor during 4 hours at ambient pressure. LCMS showed complete conversion.

The reaction mixture was evaporated to give a dark black residue, which was dissolved in EtOH and filtered through Acrodisk 13 CR PTFE 0.2 μm to remove the residual palladium. The solution was evaporated. Purification of the residue by normal phase chromatography DCM/MeOH/NH$_4$OH (12 g Gold column, gradient 0 to 80:20:2 in DCM) gave N-((4,6-dimethyl-2-oxo-1,2-dihydropyridin-3-yl)methyl)-3-(isopropylamino)-2-methylbenzamide (10.2 mg, 0.030 mmol, 14.50% yield). $^1$H NMR (400 MHz, DMSO-$d_6$) δ 1.16 (s, 3H) 1.17 (s, 3H) 2.00 (s, 3H) 2.11 (s, 3H) 2.19 (s, 3H) 3.61 (dd, J=13.89, 6.32 Hz, 1H) 4.24 (s, 1H) 4.25 (s, 1H) 4.36 (d, J=8.08 Hz, 1H) 5.85 (s, 1H) 6.44 (d, J=6.82 Hz, 1H) 6.58 (d, J=8.08 Hz, 1H) 6.98 (t, J=7.83 Hz, 1H) 7.88 (t, J=4.93 Hz, 1H) 11.45 (br. s., 1H. MS(ES) [M+H]$^+$ 328.2.

ASSAY PROTOCOL

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on Histone H3 of a mononucleosome, purified from HeLa cells. Mononucleosomes were captured on SPA beads and the resulting signal is read on a ViewLux plate reader.

Part A. Compound Preparation
1. Prepare 10 mM stock of compounds from solid in 100% DMSO.
2. Set up an 11-point serial dilution (1:3 dilution, top concentration 10 mM) in 100% DMSO for each test compound in a 384 well plate leaving columns 6 and 18 for DMSO controls.
3. Dispense 100 nL of compound from the dilution plate into reaction plates (Grenier Bio-One, 384-well, Cat#784075).

Part B. Reagent Preparation
Prepare the following solutions:
1. 50 mM Tris-HCl, pH 8: Per 1 L of base buffer, combine 1 M Tris-HCl, pH 8 (50 mL) and distilled water (950 mL).
2. 1× Assay Buffer: Per 10 mL of 1× Assay Buffer, combine 50 mM Tris-HCl, pH 8 (9958 uL), 1 M $MgCl_2$ (20 uL), 2 M DTT (20 uL), and 10% Tween-20 (2 uL) to provide a final concentration of 50 mM Tris-HCl, pH 8, 2 mM $MgCl_2$, 4 mM DTT, 0.002% Tween-20.
3. 2× Enzyme Solution: Per 10 mL of 2× Enzyme Solution, combine 1× Assay Buffer and PRC2 complex to provide a final enzyme concentration of 10 nM.
4. SPA Bead Suspension: Per 1 mL of SPA Bead Suspension, combine PS-PEI coated LEADSeeker beads (40 mg) and $ddH_2O$ (1 mL) to provide a final concentration of 40 mg/mL.
5. 2× Substrate Solution: Per 10 mL of 2× Substrate Solution, combine 1× Assay Buffer (9728.55 uL), 800 ug/mL mononucleosomes (125 uL), 1 mM cold SAM (4 uL), and 7.02 uM 3H-SAM (142.45 uL; 0.55 mCi/mL) to provide a final concentration of 5 ug/mL nucleosomes, 0.2 uM cold SAM, and 0.05 uM 3H-SAM.
6. 2.67× Quench/Bead Mixture: Per 10 mL of 2.67× Quench/Bead Mixture, combine $ddH_2O$ (9358 uL), 10 mM cold SAM (267 uL), 40 mg/mL Bead Suspension (375 uL) to provide a final concentration of 100 uM cold SAM and 0.5 mg/mL SPA beads.

Part C. Assay Reaction in 384-Well Grenier Bio-One Plates
Compound Addition
1. Dispense 100 nL/well of 100× Compound to test wells (as noted above).
2. Dispense 100 nL/well of 100% DMSO to columns 6 & 18 for high and low controls, respectively.

Assay
1. Dispense 5 uL/well of 1× Assay Buffer to column 18 (low control reactions).
2. Dispense 5 uL/well of 2× Enzyme Solution to columns 1-17, 19-24.
3. Spin assay plates for ~1 minute at 500 rpm.
4. Stack the assay plates, covering the top plate.
5. Incubate the compound/DMSO with the enzyme for 30 minutes at room temperature.
6. Dispense 5 uL/well of 2× Substrate Solution to columns 1-24.
7. Spin assay plates for ~1 minute at 500 rpm.
8. Stack the assay plates, covering the top plate.
9. Incubate the assay plates at room temperature for 1 hour.

Quench/Bead Addition
1. Dispense 5 uL/well of the 3× Quench/Bead Mixture to columns 1-24.
2. Seal the top of each assay plate with adhesive TopSeal.
3. Spin assay plates for 1 minute at 500 rpm.
4. Equilibrate the plates for >20 min.

Read Plates
1. Read the assay plates on the Viewlux Plate Reader utilizing the 613 nm emission filter with a 300 s read time.

Reagent addition can be done manually or with automated liquid handler.

The final DMSO concentration in this assay is 1%.

The positive control is in column 6; negative control is in column 18.

Final starting concentration of compounds is 100 M.

Results

Percent inhibition was calculated relative to the DMSO control for each compound concentration and the resulting values were fit using standard $IC_{50}$ fitting parameters within the ABASE data fitting software package.

Exemplified compounds of the present invention were generally tested according to the above or an analogous assay and were found to be inhibitors of EZH2. The $IC_{50}$ values ranged from about 13 nM to about 2.5 M; The $IC_{50}$ values of the more active compounds range from about 1 nM to about 500 nM; The most active compounds are under 50 nM. Exemplary compounds with specific biological activities tested according to assays described herein are listed in the following table. Repeating the assay run(s) may result in a somewhat different.

| Example | EZH2 IC50 (nM) |
| --- | --- |
| 1 | 501 |
| 2 | 40 |
| 4 | 50 |
| 24 | 250 |
| 20 | 13 |
| 26 | 1000 |
| 36 | 2500 |
| 44 | 316 |

The invention claimed is:
1. A method of treating non-Hodgkin's lymphoma comprising administering to a patient with non-Hodgkin's lymphoma a therapeutically effective amount of a compound of formula (I):

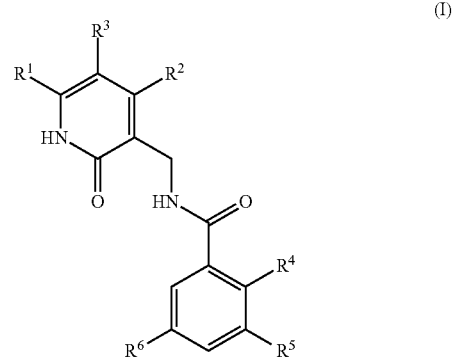

wherein:
$R^1$ is methyl;
$R^2$ is methyl;
$R^3$ is hydrogen;
$R^4$ is methyl;
$R^5$ is $-NR^aR^b$;

$R^6$ is phenyl, wherein said phenyl is optionally substituted by —$(C_1\text{-}C_6)$alkyl$(R^c)$;

$R^c$ is —$NR^aR^b$; and $R^a$ and $R^b$ are each independently hydrogen, $(C_1\text{-}C_8)$alkyl, $(C_2\text{-}C_8)$alkenyl, $(C_2\text{-}C_8)$alkynyl, $(C_3\text{-}C_{10})$cycloalkyl, $(C_5\text{-}C_8)$cycloalkenyl, heterocycloalkyl, or aryl, wherein said $(C_1\text{-}C_8)$alkyl, $(C_2\text{-}C_8)$alkenyl, $(C_2\text{-}C_8)$alkynyl, cycloalkyl, cycloalkenyl, heterocycloalkyl, or aryl group is optionally substituted by 1, 2 or 3 groups independently selected from the group consisting of halo, hydroxyl, $(C_1\text{-}C_4)$alkoxy, amino, $(C_1\text{-}C_4)$alkylamino, —$N((C_1\text{-}C_4)\text{alkyl})_2$, —$CO_2H$, —$CO_2(C_1\text{-}C_4)$alkyl, —$CONH_2$, —$CONH(C_1\text{-}C_4)$alkyl, —$CON((C_1\text{-}C_4)\text{alkyl})_2$, —$SO_2(C_1\text{-}C_4)$alkyl, —$SO_2NH_2$, —$SO_2NH(C_1\text{-}C_4)$alkyl, and —$SO_2N((C_1\text{-}C_4)\text{alkyl})_2$; and wherein said heterocycloalkyl is selected from the group consisting of pyrrolidinyl, tetrahydrofuranyl, piperidinyl, piperazinyl, morpholinyl, thiomorpholinyl, and tetrahydropyranyl;

or $R^a$ and $R^b$ taken together with the nitrogen to which they are attached represent a 5 or 6 membered saturated ring, optionally containing an additional heteroatom selected from oxygen, nitrogen, and sulfur, wherein said ring is optionally substituted by 1, 2 or 3 groups independently selected from the group consisting of $(C_1\text{-}C_4)$alkyl, $(C_1\text{-}C_4)$haloalkyl, amino, $(C_1\text{-}C_4)$alkylamino, $((C_1\text{-}C_4)\text{alkyl})((C_1\text{-}C_4)\text{alkyl})$amino, hydroxyl, oxo, $(C_1\text{-}C_4)$alkoxy, and $(C_1\text{-}C_4)$alkoxy$(C_1\text{-}C_4)$alkyl;

or a pharmaceutically acceptable salt thereof.

* * * * *

Disclaimer

9,956,210 B2 - Joelle Lorraine Burgess, Collegeville, PA (US); Steven David Knight, Collegeville, PA (US). ENHANCER OF ZESTE HOMOLOG 2 INHIBITORS. Patent dated May 1, 2018. Disclaimer filed September 25, 2020, by the assignee GlaxoSmithKline LLC.

Hereby enters this disclaimer to the complete claim 1 of said patent.

*(Official Gazette, May 25, 2021)*